United States Patent
Abouabdellah et al.

(10) Patent No.: US 8,889,702 B2
(45) Date of Patent: Nov. 18, 2014

(54) DERIVATIVES OF AZASPIRANYL-ALKYLCARBAMATES OF 5-MEMBER HETEROCYCLIC COMPOUNDS, PREPARATION THEREOF AND THERAPEUTIC USE THEREOF

(75) Inventors: Ahmed Abouabdellah, Paris (FR); Nathalie Chereze, Paris (FR); Aude Fayol, Paris (FR); Alistair Lochead, Paris (FR); Mourad Saady, Paris (FR); Julien Vache, Paris (FR); Philippe Yaiche, Paris (FR)

(73) Assignee: Sanofi, Paris (FR)

( * ) Notice: Subject to any disclaimer, the term of this patent is extended or adjusted under 35 U.S.C. 154(b) by 419 days.

(21) Appl. No.: 13/145,926

(22) PCT Filed: Feb. 4, 2010

(86) PCT No.: PCT/FR2010/050183
§ 371 (c)(1),
(2), (4) Date: Sep. 15, 2011

(87) PCT Pub. No.: WO2010/089510
PCT Pub. Date: Aug. 12, 2010

(65) Prior Publication Data
US 2011/0319381 A1 Dec. 29, 2011

(30) Foreign Application Priority Data
Feb. 5, 2009 (FR) ...................................... 09 00493

(51) Int. Cl.
*A61K 31/4704* (2006.01)
*A61K 31/4427* (2006.01)
*C07D 413/14* (2006.01)
*C07D 417/14* (2006.01)

(52) U.S. Cl.
CPC ............ *C07D 417/14* (2013.01); *C07D 413/14* (2013.01)
USPC .............................................. 514/278; 546/16

(58) Field of Classification Search
CPC . C07D 417/14; C07D 413/14; A61K 31/4439
USPC ............................................ 546/16; 514/278
See application file for complete search history.

(56) References Cited

FOREIGN PATENT DOCUMENTS

| WO | WO 02/42269 A1 | 5/2002 |
| WO | WO2004/033422 A1 | 4/2004 |
| WO | WO2004/099176 A1 | 11/2004 |

OTHER PUBLICATIONS

Dorwald F. A. Side Reactions in Organic Synthesis, 2005, Wiley: VCH, Weinheim p. IX of Preface.*

International Search Report dated Aug. 3, 2010 issued in PCT/FR2010/050183.
International Preliminary Report on Patentability dated Aug. 9, 2011.
Baker D. et al., "Endocannabinoids Control Spasticity in a Multiple Sclerosis Model", The BASEB Journal 15:300-302 (Feb. 2001).
Bifulco M. et al., "Targeting the Endocannabinoid System in Cancer Therapy: A Call for Future Research", Nature Medicine 8(6):547-550 (Jun. 2002).
Carley D.W. et al., "Functional Role for Cannabinoids in Respiratory Stability During Sleep", Sleep 25(4):388-395 (2002).
Consroe P., "Brain Cannabinoid Systems as Targets for the Therapy of Neurological Disorders", Neurobiology of Disease 5:534-551 (1998).
Depetrocellis L. et al., "Endocannabinoids and Fatty Acids Amides in Cancer, Inflammation and Related Disorders", Chemistry and Physics of Lipids, 108:191-209 (2000).
Hillard C.J., "Endocannabinoids and Vascular Function", The Journal of Pharmacology and Experimental Therapeutics 294(1):27-32 (2000).
Izzo A.A. et al., "The Gastrointestinal Pharmacology of Cannabinoids", Current Opinion in Pharmacology 1:597-603 (2001).
Jaggar S.I. et al., "The Anti-Hyperalgesic Actions of the Cannabinoid Anandamide and the Putative CB2 Receptor Agonist Palmitoylethanolamide in Visceral and Somatic Inflammatory Pain", Pain 76:189-199 (1998).
Martin B.R. et al., "Cannabinoid Transmission and Pain Perception", Neurobiology of Disease 5:447-461 (1998).
Mechoulam R. et al., "5 Towards Cannabinoid Drugs-Revisited", Progress in Medicinal Chemistry 35:199-243 (1998).
Mendelson W.B. et al., "The Hypnotic Actions of the Fatty Acid Amide, Oleanmide", Neuropsychopharmacology 25 (S5):S36-S39 (2001).
Murillo-Rodriguez E. et al., "Anandamide-Induced Sleep is Blocked by SR141716A, a CBI Receptor Antagonist and by U73122, a Phospholipase C Inhibitor", Neuropharmacology and Neurotoxicology 12(10):2131-2136 (Jul. 2001).

(Continued)

*Primary Examiner* — Rita Desai
(74) *Attorney, Agent, or Firm* — Scully, Scott, Murphy & Presser P.C.

(57) ABSTRACT

The invention relates to a compound of the general formula (I) in which $R_2$ is a hydrogen or fluorine atom or a hydroxyl, cyano, trifluoromethyl, $C_{1-6}$-alkyl, $C_{1-6}$-alkoxy, $NR_8R_9$ group; m, n, o and p are independently an integer equal to 0, 1, 2 or 3; A is a covalent bond or a $C_{1-8}$-alkylene group; $R_1$ is an optionally substituted aryl or heteroaryl group; $R_3$ is a hydrogen or fluorine atom or a $C_{1-6}$-alkyl group or a trifluoromethyl group; $R_4$ is an optionally substituted 5-member heterocyclic compound; the compound being in the form of a base or acid addition salt. The invention also relates to the therapeutic use thereof.

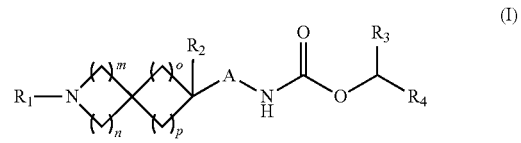

(I)

12 Claims, No Drawings

(56) References Cited

OTHER PUBLICATIONS

Piomelli D. et al,. "The Endocannabinoid System as a Target for Therapeutic Drugs", TiPS 21:218-224 (Jun. 2000).

Porter A.C. et al., "The Endocannabinoid Nervous System: Unique Opportunities for Therapeutic Intervention", Pharmacology & Therapeutics 90:45-60 (2001).

Salzet M. et al., "Comparative Biology of the Endocannabinoid System", Eur. J. Biochem. 267:4917-4927 (2000).

Smith P.J.W. et al., "Anandamide Induces Cardiovascular and Respiratory Reflexes Via Vasosensory Nerves in the Anaesthetized Rat", British Journal of Pharmacology 134:655-663 (2001).

Szallasi A. et al., "Vanilloid Receptor Ligands-Hopes and Realities for the Future", Drugs & Aging 18(8):561-573 (2001).

Ueda N. et al., "The Fatty Acid Amide Hydrolase (FAAH)", Chemistry and Physics of Lipids 108:107-121 (2000).

Van Sickle M.D. et al., "Cannabinoids Inhibit Emesis Through CB1 Receptors in the Brainstem of the Ferret", Gastroenterology 121(4):767-774 (2001).

\* cited by examiner

DERIVATIVES OF AZASPIRANYL-ALKYLCARBAMATES OF 5-MEMBER HETEROCYCLIC COMPOUNDS, PREPARATION THEREOF AND THERAPEUTIC USE THEREOF

The invention relates to azaspiranyl alkylcarbamate derivatives of 5-membered heterocycles, to their preparation and to their therapeutic use.

There is still a need to find and develop products that inhibit the enzyme FAAH (Fatty Acid Amide Hydrolase). The compounds of the invention satisfy this aim. These compounds should have metabolic and pharmacokinetic properties and a safety index that allow their use as medicaments.

The compounds of the invention correspond to the general formula (I):

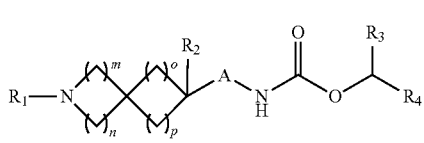

in which $R_2$ represents a hydrogen or fluorine atom or a hydroxyl, cyano, trifluoromethyl, $C_{1-6}$-alkyl, $C_{1-6}$-alkoxy or $NR_8R_9$ group;

m, n, o and p represent, independently of each other, an integer equal to 0, 1, 2 or 3;

A represents a covalent bond or a group $C_{1-8}$-alkylene;

$R_1$ represents a group $R_5$ optionally substituted with one or more groups $R_6$ and/or $R_7$;

$R_5$ represents a group chosen from phenyl, pyridyl, pyridazinyl, pyrimidinyl, pyrazinyl, triazinyl, naphthyl, quinolinyl, isoquinolinyl, phthalazinyl, quinazolinyl, quinoxalinyl, cinnolinyl and naphthyridinyl;

$R_6$ represents a halogen atom or a cyano, —$CH_2CN$, nitro, hydroxyl, $C_{1-6}$-alkyl, $C_{1-6}$-alkoxy, $C_{1-6}$-thioalkyl, $C_{1-6}$-haloalkyl, $C_{1-6}$-haloalkoxy, $C_{1-6}$-halothioalkyl, $C_{3-7}$-cycloalkyl, $C_{3-7}$-cycloalkyl-$C_{1-3}$-alkylene, $C_{3-7}$-cycloalkyl-$C_{1-3}$-alkylene-O—, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $SO_2R_8$, $SO_2NR_8R_9$ or —O—($C_{1-3}$-alkylene)-O— group;

$R_7$ represents a group chosen from furyl, pyrrolyl, thienyl, oxazolyl, isoxazolyl, thiazolyl, isothiazolyl, imidazolyl, pyrazolyl, oxadiazolyl, thiadiazolyl, phenyl, pyridyl, pyridazinyl, pyrimidinyl, pyrazinyl, triazinyl, naphthyl, quinolinyl, isoquinolinyl, phthalazinyl, quinazolinyl, quinoxalinyl, cinnolinyl, naphthyridinyl, imidazopyrimidinyl, thienopyrimidinyl, benzofuryl, benzothienyl, benzimidazolyl, benzoxazolyl, benzisoxazolyl, benzothiazolyl, benzisothiazolyl, indolyl, isoindolyl, indazolyl, pyrrolopyridyl, furopyridyl, thienopyridyl, imidazopyridyl, pyrazolopyridyl, oxazolopyridyl, isoxazolopyridyl, thiazolopyridyl, phenyloxy, benzyloxy and pyrimidinoxy; or the group(s) $R_7$ possibly being substituted with one or more groups $R_6$ that may be identical to or different from each other;

$R_3$ represents a hydrogen or fluorine atom, a group $C_{1-6}$-alkyl or a trifluoromethyl group;

$R_4$ represents a group chosen from furyl, pyrrolyl, thienyl, isothiazolyl, oxazolyl, isoxazolyl, pyrazolyl, oxadiazolyl, thiadiazolyl, imidazolyl, triazolyl and tetrazolyl;

this group being optionally substituted with one or more substituents chosen from a halogen atom, a group $C_{1-6}$-alkyl, $C_{1-6}$-haloalkyl, $C_{3-7}$-cycloalkyl, $C_{3-7}$-cycloalkyl-$C_{1-3}$-alkylene, $C_{1-6}$-haloalkoxy, cyano, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $CON(R_8)(C_{1-3}$-alkylene-$NR_{10}R_{11})$, $SO_2R_8$, $SO_2NR_8R_9$, —O—($C_{1-3}$-alkylene)-O—, phenyl, phenyloxy, benzyloxy, pyridyl, pyrazinyl, pyridazinyl, triazinyl or pyrimidinyl; the phenyl, phenyloxy, pyridyl, pyrazinyl, pyridazinyl, triazinyl and pyrimidinyl groups possibly being substituted with one or more substituents chosen from a halogen atom and a cyano, nitro, $C_{1-6}$-alkyl, $C_{1-6}$-alkoxy, $C_{1-6}$-thioalkyl, $C_{1-6}$-haloalkyl, $C_{1-6}$-haloalkoxy, $C_{1-6}$-halothioalkyl, $C_{3-7}$-cycloalkyl or $C_{3-7}$-cycloalkyl-$C_{1-3}$-alkylene group;

$R_8$ and $R_9$ represent, independently of each other, a hydrogen atom or a group $C_{1-6}$-alkyl, or form, with the atom(s) that bear(s) them, in the case of $NR_8R_9$, a ring chosen from azetidine, pyrrolidine, piperidine, morpholine, thiomorpholine, azepine, oxazepine and piperazine rings, this ring being optionally substituted with a group $C_{1-6}$-alkyl or benzyl;

in the case of $NR_8COR_9$, a lactam ring; in the case of $NR_8CO_2R_9$, a oxazolidinone, oxazinone or oxazepinone ring; in the case of $NR_8SO_2R_9$, a sultam ring; in the case of $NR_8SO_2NR_8R_9$, a thiazolidine dioxide or thiadiazinane dioxide ring;

$R_{10}$ and $R_{11}$ represent, independently of each other, a hydrogen atom or a group $C_{1-6}$-alkyl.

Among the compounds of general formula (I), a first subgroup of compounds is formed from the compounds for which $R_2$ represents a hydrogen atom.

Among the compounds of general formula (I), a second subgroup of compounds is formed from the compounds for which the group

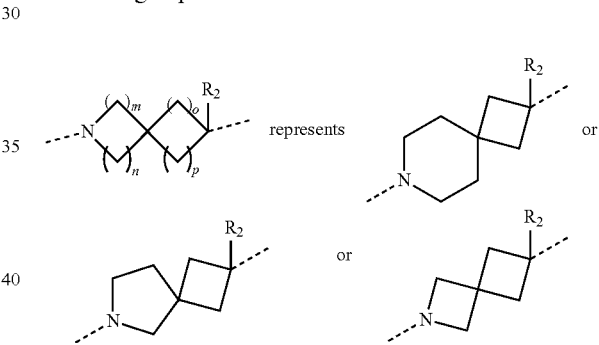

$R_2$ being as defined in the general formula (I).

Among the compounds of general formula (I), a third subgroup of compounds is formed from the compounds for which the group

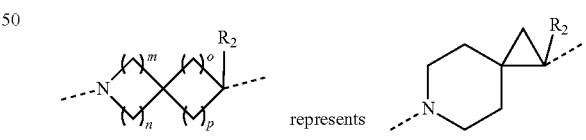

$R_2$ being as defined in the general formula (I).

Among the compounds of general formula (I), a fourth subgroup of compounds is formed from the compounds for which A represents a covalent bond or a group $C_{1-8}$-alkylene, more particularly a methylene group.

Among the compounds of general formula (I), a fifth subgroup of compounds is formed from the compounds for which $R_1$ represents a group $R_5$ optionally substituted with one or more groups $R_6$ and/or $R_7$;

$R_5$ represents a pyrimidinyl, pyrazinyl, pyridinyl or quinolinyl group;

R₆ represents a halogen atom, more particularly a bromine, fluorine or chlorine atom, a group $C_{1-6}$-haloalkyl, more particularly trifluoromethyl, or a group $C_{1-6}$-alkyl, more particularly an isobutyl;

R₇ represents a phenyl, which may be substituted with one or more groups R₆ that are identical to or different from each other.

Among the compounds of general formula (I), a sixth subgroup of compounds is formed from the compounds for which R₁ represents a group R₅ optionally substituted with one or more groups R₆ and/or R₇;

R₅ represents a pyridyl or quinolyl group;

R₆ represents a halogen atom, more particularly a bromine, fluorine or chlorine atom, or a group $C_{1-6}$-haloalkyl, more particularly trifluoromethyl;

R₇ represents a phenyl, which may be substituted with one or more groups R₆ that are identical to or different from each other.

Among the compounds of general formula (I), a seventh subgroup of compounds is formed from the compounds for which R₃ represents a hydrogen atom.

Among the compounds of general formula (I), an eighth subgroup of compounds is formed from the compounds for which R₄ represents a group chosen from a thiazolyl, an oxazolyl, an oxadiazolyl and an isoxazolyl;

this group being optionally substituted with one or more substituents chosen from a group $C_{1-6}$-alkyl, $CONR_8R_9$, $CON(R_8)$ ($C_{1-3}$-alkylene-$NR_{10}R_{11}$) or a phenyl; the phenyl group being optionally substituted with one or more substituents chosen from a halogen atom;

R₈, R₉, R₁₀ and R₁₁ represent, independently of each other, a hydrogen atom or a group $C_{1-6}$-alkyl, more particularly methyl.

Among the compounds of general formula (I), a ninth subgroup of compounds is formed from the compounds for which R₄ represents a group chosen from a thiazolyl, an oxazolyl and an isoxazolyl;

this group being optionally substituted with one or more groups $CONR_8R_9$;

R₈ and R₉ represent, independently of each other, a hydrogen atom or a group $C_{1-6}$-alkyl, more particularly methyl.

Among the compounds of general formula (I), a tenth subgroup of compounds is formed by the compounds of general formula (I) in which R₁ and/or R₂ and/or R₃ and/or R₄ and/or n and/or m and/or o and/or p and/or A are all as defined in the above groups.

Among the compounds of general formula (I), the following compounds may be mentioned (IUPAC nomenclature generated by the AutoNom software):

1. thiazol-4-ylmethyl[7-(6-fluoroquinolin-2-yl)-7-azaspiro[3.5]non-2-yl]carbamate
2. 3-carbamoylisoxazol-5-ylmethyl[7-(6-fluoroquinolin-2-yl)-7-azaspiro[3.5]non-2-yl]carbamate
3. 3-carbamoylisoxazol-5-ylmethyl[7-(5-trifluoromethylpyridin-2-yl)-7-azaspiro[3.5]non-2-yl]carbamate
4. 3-carbamoylisoxazol-5-ylmethyl[7-(5-bromopyridin-2-yl)-7-azaspiro[3.5]non-2-yl]carbamate
5. 3-carbamoylisoxazol-5-ylmethyl{7-[5-(4-fluorophenyl)pyridin-2-yl]-7-azaspiro[3.5]non-2-yl}carbamate
6. 3-carbamoylisoxazol-5-ylmethyl[7-(6-fluoroquinolin-2-yl)-7-azaspiro[3.5]non-2-yl]methylcarbamate
7. 3-(methylcarbamoyl)isoxazol-5-ylmethyl[7-(6-fluoroquinolin-2-yl)-7-azaspiro[3.5]non-2-yl]methylcarbamate
8. 3-(methylcarbamoyl)isoxazol-5-ylmethyl{7-[5-(4-fluorophenyl)pyridin-2-yl]-7-azaspiro[3.5]non-2-yl}carbamate
9. 3-(methylcarbamoyl)isoxazol-5-ylmethyl[7-(6-fluoroquinolin-2-yl)-7-azaspiro[3.5]non-2-yl]carbamate
10. 3-carbamoylisoxazol-5-ylmethyl{6-[5-(4-fluorophenyl)pyridin-2-yl]-6-azaspiro[3.4]oct-2-yl}carbamate
11. 3-(methylcarbamoyl)isoxazol-5-ylmethyl{6-[5-(4-fluorophenyl)pyridin-2-yl]-6-azaspiro[3.4]oct-2-yl}carbamate
12. 3-(methylcarbamoyl)isoxazol-5-ylmethyl{6-[5-(4-fluorophenyl)pyridin-2-yl]-6-azaspiro[3.4]oct-2-ylmethyl}carbamate (isomer I)
13. 3-(methylcarbamoyl)isoxazol-5-ylmethyl{6-[5-(4-fluorophenyl)pyridin-2-yl]-6-azaspiro[3.4]oct-2-ylmethyl}carbamate (isomer II)
14. 4-carbamoyloxazol-2-ylmethyl[7-(6-fluoroquinolin-2-yl)-7-azaspiro[3.5]non-2-yl]carbamate
15. 3-(methylcarbamoyl)isoxazol-5-ylmethyl[2-(6-fluoroquinolin-2-yl)-2-azaspiro[3.3]hept-6-yl]carbamate
16. 3-(methylcarbamoyl)isoxazol-5-ylmethyl[6-(6-fluoroquinolin-2-yl)-6-azaspiro[3.4]oct-2-ylmethyl]carbamate (one isomer)
17. 3-(methylcarbamoyl)isoxazol-5-ylmethyl{6-[5-(4-fluorophenyl)pyridin-2-yl]-6-azaspiro[3.4]oct-2-yl}carbamate (isomer I)
18. 3-(methylcarbamoyl)isoxazol-5-ylmethyl{6-[5-(4-fluorophenyl)pyridin-2-yl]-6-azaspiro[3.4]oct-2-yl}carbamate (isomer II)
19. 3-(methylcarbamoyl)isoxazol-5-ylmethyl[7-(6-chloroquinolin-2-yl)-7-azaspiro[3.5]non-2-yl]carbamate
20. 3-carbamoylisoxazol-5-ylmethyl{2-[5-(4-fluorophenyl)pyridin-2-yl]-2-azaspiro[3.3]hept-6-yl}carbamate
21. 3-methylcarbamoylisoxazol-5-ylmethyl[6-(5-bromopyridin-2-yl)-6-azaspiro[3.4]oct-2-yl]carbamate (one isomer)
22. 3-methylcarbamoylisoxazol-5-ylmethyl[6-(4-trifluoromethylpyridin-2-yl)-6-azaspiro[3.4]oct-2-yl]carbamate (one isomer)
23. 3-methylcarbamoylisoxazol-5-ylmethyl{2-[5-(4-fluorophenyl)pyridin-2-yl]-2-azaspiro[3.3]hept-6-yl}carbamate
24. 3-carbamoylisoxazol-5-ylmethyl[7-(4-trifluoromethylpyrimidin-2-yl)-7-azaspiro[3.5]non-2-yl]carbamate
25. 3-carbamoylisoxazol-5-ylmethyl{7-[6-(4-fluorophenyl)pyrazin-2-yl]-7-azaspiro[3.5]non-2-yl}carbamate
26. 3-(2-dimethylaminoethylcarbamoyl)isoxazol-5-ylmethyl[7-(4-trifluoromethylpyrimidin-2-yl)-7-azaspiro[3.5]non-2-yl]-carbamate and the hydrochloride thereof;
27. 3-carbamoylisoxazol-5-ylmethyl{7-[4-(4-fluorophenyl)pyridin-2-yl]-7-azaspiro[3.5]non-2-yl}carbamate
28. 3-carbamoylisoxazol-5-ylmethyl[7-(4-chloropyridin-2-yl)-7-azaspiro[3.5]non-2-yl]carbamate
29. 3-carbamoylisoxazol-5-ylmethyl[7-(4-trifluoromethylpyridin-2-yl)-7-azaspiro[3.5]non-2-yl]carbamate
30. 3-carbamoylisoxazol-5-ylmethyl{7-[5-(3-fluorophenyl)pyridin-2-yl]-7-azaspiro[3.5]non-2-yl}carbamate
31. 3-carbamoylisoxazol-5-ylmethyl[7-(5-isobutylpyridin-2-yl)-7-azaspiro[3.5]non-2-yl]carbamate
32. 3-carbamoylisoxazol-5-ylmethyl[7-(6-chloroquinolin-2-yl)-7-azaspiro[3.5]non-2-yl]carbamate
33. 3-methylcarbamoylisoxazol-5-ylmethyl[7-(6-chloroquinolin-2-yl)-7-azaspiro[3.5]non-2-ylmethyl]carbamate
34. 3-methylcarbamoylisoxazol-5-ylmethyl[7-(4-trifluoromethylpyridin-2-yl)-7-azaspiro[3.5]non-2-yl]carbamate
35. 3-(4-fluorophenyl)-[1,2,4]oxadiazol-5-ylmethyl[7-(4-trifluoromethylpyridin-2-yl)-7-azaspiro[3.5]non-2-yl]carbamate
36. 4-carbamoyloxazol-2-ylmethyl[7-(4-trifluoromethylpyridin-2-yl)-7-azaspiro[3.5]non-2-yl]carbamate
37. 5-methyl-3-phenylisoxazol-4-ylmethyl[7-(4-trifluoromethylpyridin-2-yl)-7-azaspiro[3.5]non-2-yl]carbamate 38. 3-ethyl[1,2,4]oxadiazol-5-ylmethyl[7-(4-trifluoromethylpyridin-2-yl)-7-azaspiro[3.5]non-2-yl]carbamate
39. 5-methyl[1,2,4]oxadiazol-3-ylmethyl[7-(4-trifluoromethylpyridin-2-yl)-7-azaspiro[3.5]non-2-yl]carbamate
40. 3-carbamoylisoxazol-5-ylmethyl[6-(4-trifluoromethylpyrimidin-2-yl)-6-azaspiro[2.5]oct-1-yl]carbamate
41. 3-methylcarbamoylisoxazol-5-ylmethyl[6-(4-trifluoromethylpyrimidin-2-yl)-6-azaspiro[2.5]oct-1-yl]carbamate.

The compounds of general formula (I) may comprise one or more asymmetric carbons. They may exist in the form of enantiomers or diastereoisomers. The compounds of general formula (I) may also exist in the form of cis or trans stereoisomers. These stereoisomers, enantiomers and diastereoisomers, and also mixtures thereof, including racemic mixtures, form part of the invention.

The compounds of formula (I) may exist in the form of bases or of acid-addition salts. Such addition salts form part of the invention.

These salts are advantageously prepared with pharmaceutically acceptable acids, but the salts of other acids that are useful, for example, for purifying or isolating the compounds of formula (I) also form part of the invention.

In the context of the invention, the following definitions apply:

alkoxy, a group —O-alkyl containing a linear or branched, saturated aliphatic chain;

thioalkyl, a group —S-alkyl containing a linear or branched, saturated aliphatic chain;

haloalkyl, an alkyl group in which one or more hydrogen atoms have been replaced with a halogen atom;

haloalkoxy, an alkoxy group in which one or more hydrogen atoms have been replaced with a halogen atom;

halothioalkyl, a thioalkyl group in which one or more hydrogen atoms have been replaced with a halogen atom;

halogen atom, a fluorine, a chlorine, a bromine or an iodine.

The compounds of the invention may be prepared according to various methods, illustrated by the schemes that follow.

Thus, a first method (scheme 1) consists in reacting an amine of general formula (II), in which A, $R_1$, $R_2$, m, n, o and p are as defined in the general formula (I) defined above, with a carbonate of general formula (III) in which Z represents a hydrogen atom or a nitro group, and $R_3$ and $R_4$ are as defined in the general formula (I) defined above, in the presence of a base such as triethylamine, pyridine, N,N-dimethylaminopyridine or diisopropylethylamine in a solvent such as toluene or dichloroethane, at a temperature between room temperature and the reflux temperature of the solvent.

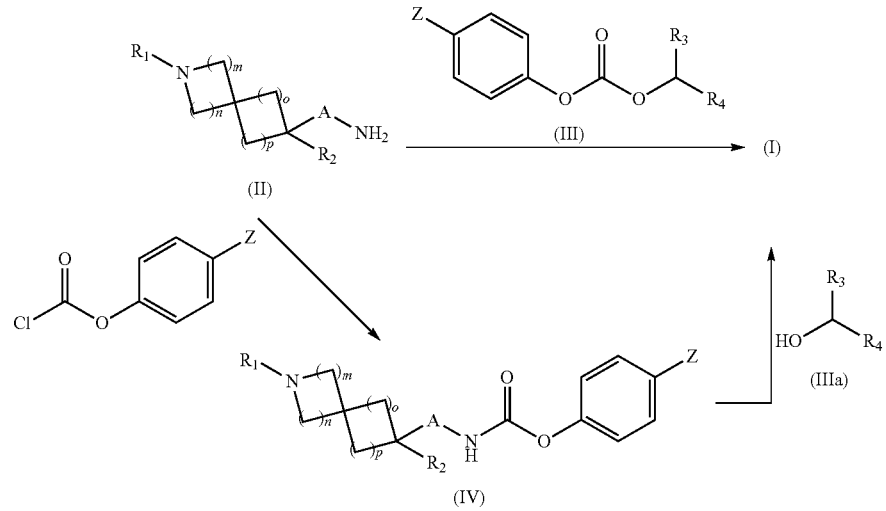

Scheme 1

$C_{t-z}$ in which t and z may take values from 1 to 8, a carbon chain possibly containing from t to z carbon atoms, for example $C_{1-3}$ is a carbon chain that may contain from 1 to 3 carbon atoms;

alkyl, a linear or branched, saturated aliphatic group; for example, a $C_{1-6}$-alkyl group represents a linear or branched carbon chain of 1 to 6 carbon atoms, more particularly a methyl, ethyl, propyl, isopropyl, butyl, isobutyl, tert-butyl, pentyl or hexyl;

alkylene, a linear or branched, saturated divalent alkyl group, for example a $C_{1-3}$-alkylene group represents a linear or branched divalent carbon chain of 1 to 3 carbon atoms, more particularly a methylene, ethylene, 1-methylethylene or propylene;

cycloalkyl, a cyclic alkyl group, for example a $C_{3-7}$-cycloalkyl group represents a cyclic carbon-based group of 3 to 7 carbon atoms, more particularly a cyclopropyl, cyclobutyl, cyclopentyl, cyclohexyl or cycloheptyl;

One variant for obtaining the compounds of general formula (I) (scheme 1) consists in reacting an amine of general formula (II), as defined above, with phenyl or 4-nitrophenyl chloroformate, in the presence of a base such as triethylamine or diisopropylethylamine, in a solvent such as dichloromethane or tetrahydrofuran, at a temperature between 0° C. and room temperature, to give the carbamate derivative of general formula (IV), in which A, $R_1$, $R_2$, m, n, o and p are as defined in the general formula (I) defined above, and Z represents a hydrogen atom or a nitro group. The carbamate derivative of general formula (IV) thus obtained is then converted into a compound of general formula (I), via the action of an alcohol of general formula $HOCHR_3R_4$ (IIIa), in which $R_3$ and $R_4$ are as defined in the general formula (I) defined above, in the presence of a base such as triethylamine, pyridine, N,N-dimethylaminopyridine or diisopropylethylamine, in a solvent such as toluene or dichloroethane, at a temperature between room temperature and the reflux temperature of the solvent.

A second method (Scheme 2-route A) consists in reacting, in a first stage, an amine of general formula (IIa), in which A, $R_2$, m, n, o and p are as defined in the general formula (I) defined above, and PG represents a protecting group such as a Boc (tert-butyloxycarbonyl), a Cbz (benzyloxycarbonyl), a benzyl or a benzhydryl, with a carbonate of general formula (III) as defined above, under the conditions described above during the reaction of the amine of general formula (II) with the carbonate of general formula (III), to obtain a compound of general formula (Ic) corresponding to the compound of formula (Ia) in which the spirane nitrogen atom is protected with a protecting group PG, followed by a deprotection reaction, for example in the presence of a solution of hydrochloric acid (5N) in isopropanol or dioxane, to obtain the intermediate of general formula (Ia), in which A, $R_2$, $R_3$, $R_4$, m, n, o and p are as defined in the general formula (I).

One variant (Scheme 2-route A variant) for obtaining the intermediates of general formula (Ia) consists in reacting an amine of general formula (IIa), as defined above, with phenyl or 4-nitrophenyl chloroformate, in the presence of a base such as triethylamine or diisopropylethylamine, in a solvent such as dichloromethane or tetrahydrofuran, at a temperature of between 0° C. and room temperature, to give the carbamate derivative of general formula (IVa), in which A, $R_2$, m, n, o and p are as defined in the general formula (I) defined above, PG is as defined above and Z represents a hydrogen atom or a nitro group. The carbamate derivative of general formula (IVa) thus obtained is then converted into a compound of general formula (Ia), via the action of an alcohol of general formula $HOCHR_3R_4$ (IIIa), as defined above, in the presence of a base such as triethylamine, pyridine, N,N-dimethylaminopyridine or diisopropylethylamine, in a solvent such as toluene or dichloroethane, at a temperature of between room temperature and the reflux temperature of the solvent, followed by a deprotection reaction, for example in the presence of a solution of hydrochloric acid (5N) in isopropanol or dioxane.

Scheme 2

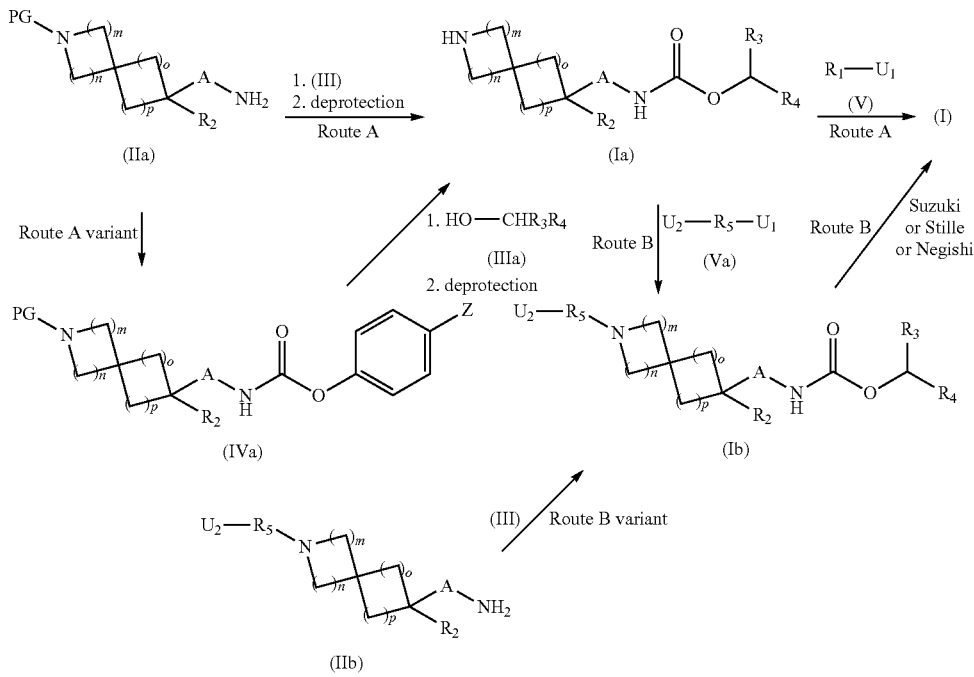

Next, according to Scheme 2, route A, the compound of general formula (I) is then obtained by reaction of the compound of general formula (Ia) with a derivative of general formula $R_1$—$U_1$ (V), in which $R_1$ is as defined in the general formula (I) and $U_1$ represents a halogen atom or an O-triflate group, using aromatic or heteroaromatic nucleophilic substitution reaction conditions, for example by means of a base such as triethylamine, diisopropylethylamine, pyridine or N,N-dimethylaminopyridine in a solvent such as dichloromethane, dichloroethane, acetonitrile, N,N-dimethylformamide, dioxane or tetrahydrofuran, at a temperature between 0° C. and the reflux temperature of the solvent. This conversion may also be performed using the Buchwald N-arylation or N-heteroarylation conditions, for example by means of a palladium or copper catalyst.

According to Scheme 2, route B, the compounds of general formula (I), in which $R_1$ represents a group $R_5$ substituted especially with a group $R_6$ of the type $C_{1-6}$-alkyl, $C_{3-7}$-cycloalkyl or $C_{3-7}$-cycloalkyl-$C_{1-3}$-alkylene, or with a group $R_7$ as defined in the general formula (I) defined above, may also be prepared according to a coupling reaction, catalysed with a transition metal, for example palladium(0), performed on the compound of general formula (Ib), in which A, $R_2$, $R_3$, $R_4$, $R_5$, m, n, o and p are as defined in the general formula (I) and $U_2$ represents a chlorine, bromine or iodine atom or a triflate group, $U_2$ being in the position in which it is desired to introduce the group $R_6$ or $R_7$:

either via a reaction of Suzuki type, for example using an alkyl, cycloalkyl, aryl or heteroaryl boronic acid, or according to a reaction of Stille type, for example using an aryl or heteroaryl trialkyltin derivative, or via a reaction of Negishi type, for example using an alkyl, cycloalkyl, aryl or heteroaryl halide zincate.

Next, according to Scheme 2 route B, the intermediate of general formula (Ib) as defined above is obtained beforehand by reacting an amine of general formula (Ia) as defined above with a derivative of general formula $U_2$—$R_5$—$U_1$ (Va), in which $R_5$, $U_1$ and $U_2$ are as defined above, using aromatic or heteroaromatic nucleophilic substitution reactions or Buchwald N-arylation or N-heteroarylation reactions, for example using a palladium or copper catalyst.

One variant for obtaining the intermediates of general formula (Ib) (Scheme 2-route B variant) consists in reacting, in a first stage, an amine of general formula (IIb), in which A, $R_5$, $R_2$, m, n, o and p are as defined in the general formula (I) defined above, and $U_2$ is as defined above, with a carbonate of general formula (III) as defined above, under the conditions described above during the reaction of the amine of general formula (II) with the carbonate of general formula (III), to obtain the intermediate of general formula (Ib), in which A, $R_5$, $R_2$, $R_3$, $R_4$, m, n, o and p are as defined in the general formula (I), and $U_2$ is as defined above.

Another subject of the present invention relates to a compound of formula (Ia) as defined above.

Another subject of the present invention relates to a compound of formula (Ic) as described above.

Another subject of the present invention relates to a compound of formula (II) as described above.

Another subject of the present invention relates to a compound of formula (IV) as described above.

The compounds of general formulae (IIa), (IIb), (III), (IIIa), (V) and (Va) and also the other reagents are commercially available or described in the literature, or may be prepared according to methods that are described therein or that are known to those skilled in the art.

In particular, the carbonate of general formula (III) may be prepared according to any method described in the literature, for example by reacting an alcohol of general formula $HOCHR_3R_4$ (IIIa), in which $R_3$ and $R_4$ are as defined in the general formula (I) as defined above, with phenyl or 4-nitrophenyl chloroformate, in the presence of a base such as triethylamine, N-methylmorpholine or diisopropylethylamine, in a solvent such as dichloromethane or tetrahydrofuran, at a temperature between 0° C. and room temperature.

The examples that follow illustrate the preparation of a number of compounds of the invention. These examples are not limiting, and serve merely to illustrate the invention. The microanalyses and the IR, NMR and/or LC-MS (liquid chromatography coupled to mass spectroscopy) spectra confirm the structures and the purities of the compounds obtained.

LC-MS Method (M+H):

UPLC/TOF—Gradient 3 min—$H_2O$/ACN/TFA T0: 98% A—T1.6 to T2.1 min: 100% B—T2.5 to T3 min: 98% A route A: $H_2O$+0.05% TFA; route B: ACN+0.035% TFA flow rate: 1.0 mL/min—T°=40° C.—Injection 2 μL Acquity BEH C18 (50×2.1 mm; 1.7 μm) column; 220 nm.

m.p. (° C.) represents the melting point in degrees Celsius.

$R_f$ indicates the retention time obtained by TLC analysis (thin-layer chromatography).

The numbers given in parentheses in the example titles correspond to those of the first column of the table hereinbelow.

The IUPAC (International Union of Pure and Applied Chemistry) nomenclature was used to name the compounds in the examples below.

EXAMPLE 1

Compound 1

Thiazol-4-ylmethyl[7-(6-fluoroquinolin-2-yl)-7-azaspiro[3.5]non-2-yl]carbamate

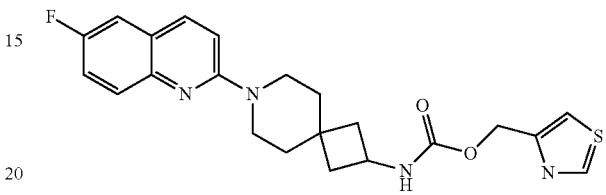

1.1. Benzyl(thiazol-4-ylmethoxycarbonylamino)-7-azaspiro[3.5]nonane-7-carboxylate A solution containing 0.32 g (1.15 mmol) of benzyl 2-amino-7-azaspiro[3.5]nonane-7-carboxylate (WO92/22550), 0.36 g (1.26 mmol) of thiazol-4-ylmethyl 4-nitrophenyl carbonate (WO 2008/013834), 0.45 g (3.44 mmol) of N,N-diisopropylethylamine and 0.014 g (0.11 mmol) of N,N-dimethylaminopyridine in 5 mL of dichloromethane is heated at 50° C. for 2 hours.

Water is added to the reaction medium, the aqueous phase is separated out and extracted several times with dichloromethane, and the combined organic phases are washed with aqueous sodium hydroxide solution (1N) and then with saturated aqueous ammonium chloride solution. The resulting phase is dried over sodium sulfate and the filtrate is concentrated under reduced pressure.

After evaporating off the solvent, the residue obtained is purified by chromatography on silica gel, eluting with a 95/5 mixture of dichloromethane and methanol.

0.345 g of pure product is thus obtained the form of a white powder.

LC-MS: M+H=416 m.p. (° C.): 91-93° C.

$^1$H NMR (DMSO) δ (ppm): 8.80 (s, 1H); 7.50-7.30 (m, 6H); 5.30 (s, 2H); 5.15 (s, 2H); 4.90 (broad s, 1H); 4.15 (m, 1H); 3.50 (m, 2H); 3.30 (m, 2H); 2.30 (t, 2H); 1.70-1.40 (m, 6H).

1.2. Thiazol-4-ylmethyl(7-azaspiro[3.5]non-2-yl) carbamate 1.22 mL (6.98 mmol) of a 5.7N solution of hydrobromic acid in acetic acid are added slowly to a solution of 0.29 g (0.70 mmol) of benzyl(thiazol-4-ylmethoxycarbonylamino)-7-azaspiro[3.5]nonane-7-carboxylate, obtained in step 1.1., in 1 mL of acetic acid, cooled by means of an ice/water bath. Stirring is continued at room temperature for 1 hour.

After evaporation under reduced pressure, the residue is taken up in water and basified with aqueous sodium hydroxide solution (30%). The resulting mixture is extracted several times with dichloromethane and the combined organic phases are then dried over sodium sulfate, and the filtrate is concentrated under reduced pressure. 0.138 g of product is obtained in the form of a colourless oil, which is used without further purification in the following step.

$^1$H NMR (CDCl$_3$) δ (ppm): 8.80 (s, 1H); 7.30 (s, 1H); 5.20 (s, 2H); 4.80 (m, 1H); 4.50 (broad s, 1H); 4.00 (m, 1H); 2.90-2.70 (m, 3H); 2.40-2.10 (m, 3H); 1.70-1.40 (m, 6H).

1.3. Thiazol-4-ylmethyl[7-(6-fluoroquinolin-2-yl)-7-azaspiro[3.5]non-2-yl]carbamate 0.135 g (0.48 mmol) of thiazol-4-ylmethyl(7-azaspiro[3.5]non-2-yl)carbamate, obtained in step 1.2., 0.141 g (0.62 mmol) of 2-bromo-6-fluoroquinoline and 0.186 g (1.44 mmol) of N,N-diisopropylethylamine are placed in a sealed tube in 1.5 mL of acetonitrile. The mixture is then heated at 100° C. for 12 hours. The reaction medium is allowed to cool to room temperature and is then taken up in ethyl acetate, the aqueous phase is separated out and extracted twice with ethyl acetate, and the combined organic phases are washed with saturated aqueous ammonium chloride solution and dried over sodium sulfate. After evaporating off the solvent, the residue obtained is purified by chromatography on preparative plates, eluting with a 95/5/0.5 mixture of dichloromethane, methanol and 28% aqueous ammonia.

0.100 g of pure product is thus obtained in the form of a white powder.

LC-MS: M+H=427 m.p. (° C.): 107-109° C.

$^1$H NMR (DMSO) δ (ppm): 8.80 (s, 1H); 7.80 (d, 1H); 7.60 (m, 1H); 7.35 (s, 1H); 7.30-7.15 (m, 2H); 7.00 (d, 1H); 5.30 (s, 2H); 4.90 (broad s, 1H); 4.20 (m, 1H); 3.70-3.50 (m, 4H); 2.35 (t, 2H); 1.80-1.60 (m, 6H).

EXAMPLE 2

Compound 5

3-Carbamoylisoxazol-5-ylmethyl{7-[5-(4-fluorophenyl)pyridin-2-yl]-7-azaspiro[3.5]non-2-yl}carbamate

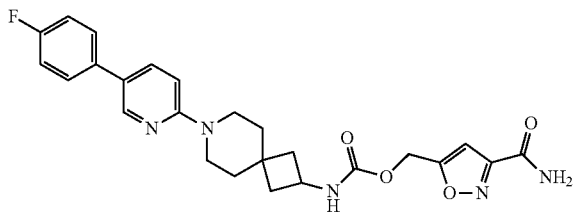 [SMILES: NC(=O)c1cc(COC(=O)NC2CC3(CCN(c4ccc(-c5ccc(F)cc5)cn4)CC3)C2)on1]

2.1. tert-Butyl 2-azido-7-azaspiro[3.5]nonane-7-carboxylate

A solution of 5.90 g (18.47 mmol) of tert-butyl 2-methanesulfonyloxy-7-azaspiro[3.5]nonane-7-carboxylate (WO 2003/084 948) and 3.60 g (55.41 mmol) of sodium azide in 27 mL of N,N-dimethylformamide is refluxed for 12 hours under an inert atmosphere.

The reaction medium is allowed to cool to room temperature and is then taken up in dichloromethane and water, the aqueous phase is separated out and extracted twice with dichloromethane, and the combined organic phases are washed with saturated aqueous sodium chloride solution and dried over sodium sulfate. After evaporating off the solvent, 4.78 g of product are obtained in the form of an orange oil, which is used without further purification in the following step.

$^1$H NMR (CDCl$_3$) δ (ppm): 3.80 (m, 1H); 3.20 (m, 4H); 2.30-2.10 (m, 2H); 1.90-1.70 (m, 2H); 1.50 (m, 4H); 1.35 (s, 9H).

2.2. tert-Butyl 2-amino-7-azaspiro[3.5]nonane-7-carboxylate 1.85 g (8.97 mmol) of Lindlar catalyst (PdCaCO$_3$) are added to a solution of 4.78 g (17.95 mmol) of tert-butyl 2-azido-7-azaspiro[3.5]nonane-7-carboxylate, obtained in step 2.1., in 70 mL of ethanol. The reaction medium is placed in a Parr flask under a hydrogen atmosphere (20 psi) at room temperature for 5 hours. The resulting mixture is filtered through Celite and the filtrate is then concentrated under reduced pressure. Water and dichloromethane are added. The aqueous phase is separated out and then extracted three times with dichloromethane, and the combined organic phases are washed with saturated aqueous sodium chloride solution and dried over sodium sulfate. After evaporating off the solvent, 3.62 g of product are obtained in the form of an oil, which is used without further purification in the following step.

$^1$H NMR (DMSO) δ (ppm): 3.40 (m, 1H); 3.30-3.10 (m, 4H); 2.25-2.15 (m, 2H); 1.70 (broad s, 2H); 1.50-1.35 (m, 6H); 1.30 (m, 9H).

2.3. tert-Butyl 2-(4-nitrophenoxycarbonylamino)-7-azaspiro[3.5]nonane-7-carboxylate 0.922 g (4.58 mmol) of 4-nitrophenyl chloro formate is added portionwise to a solution of 1.00 g (4.16 mmol) of tert-butyl 2-amino-7-azaspiro[3.5]nonane-7-carboxylate, prepared in step 2.2., 1.34 g (10.40 mmol) of N,N-diisopropylethylamine and 0.05 g (0.42 mmol) of N,N-dimethylaminopyridine in 40 mL of dichloromethane, cooled to about 0° C. Stirring is continued at 0° C. for 3 hours and then at room temperature for 3 hours. Water is added to the reaction medium, the aqueous phase is separated out and extracted several times with dichloromethane, the combined organic phases are washed with saturated aqueous ammonium chloride solution and then with saturated aqueous sodium chloride solution and dried over sodium sulfate, and the filtrate is concentrated under reduced pressure. 1.8 g of product are thus obtained in the form of an amorphous beige-coloured solid, which is used without further purification in the following step.

$^1$H NMR (CDCl$_3$) δ (ppm): 8.20 (d, 2H); 7.30 (d, 2H); 5.30 (broad s, 1H); 4.10 (m, 1H); 3.25 (m, 4H); 2.30-2.10 (m, 2H); 1.70 (m, 2H); 1.50 (m, 4H); 1.40 (s, 9H).

2.4. tert-Butyl 2-(3-carbamoylisoxazol-5-ylmethoxycarbonylamino)-7-azaspiro[3.5]nonane-7-carboxylate A solution of 1.70 g (4.19 mmol) of tort-butyl 2-(4-nitrophenoxycarbonylamino)-7-azaspiro[3.5]nonane-7-carboxylate, prepared in step 2.3., 1.08 g (8.39 mmol) of N,N-diisopropylethylamine, 0.033 g (0.27 mmol) of N,N-dimethylaminopyridine and 0.05 g (0.42 mmol) of 3-carbamoylisoxazol-5-ylmethanol in 20 mL of 1,2-dichloroethane is heated in a sealed tube at 90° C. for 12 hours. The reaction medium is allowed to cool to room temperature, water is added, the aqueous phase is separated out and extracted several times with dichloromethane, and the combined organic phases are washed with aqueous sodium hydroxide solution (1N) and then with saturated aqueous ammonium chloride solution and dried over sodium sulfate, and the filtrate is concentrated under reduced pressure. The oil obtained is crystallized from ether and the solid thus obtained is filtered off and then rinsed thoroughly with ether.

After drying under vacuum at about 40° C., 0.910 g of pure product is obtained in the form of a white powder.

LC-MS: M+H=409 m.p. (° C.): 123-125° C.

$^1$H NMR (DMSO) δ (ppm): 8.15 (broad s, 1H); 7.80 (broad s, 1H); 7.70 (d, 1H); 6.80 (s, 1H); 5.20 (s, 2H); 4.00 (m, 1H); 3.30-3.10 (m, 4H); 2.10 (m, 2H); 1.85 (m, 2H); 1.50 (m, 2H); 1.40 (s, 9H); 1.30 (m, 2H).

2.5. 3-Carbamoylisoxazol-5-ylmethyl(7-azaspiro[3.5]non-2-yl)carbamate hydrochloride 8 mL (32 mmol) of a 4N solution of hydrochloric acid in dioxane are added slowly to a solution of 0.87 g (2.13 mmol) of tert-butyl 2-(3-carbamoylisoxazol-5-ylmethoxycarbonylamino)-7-azaspiro[3.5]nonane-7-carboxylate, obtained in step 2.4., in 2 mL of dioxane, cooled by means of an ice/water bath. Stirring is continued at room temperature for 12 hours. After evaporation under reduced pressure, 0.77 g of product is obtained in hydrochloride form, which is used without further purification in the following step.

$^1$H NMR (D$_2$O) δ (ppm): 6.80 (s, 1H); 5.20 (s, 2H); 4.00 (m, 1H); 3.10 (m, 4H); 2.20 (m, 2H); 1.80 (m, 6H).

2.6. 3-Carbamoylisoxazol-5-ylmethyl[7-(5-bromopyridin-2-yl)-7-azaspiro[3.5]non-2-yl]carbamate 0.265 g (1.51 mmol) of 5-bromo-2-fluoropyridine, 0.40 g (1.16 mmol) of 3-carbamoylisoxazol-5-ylmethyl(7-azaspiro[3.5]non-2-yl)carbamate hydrochloride, prepared in step 2.5., and 0.60 g (4.64 mmol) of N,N-diisopropylethylamine in 3.5 mL of acetonitrile are placed in a sealed tube. 2 mL of DMF are added and the mixture is then heated at 100° C. for 12 hours. The reaction mixture is allowed to cool to room temperature and is then taken up in dichloromethane and water. The aqueous phase is separated out and extracted twice with dichloromethane, and the combined organic phases are washed with saturated aqueous ammonium chloride solution and then with saturated aqueous sodium chloride solution and dried over sodium sulfate, and the filtrate is concentrated under reduced pressure. The oil obtained is triturated in diisopropyl ether. The solid thus obtained is filtered off and then rinsed thoroughly with ether. After drying under vacuum at about 40° C., 0.195 g of pure product is obtained in the form of a beige-coloured powder.

LC-MS: M+H=465 m.p. (° C.): 165-167° C.

$^1$H NMR (DMSO) δ (ppm): 8.10 (s, 2H); 7.80 (s, 1H); 7.70 (d, 1H); 7.60 (d, 1H); 6.85 (d, 1H); 6.75 (s, 1H); 5.20 (s, 2H); 4.00 (m, 1H); 3.55 (t, 2H); 3.45 (t, 2H); 2.20 (m, 2H); 1.75 (m; 2H); 1.65-1.45 (m, 4H).

2.7. 3-Carbamoylisoxazol-5-ylmethyl{7-[5-(4-fluorophenyl)pyridin-2-yl]-7-azaspiro[3.5]non-2-yl}carbamate 0.160 g (0.34 mmol) of 3-carbamoylisoxazol-5-ylmethyl[7-(5-bromopyridin-2-yl)-7-azaspiro[3.5]non-2-yl]carbamate, obtained in step 2.6., 0.058 g (0.41 mmol) of 4-fluorophenylboronic acid, and 0.349 g (1.03 mmol) of caesium carbonate suspended in 3 mL of a 9/1 mixture of tetrahydrofuran and water are placed under an inert atmosphere. 0.028 g (0.03 mmol) of PdCl$_2$dppf.CH$_2$Cl$_2$ is then added. The mixture is then heated at about 75° C. for 12 hours. The resulting mixture is allowed to cool to room temperature, the salts are separated out by filtration on Celite, and the filtrate is then taken up in dichloromethane and water. The aqueous phase is separated out and extracted twice with dichloromethane, and the combined organic phases are washed with saturated aqueous sodium chloride solution and dried over sodium sulfate.

After evaporating off the solvent, the residue obtained is purified by chromatography on preparative plates, eluting with a 90/10/1 mixture of dichloromethane/methanol and 28% aqueous ammonia.

0.084 g of pure product is thus obtained in the form of a white powder.

LC-MS: M+H=480 m.p. (° C.): 216-218° C.

$^1$H NMR (DMSO) δ (ppm): 8.40 (s, 1H); 8.20 (broad s, 1H); 7.90-7.70 (m, 3H); 7.60 (m, 2H); 7.25 (m, 2H); 6.90 (d, 1H); 6.75 (s, 1H); 5.20 (s, 2H); 4.00 (m, 1H); 3.55 (t, 2H); 3.45 (t, 2H); 2.20 (m, 2H); 1.75 (m; 2H); 1.65-1.45 (m, 4H).

EXAMPLE 3

Compound 2

3-Carbamoylisoxazol-5-ylmethyl[7-(6-fluoroquinolin-2-yl)-7-azaspiro[3.5]non-2-yl]carbamate

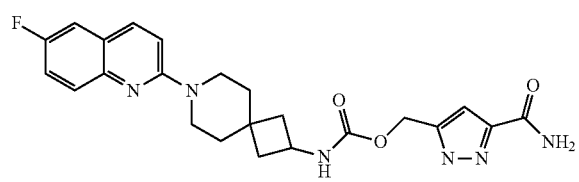 [SMILES: NC(=O)c1cc(COC(=O)NC2CC3(CCN(c4ccc5cc(F)ccc5n4)CC3)C2)[nH]n1]

The process is performed according to the procedure described in Example 2 (step 2.6.). Starting with 0.20 g (0.58 mmol) of 3-carbamoylisoxazol-5-ylmethyl(7-azaspiro[3.5]non-2-yl)carbamate hydrochloride, described in Example 2 (step 2.5.), 0.170 g (0.75 mmol) of 2-bromo-6-fluoroquinoline and 0.30 g (2.32 mmol) of N,N-diisopropylethylamine, and after chromatography on preparative plates, eluting with a 90/10/1 mixture of dichloromethane, methanol and 28% aqueous ammonia, 0.05 g of pure product is obtained in the form of a white powder.

LC-MS: M+H=455 m.p. (° C.): 226-228° C.

$^1$H NMR (DMSO) δ (ppm): 8.15 (broad s, 1H); 8.00 (d, 1H); 7.85 (broad s, 1H); 7.70 (d, 1H); 7.60 (m, 1H); 7.50 (m, 1H); 7.40 (m, 1H); 7.30 (d, 1H); 6.70 (s, 1H); 5.20 (s, 2H); 4.10 (m, 1H); 3.70-3.50 (m, 4H); 2.35 (t, 2H); 1.80 (t, 2H); 1.70-1.40 (m, 4H).

EXAMPLE 4

Compound 9

3-(Methylcarbamoyl)isoxazol-5-ylmethyl[7-(6-fluoroquinolin-2-yl)-7-azaspiro[3.5]non-2-yl]carbamate

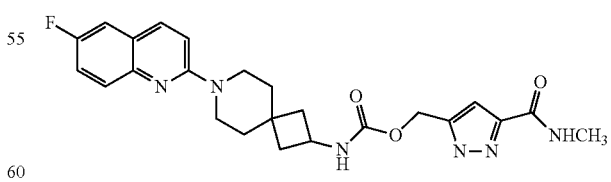

4.1. 3-(Methylcarbamoyl)isoxazol-5-ylmethyl 4-nitrophenylcarbonate 2.58 g (12.81 mmol) of 4-nitrophenyl chloroformate are added portionwise to a solution of 2.00 g (12.81 mmol) of 3-(methylcarbamoyl)isoxazol-5-ylmethanol, 1.52 g (19.21 mmol) of pyridine and 0.157 g (1.28 mmol) of N,N-dimethylaminopyridine, in 15 mL of dichloromethane, cooled to about 0° C. Stirring is continued at 0° C. for 1 hour and then at room temperature for 1 hour. The precipitate thus formed is filtered off and then rinsed thoroughly with diisopropyl ether. After drying under vacuum at about 60° C., 2.60 g of product are obtained in the form of a white powder, which is used without further purification in the following step.

$^1$H NMR (CDCl$_3$) δ (ppm): 8.40 (d, 2H); 7.50 (d, 2H); 7.0 (s, 1H); 6.90 (broad s, 1H); 5.50 (s, 2H); 3.10 (d, 3H).

4.2. tert-Butyl 2-[3-(methylcarbamoyl)isoxazol-5-ylmethoxycarbonylamino]-7-azaspiro[3.5]nonane-7-carboxylate The process is performed according to the procedure described in Example 1, step 1.1. Starting with 0.3 g (1.25 mmol) of ter-butyl 2-amino-7-azaspiro[3.5]nonane-7-carboxylate, described in Example 2 (step 2.2.), 0.481 g (1.50 mmol) of 4-3-(methylcarbamoyl)isoxazol-5-ylmethyl nitrophenyl carbonate, obtained in step 4.1., 0.403 g (3.12 mmol) of N,N-diisopropylethylamine and 0.076 g (0.62 mmol) of N,N-dimethylaminopyridine, and after precipitating with ether and filtration, 0.364 g of product is obtained in the form of an amorphous beige-coloured solid, which is used without further purification in the following step.

LC-MS: M+H=423

$^1$H NMR (DMSO) δ (ppm): 8.80 (broad s, 1H); 7.80 (d, 1H); 6.80 (d, 1H); 5.20 (s, 2H); 4.00 (m, 1H); 3.30-3.10 (m, 4H); 2.80 (s, 3H); 2.10 (m, 2H); 1.70 (m, 2H); 1.50 (m, 2H); 1.40 (s, 9H); 1.30 (m, 2H).

4.3. 3-(Methylcarbamoyl)isoxazol-5-ylmethyl(7-azaspiro[3.5]non-2-yl)carbamate hydrochloride The process is performed according to the procedure described in Example 2, step 2.5. Starting with 0.364 g (0.86 mmol) of tert-butyl 2-[3-(methylcarbamoyl)isoxazol-5-ylmethoxycarbonylamino]-7-azaspiro[3.5]nonane-7-carboxylate, obtained in step 4.2., and 3.25 mL (12.92 mmol) of a 4N solution of hydrochloric acid in dioxane, 0.32 g of product is obtained in hydrochloride form, which is used without further purification in the following step.

LC-MS: M+H=359

$^1$H NMR (DMSO) δ (ppm): 8.80 (broad s, 2H); 7.80 (d, 1H); 6.80 (s, 1H); 5.20 (s, 2H); 4.0 (m, 1H); 3.00-2.85 (m, 4H); 2.75 (s, 3H); 2.20 (m, 2H); 1.70 (m, 4H); 1.60 (m, 2H).

4.4. 3-(Methylcarbamoyl)isoxazol-5-ylmethyl[7-(6-fluoroquinolin-2-yl)-7-azaspiro[3.5]non-2-yl]carbamate The process is performed according to the procedure described in Example 1 (step 1.3.). Starting with 0.163 g (0.45 mmol) of 3-(methylcarbamoyl)isoxazol-5-ylmethyl(7-azaspiro[3.5]non-2-yl)carbamate hydrochloride, obtained in step 4.3., 0.133 g (0.59 mmol) of 2-bromo-6-fluoroquinoline and 0.234 g (1.82 mmol) of N,N-diisopropylethylamine, and after purification by chromatography on preparative plates, eluting with a 92.5/7.5/0.75 mixture of dichloromethane, methanol and 28% aqueous ammonia, 0.068 g of pure product is obtained in the form of a white powder.

LC-MS: M+H=468 m.p. (° C.): 193-195° C.

$^1$H NMR (DMSO) δ (ppm): 8.70 (broad s, 1H); 8.00 (d, 1H); 7.85 (d, 1H); 7.70 (m, 1H); 7.60 (m, 1H); 7.50 (m, 1H); 7.40 (m, 1H); 6.80 (s, 1H); 5.20 (s, 2H); 4.10 (m, 1H); 3.70-3.50 (m, 4H); 2.80 (s, 3H); 2.20 (t, 2H); 1.70 (t, 2H); 1.70-1.50 (m, 4H).

EXAMPLE 5

Compound 6

3-Carbamoylisoxazol-5-ylmethyl[7-(6-fluoroquinolin-2-yl)-7-azaspiro[3.5]non-2-yl]methylcarbamate

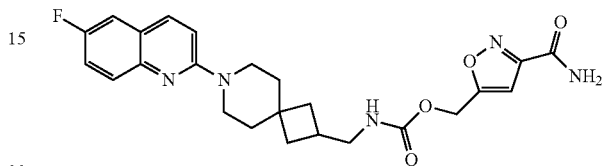

5.1. tert-Butyl 2-(aminomethyl)-7-azaspiro[3.5]nonane-7-carboxylate

To a solution of 1.40 g (5.59 mmol) of tert-butyl 2-cyano-7-azaspiro[3.5]nonane-7-carboxylate (*Chem. Pharm. Bull.;* 52 (6), 675-687, 2004), in 10 mL of a 1N solution of sodium hydroxide in ethanol. 0.164 g (2.80 mmol) of Raney nickel is then added. The reaction medium is placed in a Parr flask under a hydrogen atmosphere (60 psi) at room temperature for 2 hours. The resulting mixture is filtered through a Büchner funnel and the filtrate is then concentrated under reduced pressure. Dichloromethane is added, the aqueous phase is separated out and extracted three times with dichloromethane, and the combined organic phases are washed with saturated aqueous sodium chloride solution and dried over sodium sulfate. After evaporating off the solvent, 1.212 g of product are obtained in the form of a colourless oil, which is used without further purification in the following step.

LC-MS: M+H=255

$^1$H NMR (DMSO) δ (ppm): 3.30-3.10 (m, 4H); 2.50 (d, 2H); 2.10 (m, 1H); 1.80 (m, 2H); 1.40 (m, 2H); 1.30 (m, 13H).

5.2. tert-Butyl 2-[(4-nitrophenoxycarbonylamino)methyl]-7-azaspiro[3.5]nonane-7-carboxylate The process is performed according to the procedure described in Example 2 (step 2.3.). Starting with 1.10 g (4.32 mmol) of tert-butyl 2-aminomethyl-7-azaspiro[3.5]nonane-7-carboxylate, prepared in step 5.1., 1.40 g (10.81 mmol) of N,N-diisopropylethylamine, 0.053 g (0.43 mmol) of N,N-dimethylaminopyridine and 0.959 g (4.76 mmol) of 4-nitrophenyl chloroformate, 1.8 g of product are obtained in the form of a yellow oil, which is used without further purification in the following step.

5.3. tert-Butyl 2-[(3-carbamoylisoxazol-5-ylmethoxycarbonylamino)methyl]-7-azaspiro[3.5]nonane-7-carboxylate The process is performed according to the procedure described in Example 2 (step 2.4.). Starting with 0.50 g (1.19 mmol) of tert-butyl 2-[(4-nitrophenoxycarbonylamino)methyl]-7-azaspiro[3.5]nonane-7-carboxylate, prepared in step 5.2., 0.337 g (2.38 mmol) of N,N-diisopropylethylamine, 0.073 g (0.60 mmol) of N,N-dimethylaminopyridine and 0.169 g (1.19 mmol) of 3-carbamoylisoxazol-5-ylmethanol, 0.50 g of product is obtained in the form of an oil, which is used without further purification in the following step.

5.4. 3-Carbamoylisoxazol-5-ylmethyl(7-azaspiro[3.5]non-2-ylmethyl)carbamate hydrochloride The process is performed according to the procedure described in Example 2, step 2.5. Starting with 0.50 g (1.18 mmol) of tert-butyl 2-[(3-carbamoylisoxazol-5-ylmethoxycarbonylamino)methyl]-7-azaspiro[3.5]nonane-7-carboxylate, obtained in step 5.3., and 2.96 mL (11.83 mmol) of a 4N solution of hydrochloric acid in dioxane, 0.309 g of product is obtained in hydrochloride form, which is used without further purification in the following step.

LC-MS: M+H=359
m.p. (° C.): 120-122
$^1$H NMR (DMSO) δ (ppm): 8.10 (broad s, 1H); 7.80 (broad s, 1H); 7.50 (broad s, 1H); 6.80 (s, 1H); 5.20 (s, 2H); 3.10 (m, 2H); 2.90 (m, 2H); 2.80 (m, 2H); 2.40 (m, 1H); 1.90 (t, 2H); 1.75 (m, 2H); 1.60 (m, 2H); 1.50 (t, 3H).

5.5. 3-Carbamoylisoxazol-5-ylmethyl[7-(6-fluoroquinolin-2-yl)-7-azaspiro[3.5]non-2-yl]methylcarbamate The process is performed according to the procedure described in Example 1 (step 1.3.). Starting with 0.167 g (0.47 mmol) of 3-carbamoylisoxazol-5-ylmethyl(7-azaspiro[3.5]non-2-ylmethyl)carbamate hydrochloride, described in step 5.4., 0.137 g (0.60 mmol) of 2-bromo-6-fluoroquinoline and 0.180 g (1.40 mmol) of N,N-diisopropylethylamine, and after purification by chromatography on preparative plates, eluting with a 90/10/1 mixture of dichloromethane, methanol and 28% aqueous ammonia, 0.05 g of pure product is obtained in the form of a white powder.

LC-MS: M+H=468
m.p. (° C.): 190-192° C.
$^1$H NMR (DMSO) δ (ppm): 8.15 (broad s, 1H); 8.0 (d, 1H); 7.85 (broad s, 1H); 7.60-7.35 (m, 4H); 7.25 (d, 1H); 6.75 (s, 1H); 5.20 (s, 2H); 3.70 (t, 2H); 3.60 (t, 2H); 3.10 (t, 2H); 2.40 (m, 1H); 1.90 (t, 2H); 1.70 (m, 2H); 1.60 (m, 4H).

EXAMPLE 6

Compound 10

3-Carbamoylisoxazol-5-ylmethyl{6-[5-(4-fluorophenyl)pyridin-2-yl]-6-azaspiro[3.4]oct-2-yl}carbamate (Mixture of Isomers)

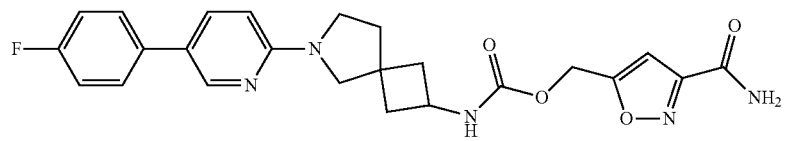 [SMILES: NC(=O)c1cc(COC(=O)NC2CC3(CCN(c4ccc(-c5ccc(F)cc5)cn4)C3)C2)on1]

6.1. tert-Butyl 2-hydroxy-6-azaspiro[3.4]octane-6-carboxylate 0.89 g (23.57 mmol) of sodium borohydride is added portionwise at 0° C. to a solution of 3.54 g (15.71 mmol) of tert-butyl 2-oxo-6-azaspiro[3.4]octane-6-carboxylate (WO98/06720) diluted in 40 mL of methanol. The reaction mixture is stirred at room temperature for 1 hour 30 minutes. After evaporating off the solvent, water is added to the reaction medium, the aqueous phase is separated out and extracted several times with diethyl ether, the combined organic phases are washed with saturated aqueous sodium chloride solution and dried over sodium sulfate, and the filtrate is concentrated under reduced pressure. After evaporating off the solvent, 3.10 g of product are obtained in the form of a brown oil, which is used without further purification in the following step.

$^1$H NMR (DMSO) δ (ppm): 4.7 (t, 1H); 4.1 (m, 1H); 3.2 (m, 4H); 2.2 (m, 2H); 1.8 (m, 4H); 1.4 (s, 9H).

6.2. tert-Butyl 2-methanesulfonyloxy-6-azaspiro[3.4]octane-6-carboxylate 0.76 mL (5.49 mmol) of triethylamine and then 0.43 mL (5.49 mmol) of mesyl chloride are added to a solution of 1.52 g (4.99 mmol) of tert-butyl 2-hydroxy-6-azaspiro[3.4]octane-6-carboxylate, obtained in step 6.1., in 45 mL of dichloromethane. The reaction medium is stirred at room temperature for 1 hour 30 minutes. After evaporating off the solvent, water is added to the reaction medium, the aqueous phase is separated out and extracted several times with dichloromethane, the combined organic phases are washed with saturated aqueous sodium chloride solution and dried over sodium sulfate, and the filtrate is concentrated under reduced pressure. After evaporating off the solvent, 1.90 g of product are obtained in the form of a brown oil, which is used without further purification in the following step.

6.3. tert-Butyl 2-azido-6-azaspiro[3.4]octane-6-carboxylate

A solution of 0.46 g (1.51 mmol) of tert-butyl 2-methanesulfonyloxy-6-azaspiro[3.4]octane-6-carboxylate, prepared in step 6.2., and 0.19 g (3.01 mmol) of sodium azide in 5 mL of N,N-dimethylformamide is refluxed for 12 hours under an inert atmosphere. The reaction medium is allowed to cool to room temperature and is then taken up in ethyl acetate and water. The aqueous phase is separated out and extracted twice with ethyl acetate, and the combined organic phases are washed with saturated aqueous ammonium chloride solution and dried over sodium sulfate. After evaporating off the solvent, 0.380 g of product is obtained in the form of an orange-coloured oil, which is used without further purification in the following step.

$^1$H NMR (DMSO) δ (ppm): 4.0 (m, 1H); 3.4 (m, 4H); 2.4 (m, 2H); 2.2 (m, 2H); 1.9 (m, 2H); 1.5 (s, 9H).

6.4. tert-Butyl 2-amino-6-azaspiro[3.4]octane-6-carboxylate 1.50 g (7.27 mmol) of Lindlar catalyst (PdCaCO$_3$) are added to a solution of 3.67 g (14.54 mmol) of tert-butyl 2-azido-6-azaspiro[3.4]octane-6-carboxylate, obtained in step 6.3., in 60 mL of ethanol. The reaction medium is placed in a Parr flask under a hydrogen atmosphere at 20 psi, at room temperature for 5 hours. The resulting mixture is filtered through Celite and the filtrate is then concentrated under reduced pressure. After evaporating off the solvent, the residue obtained is purified by chromatography on silica gel, eluting with a 95/5/0.5 mixture of dichloromethane, methanol and 28% aqueous ammonia.

1.57 g of pure product are thus obtained in the form of a brown oil.

$^1$H NMR (DMSO) δ (ppm): 3.35 (m, 1H); 3.25-3.10 (m, 4H); 2.2 (m, 2H); 1.80 (t, 2H); 1.6 (m, 2H); 1.4 (s, 9H).

6.5. tert-Butyl 2-(3-carbamoylisoxazol-5-ylmethoxycarbonylamino)-6-azaspiro[3.4]octane-6-carboxylate A solution of 0.304 g (1.51 mmol) of 4-nitrophenyl chloroformate dissolved in 5 mL of 1,2-dichloroethane is added dropwise to a solution containing 0.284 g (1.66 mmol) of ethyl 5-hydroxymethylisoxazole-3-carboxylate and 0.39 g (3.02 mmol) of N,N-diisopropylethylamine in 10 mL of 1,2-dichloroethane, cooled to about 0° C. Stirring is continued at 0° C. for 1 hour and then at room temperature for 1 hour. 0.39 g (3.02 mmol) of N,N-diisopropylethylamine and then 0.34 g (1.51 mmol) of tert-butyl 2-amino-6-azaspiro[3.4]octane-6-carboxylate, prepared in step 6.4., are added. The reaction medium is stirred at 70° C. for 4 hours. It is allowed to cool to room temperature. Water is added to the reaction medium, the aqueous phase is separated out and extracted several times with dichloromethane, the combined organic phases are washed with aqueous sodium hydroxide solution (1N) and then with saturated aqueous ammonium chloride solution and dried over sodium sulfate, and the filtrate is concentrated under reduced pressure. 0.44 g of pure product is thus obtained in the form of an orange oil, which is used without further purification in the following step.

LC-MS: M+H=424

$^1$H NMR (DMSO) δ (ppm): 7.80 (broad s, 1H); 6.90 (s, 1H); 5.20 (s, 2H); 4.40 (q, 2H) 4.00 (m, 1H); 3.40-3.10 (m, 4H); 2.30 (m, 2H); 2.00-1.70 (m, 4H); 1.40 (s, 9H); 1.30 (t, 3H).

6.6. Ethyl 5-(6-azaspiro[3.4]oct-2-ylcarbamoyloxymethyl)isoxazole-3-carboxylate trifluoroacetate 0.88 mL (10.39 mmol) of a solution of trifluoroacetic acid is added slowly to a solution of 0.44 g (1.04 mmol) of tert-butyl 2-(3-carbamoylisoxazol-5-ylmethoxycarbonylamino)-6-azaspiro[3.4]octane-6-carboxylate, obtained in step 6.5., in 10 mL of dichloromethane, cooled by means of an ice/water bath. Stirring is continued at room temperature for 4 hours.

After evaporation under reduced pressure, 0.45 g of product in trifluoroacetate form is obtained, which is used without further purification in step 6.8. below.

6.7. 2-Fluoro-5-(4-fluorophenyl)pyridine 2.51 g (14.29 mmol) of 4-fluorophenylboronic acid, 0.825 g (0.71 mmol) of Pd(PPh$_3$)$_4$ and 50 mL of 1M sodium carbonate solution are added to a solution of 2.0 g (14.29 mmol) of 5-bromo-2-fluoropyridine in 140 mL of a 4/1 mixture of toluene and ethanol. The mixture is stirred at 90° C. for 2 hours.

The resulting mixture is allowed to cool to room temperature. It is extracted several times with ethyl acetate. The organic phases are then dried over sodium sulfate and evaporated to dryness. 2.3 g of pure product are obtained in the form of a white powder.

m.p. (° C.): 98-100

$^1$H NMR (DMSO) δ (ppm): 8.55 (m, 1H), 8.28 (dd, 1H), 7.78 (m, 2H), 7.54 (m, 2H), 7.28 (dd, 1H).

6.8. Ethyl 5-{6-[5-(4-fluorophenyl)pyridin-2-yl]-6-azaspiro[3.4]oct-2-ylcarbamoyloxymethyl}-isoxazole-3-carboxylate The process is performed according to the procedure described in Example 1 (step 1.3.). Starting with 0.45 g (1.04 mmol) of ethyl 5-(6-azaspiro[3.4]oct-2-ylcarbamoyloxymethyl)isoxazole-3-carboxylate trifluoroacetate, described in step 6.6., 0.198 g (1.04 mmol) of 2-fluoro-5-(4-fluorophenyl) pyridine, prepared in step 6.7. and 0.40 g (3.12 mmol) of N,N-diisopropylethylamine, and after purification by chromatography on preparative plates, eluting with a 96/4 mixture of dichloromethane and methanol, 0.10 g of pure product is obtained in the form of a wax, which is used without further purification in the following step.

6.9. 3-Carbamoylisoxazol-5-ylmethyl{6-[5-(4-fluorophenyl)pyridin-2-yl]-6-azaspiro[3.4]oct-2-yl}carbamate In a sealed tube, a solution of 0.045 g (0.09 mmol) of ethyl 5-{6-[5-(4-fluorophenyl)pyridin-2-yl]-6-azaspiro[3.4]oct-2-ylcarbamoyloxymethyl}isoxazole-3-carboxylate, prepared in step 6.8., in 1.3 mL (9.10 mmol) of a solution (7M) of ammonia in methanol, is stirred at 70° C. for 2 hours.

The mixture is allowed to cool to room temperature and is then evaporated to dryness. The residue obtained is crystallized from hot methanol. The precipitate thus formed is filtered off and then rinsed thoroughly with ether. After drying under vacuum at about 40° C., 0.01 g of pure product is obtained in the form of a white powder.

m.p. (° C.): 216-218° C.

$^1$H NMR (DMSO) δ (ppm): 8.40 (s, 1H); 8.20 (broad s, 1H); 7.80 (broad s, 3H); 7.60 (s, 2H); 7.30 (s, 2H); 6.80 (s, 1H); 6.50 (t, 1H); 5.20 (s, 2H); 4.10 (m, 1H); 3.50-3.30 (m, 4H); 2.30 (m, 2H); 2.00 (m, 4H).

EXAMPLE 7

Compound 11

3-(Methylcarbamoyl)isoxazol-5-ylmethyl{6-[5-(4-fluorophenyl)pyridin-2-yl]-6-azaspiro[3.4]oct-2-yl}carbamate (Mixture of Isomers)

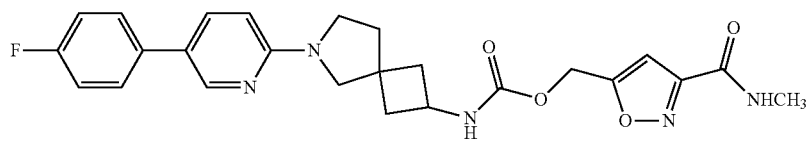 [SMILES: CNC(=O)c1cc(COC(=O)NC2CC3(CCN(c4ccc(-c5ccc(F)cc5)cn4)C3)C2)on1]

The process is performed according to the procedure described in Example 6 (step 6.9.). Starting with 0.045 g (0.09 mmol) of ethyl 5-{6-[5-(4-fluorophenyl)pyridin-2-yl]-6-azaspiro[3.4]oct-2-ylcarbamoyloxymethyl}isoxazole-3-carboxylate, described in Example 6 (step 6.8.) and 1.14 mL of a solution (8M) of methylamine in ethanol, and after purification by chromatography on preparative plates, eluting with ethyl acetate, 0.009 g of pure product is obtained in the form of a white powder.

m.p. (° C.): 184-186° C.

$^1$H NMR (DMSO) δ (ppm): 8.70 (s, 1H); 8.40 (s, 1H); 7.80 (m, 2H); 7.60 (m, 2H); 7.30 (m, 2H); 6.80 (s, 1H); 6.50 (t, 1H); 5.20 (s, 2H); 4.10 (m, 1H); 3.50-3.30 (m, 4H); 2.80 (s, 3H); 2.30 (m, 2H); 2.00 (m, 4H).

EXAMPLE 8

Compound 12

3-(Methylcarbamoyl)isoxazol-5-ylmethyl 6-[5-(4-fluorophenyl)pyridin-2-yl]-6-azaspiro[3.4]oct-2-ylmethylcarbamate (Isomer I)

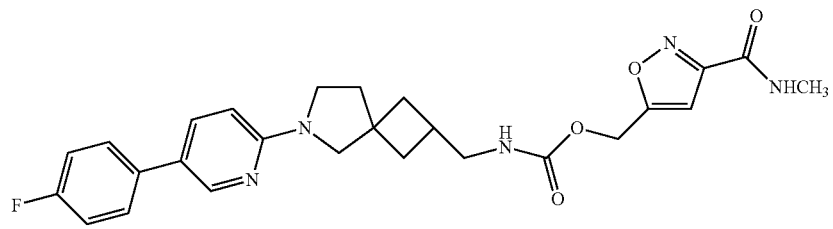 [SMILES: CNC(=O)c1cc(COC(=O)NCC2CC3(CCN(c4ccc(-c5ccc(F)cc5)cn4)C3)C2)on1]

8.1. tert-Butyl 2-cyano-6-azaspiro[3.4]octane-6-carboxylate: Isomers 1a and 1b 3.05 g (62.21 mmol) of sodium cyanide are added to a solution of 1.90 g (6.22 mmol) of tert-butyl 2-methanesulfonyloxy-6-azaspiro[3.4]octane-6-carboxylate, prepared in Example 6 (step 6.2.), in 20 mL of anhydrous dimethyl sulfoxide. The reaction mixture is then stirred at 130° C. for 12 hours.

The reaction medium is allowed to warm to room temperature and is then taken up in ether, the aqueous phase is separated out and extracted twice with ether, and the combined organic phases are then dried over sodium sulfate. After evaporating off the solvent, the residue obtained is purified by chromatography on silica gel, eluting with a 5/95 mixture of ethyl acetate and cyclohexane. 0.27 g of isomer 1a is thus obtained in the form of white crystals, and 0.20 g of isomer 1b is obtained in the form of a yellow oil.

Isomer 1a m.p. (° C.): 62-64° C.

$R_f$=0.49 (50/50 ethyl acetate/cyclohexane)

$^1$H NMR (DMSO) δ (ppm): 3.4 (m, 1H); 3.1 (m, 4H); 2.5 (m, 4H); 2.3 (t, 2H); 1.4 (s, 9H).

Isomer 1b $R_f$=0.42 (50/50 ethyl acetate/cyclohexane)

$^1$H NMR (DMSO) δ (ppm): 3.4 (m, 1H); 3.3 (m, 2H); 3.2 (m, 2H); 2.5 (s, 4H); 1.9 (m, 2H); 1.4 (s, 9H).

8.2. tert-Butyl 2-aminomethyl-6-azaspiro[3.4]octane-6-carboxylate: Isomer 2a Raney nickel is added in catalytic amount to a solution of 0.27 g (1.14 mmol) of tert-butyl 2-cyano-6-azaspiro[3.4]octane-6-carboxylate (isomer 1a), obtained in step 8.1., in 10 mL of a 1N solution of sodium hydroxide in ethanol. The reaction medium is placed in a Parr flask under a hydrogen atmosphere (4 bar), at room temperature for 5 hours.

The resulting mixture is filtered through Celite and the filtrate is then concentrated under reduced pressure. Dichloromethane is added, the aqueous phase is separated out and extracted three times with dichloromethane, and the combined organic phases are washed with saturated aqueous sodium chloride solution and dried over sodium sulfate. After evaporating off the solvent, 0.24 g of product is obtained in the form of a yellow oil, which is used without further purification in the following step.

Isomer 2a

LC-MS: M+H=241

$^1$H NMR (DMSO) δ (ppm): 3.2 (m, 2H); 3.1 (m, 2H); 2.5 (m, 2H); 2.2 (m, 1H); 1.9 (m, 2H); 1.7 (m, 2H); 1.6 (m, 2H); 1.4 (s, 9H).

8.3. tert-Butyl 2-{[3-(methylcarbamoyl)isoxazol-5-ylmethoxycarbonylamino]methyl}-6-azaspiro[3.4]octane-6-carboxylate The process is performed according to the procedure described in Example 1, step 1.1. Starting with 0.22 g (0.92 mmol) of tert-butyl 2-aminomethyl-6-azaspiro[3.4]octane-6-carboxylate (isomer 2a), described in Example 8 (step 8.2.), 0.294 g (0.92 mmol) of 3-(methylcarbamoyl)isoxazol-5-ylmethyl 4-nitrophenyl carbonate, obtained in step 4.1., 0.236 g (1.83 mmol) of N,N-diisopropylethylamine and 0.011 g (0.09 mmol) of N,N-dimethylaminopyridine, and after purification by chromatography on silica gel, eluting with a 98/2 mixture of dichloromethane and methanol, 0.310 g of pure product is thus obtained in the form of an amorphous solid.

LC-MS: M+H=423

$^1$H NMR (DMSO) δ (ppm): 8.80 (broad s, 1H); 7.50 (broad s, 1H); 6.80 (s, 1H); 5.20 (s, 2H); 3.25 (m, 2H); 3.15 (m, 2H); 3.10 (m, 2H); 2.80 (s, 3H); 2.40 (m, 1H); 2.00-1.80 (m, 4H); 1.70 (m, 2H); 1.40 (s, 9H) 3.15 (m, 2H).

8.4. 3-(Methylcarbamoyl)isoxazol-5-ylmethyl(6-azaspiro[3.4]oct-2-ylmethyl)carbamate trifluoroacetate The process is performed according to the procedure described in Example 6, step 6.6. Starting with 0.31 g (0.73 mmol) of tert-butyl 2-{[3-(methylcarbamoyl)isoxazol-5-ylmethoxycarbonylamino]methyl}-6-azaspiro[3.4]octane-6-carboxylate, obtained in step 8.3. and 0.62 mL (7.34 mmol) of a trifluoroacetic acid solution, 0.32 g of product in trifluoroacetate form is obtained, which is used without further purification in step 8.5. below.

8.5. 3-(Methylcarbamoyl)isoxazol-5-ylmethyl 6-[5-(4-fluorophenyl)pyridin-2-yl]-6-azaspiro[3.4]oct-2-ylmethylcarbamate (Isomer I)

The process is performed according to the procedure described in Example 1 (step 1.3.). Starting with 0.32 g (0.73 mmol) of 3-(methylcarbamoyl)isoxazol-5-ylmethyl(6-azaspiro[3.4]oct-2-ylmethyl)carbamate trifluoroacetate, described in step 8.4., 0.16 g (0.88 mmol) of 2-fluoro-5-(4-fluorophenyl)pyridine, prepared in step 6.7. and 0.38 g (2.92 mmol) of N,N-diisopropylethylamine, and after purification by chromatography on silica gel, eluting with a 98/2/0.2 mixture of dichloromethane and methanol and aqueous ammonia, 0.07 g of pure product is thus obtained in the form of a white solid.

m.p. (° C.): 171-173° C.
LC-MS: M+H=494
$^1$H NMR (DMSO) δ (ppm):8.70 (broad s, 1H); 8.40 (s, 1H); 7.80 (m, 1H); 7.60 (m, 2H); 7.50 (m, 1H); 7.30 (m, 2H); 6.80 (s, 1H); 6.50 (d, 1H); 5.20 (s, 2H); 3.50 (m, 2H); 3.35 (m, 2H); 3.10 (t, 2H) 2.80 (s, 3H); 2.40 (m, 1H); 2.00 (m, 4H); 1.80 (m, 2H).

EXAMPLE 9

Compound 13

3-(Methylcarbamoyl)isoxazol-5-ylmethyl 6-[5-(4-fluorophenyl)pyridin-2-yl]-6-azaspiro[3.4]oct-2-ylmethylcarbamate (Isomer II)

carboxylate (isomer 2b), described in Example 9 (step 9.1.), 0.321 g (1.00 mmol) of 3-(methylcarbamoyl)isoxazol-5-ylmethyl 4-nitrophenyl carbonate, obtained in step 4.1., 0.258 g (2.00 mmol) of N,N-diisopropylethylamine and 0.012 g (0.10 mmol) of N,N-dimethylaminopyridine, and after purification by chromatography on silica gel, eluting with a 98/2 mixture of dichloromethane and methanol, 0.320 g of pure product is thus obtained in the form of an amorphous solid.

LC-MS: M+H=423
$^1$H NMR (DMSO) δ (ppm): 8.80 (broad s, 1H); 7.50 (broad s, 1H); 6.80 (s, 1H); 5.20 (s, 2H); 3.25 (m, 2H); 3.15 (m, 2H); 3.10 (m, 2H); 2.80 (s, 3H); 2.40 (m, 1H); 2.00-1.80 (m, 4H); 1.70 (m, 2H); 1.40 (s, 9H) 3.15 (m, 2H).

9.3. 3-(Methylcarbamoyl)isoxazol-5-ylmethyl(6-azaspiro[3.4]oct-2-ylmethyl)carbamate trifluoroacetate The process is performed according to the procedure described in Example 6, step 6.6. Starting with 0.32 g (0.76 mmol) of ter-butyl 2-[(3-(methylcarbamoyl)isoxazol-5-ylmethoxycarbonylamino)methyl]-6-azaspiro[3.4]octane-6-carboxylate, obtained in step 9.2. and 0.64 mL (7.57 mmol) of a trifluoroacetic acid solution, 0.33 g of product is obtained in trifluoroacetate form, which is used without further purification in step 9.4. below.

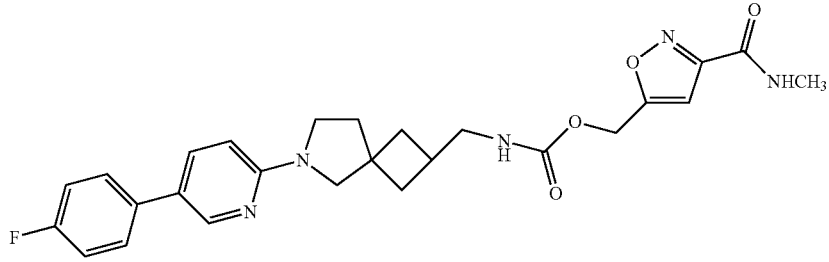 [SMILES: CNC(=O)c1cc(COC(=O)NCC2CC3(CCN(c4ccc(-c5ccc(F)cc5)cn4)C3)C2)on1]

9.1. tert-Butyl 2-aminomethyl-6-azaspiro[3.4]octane-6-carboxylate: Isomer 2b The process is performed according to the procedure described in Example 8 (step 8.2.). Starting with 0.20 g (0.85 mmol) of ter-butyl 2-cyano-6-azaspiro[3.4]octane-6-carboxylate, (isomer 1b), described in Example 8 (step 8.1.) and a catalytic amount of Raney nickel, 0.22 g of product is obtained in the form of a yellow oil, which is used without further purification in the following step.

Isomer 2b
LC-MS: M+H=241
$^1$H NMR (DMSO) δ (ppm): 3.2 (m, 2H); 3.1 (m, 2H); 2.5 (m, 2H); 2.2 (m, 1H); 1.9 (m, 4H); 1.7 (m, 2H); 1.4 (s, 9H).

9.2. tert-Butyl 2-[(3-(methylcarbamoyl)isoxazol-5-ylmethoxycarbonylamino)methyl]-6-azaspiro[3.4]octane-6-carboxylate The process is performed according to the procedure described in Example 1, step 1.1. Starting with 0.24 g (1.00 mmol) of tert-butyl 2-aminomethyl-6-azaspiro[3.4]octane-6-

9.4. 3-(Methylcarbamoyl)isoxazol-5-ylmethyl 6-[5-(4-fluorophenyl)pyridin-2-yl]-6-azaspiro[3.4]oct-2-ylmethylcarbamate (Isomer II)

The process is performed according to the procedure described in Example 1 (step 1.3.). Starting with 0.33 g (0.76 mmol) of 3-(methylcarbamoyl)isoxazol-5-ylmethyl(6-azaspiro[3.4]oct-2-ylmethyl)carbamate trifluoroacetate, described in step 9.3., 0.174 g (0.91 mmol) of 2-fluoro-5-(4-fluorophenyl)pyridine, prepared in step 6.7. and 0.393 g (3.04 mmol) of N,N-diisopropylethylamine, and after purification by chromatography on silica gel, eluting with a 98/2 mixture of dichloromethane and methanol, 0.10 g of pure product is thus obtained in the form of a white solid.

m.p. (° C.): 180-182° C.
LC-MS: M+H=494
$^1$H NMR (DMSO) δ (ppm): 8.70 (broad s, 1H); 8.40 (s, 1H); 7.80 (m, 1H); 7.60 (m, 2H); 7.50 (m, 1H); 7.30 (m, 2H); 6.80 (s, 1H); 6.50 (d, 1H); 5.20 (s, 2H); 3.50 (s, 2H); 3.40 (m, 2H); 3.10 (t, 2H); 2.80 (s, 3H); 2.40 (m, 1H); 2.10 (t, 2H); 1.90 (t, 2H) 1.80 (t, 2H).

EXAMPLE 10

Compound 8

3-(Methylcarbamoyl)isoxazol-5-ylmethyl 7-[5-(4-fluorophenyl)pyridin-2-yl]-7-azaspiro[3.5]non-2-ylcarbamate

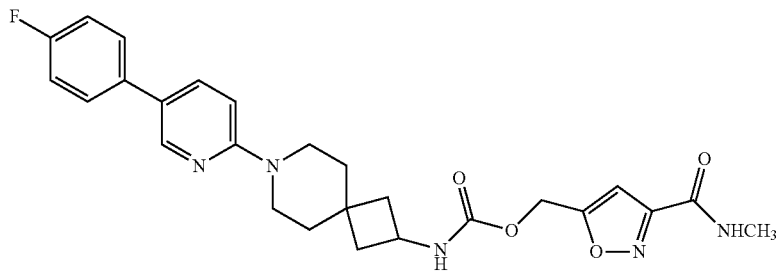 [SMILES: CNC(=O)c1cc(COC(=O)NC2CC3(CCN(c4ccc(-c5ccc(F)cc5)cn4)CC3)C2)on1]

10.1. 7-(5-Bromopyridin-2-yl)-7-azaspiro[3.5]nonan-2-ol 0.24 g (1.35 mmol) of 5-bromo-2-fluoropyridine, 0.20 g (1.13 mmol) of 7-azaspiro[3.5]nonan-2-ol hydrochloride (JP 2003246780) and 0.51 g (3.94 mmol) of N,N-diisopropylethylamine in 3 mL of acetonitrile are placed in a sealed tube. 1 mL of DMF is added and the mixture is then heated at 95° C. for 12 hours. The reaction mixture is allowed to cool to room temperature and is then taken up in ethyl acetate and water. The aqueous phase is separated out and the combined organic phases are then washed with saturated aqueous ammonium chloride solution and dried over sodium sulfate, and the filtrate is concentrated under reduced pressure. After purification by chromatography on silica gel, eluting with a 95/5/0.5 mixture of dichloromethane, methanol and 28% aqueous ammonia, 0.138 g pure product is thus obtained in the form of a colourless gum.

LC-MS: M+H=298
$^1$H NMR (CDCl$_3$) δ (ppm): 8.10 (s, 1H); 7.50 (d, 1H); 6.50 (d, 1H); 4.30 (m, 1H); 3.30 (m, 4H); 2.25 (m, 2H); 1.65 (m, 2H); 1.50 (m, 4H).

10.2. 7-[5-(4-Fluorophenyl)pyridin-2-yl]-7-azaspiro[3.5]nonan-2-ol

The process is performed according to the procedure described in Example 2 (step 2.7.). Starting with 0.138 g (0.46 mmol) of 7-(5-bromopyridin-2-yl)-7-azaspiro[3.5]nonan-2-ol, obtained in step 10.1., 0.078 g (0.56 mmol) of 4-fluorophenylboronic acid, 0.454 g (1.39 mmol) of caesium carbonate suspended in 3 mL of a 9/1 mixture of tetrahydrofuran and water. 0.038 g (0.05 mmol) of PdCl$_2$dppf.CH$_2$Cl$_2$ is then added. 0.101 g of pure product is thus obtained in the form of a grey powder.

m.p. (° C.): 139-141° C.
LC-MS: M+H=313
$^1$H NMR (CDCl$_3$) δ (ppm): 8.30 (s, 1H); 7.60 (d, 1H); 7.40 (m, 2H); 7.10 (m, 2H); 6.60 (d, 1H); 4.30 (m, 1H); 3.30 (m, 4H); 2.30 (m, 2H); 1.65 (m, 2H); 1.50 (m, 4H).

10.3. 7-[5-(4-Fluorophenyl)pyridin-2-yl]-7-azaspiro[3.5]non-2-yl methanesulfonate The process is performed according to the procedure described in Example 6 (step 6.2.). 3.25 mL (23.34 mmol) of triethylamine and then 0.91 mL (11.67 mmol) of mesyl chloride are added to a solution of 2.43 g (7.78 mmol) of 7-[5-(4-fluorophenyl)pyridin-2-yl]-7-azaspiro[3.5]nonan-2-ol, obtained in step 10.2., in 25 mL of dichloromethane. 3.03 g of product are obtained in the form of a yellow oil, which is used without further purification in the following step.

10.4. 2-Azido-7-[5-(4-fluorophenyl)pyridin-2-yl]-7-azaspiro[3.5]nonane

The process is performed according to the procedure described in Example 6 (step 6.3.). Starting with 7.66 g (19.62 mmol) of 7-[5-(4-fluorophenyl)pyridin-2-yl]-7-azaspiro[3.5]non-2-yl methanesulfonate, prepared in step 10.3., and 3.83 g (58.85 mmol) of sodium azide in 28 mL of N,N-dimethylformamide. After evaporating off the solvent, 6.60 g of product are obtained in the form of a brown oil.

10.5. 7-[5-(4-Fluorophenyl)pyridin-2-yl]-7-azaspiro[3.5]non-2-ylamine

The process is performed according to the procedure described in Example 6 (step 6.4.). Starting with 6.60 g (19.56 mmol) of 2-azido-7-[5-(4-fluorophenyl)pyridin-2-yl]-7-azaspiro[3.5]nonane, obtained in step 10.4., in 28 mL of ethanol, 0.81 g (3.91 mmol) of Lindlar catalyst (PdCaCO$_3$) is added. 3.89 g of pure product are thus obtained in the form of a yellow powder.

m.p. (° C.): 120-122° C.
LC-MS: M+H=312
$^1$H NMR (CDCl$_3$) δ (ppm): 8.45 (s, 1H); 7.70 (m, 1H); 7.50 (m, 2H); 7.20 (m, 2H); 6.80 (d, 1H); 3.70-3.40 (m, 5H); 2.35 (m, 4H); 1.80-1.50 (m, 6H).

10.6. 3-(Methylcarbamoyl)isoxazol-5-ylmethyl 7-[5-(4-fluorophenyl)pyridin-2-yl]-7-azaspiro[3.5]non-2-ylcarbamate The process is performed according to the procedure described in Example 1, step 1.1. Starting with 1.08 g (3.47 mmol) of 7-[5-(4-fluorophenyl)pyridin-2-yl]-7-azaspiro[3.5]non-2-ylamine, described in the preceding step (step 10.5.), 1.34 g (4.16 mmol) of 3-(methylcarbamoyl)isoxazol-5-ylmethyl 4-nitrophenyl carbonate, obtained in step 4.1., 1.12 g (8.67 mmol) of N,N-diisopropylethylamine and 0.212 g (1.73 mmol) of N,N-dimethylaminopyridine, and after purification by chromatography on silica gel, eluting with a 98/2 mixture of dichloromethane and methanol, 0.847 g of pure product is thus obtained in the form of a white solid.

m.p. (° C.): 219-221° C.
LC-MS: M+H=493
$^1$H NMR (DMSO) δ (ppm): 8.70 (broad s, 1H); 8.40 (s, 1H); 7.90-7.70 (m, 2H); 7.65 (m, 2H); 7.25 (m, 2H); 6.90 (d, 1H); 6.80 (s, 1H); 5.20 (s, 2H); 4.00 (m, 1H); 3.55 (t, 2H); 3.45 (t, 2H); 2.80 (s, 3H); 2.20 (m, 2H); 1.75 (m; 2H); 1.65-1.45 (m, 4H).

EXAMPLE 11

Compound 15

3-(Methylcarbamoyl)isoxazol-5-ylmethyl 2-(6-fluoroquinolin-2-yl)-2-azaspiro[3.3]hept-6-ylcarbamate

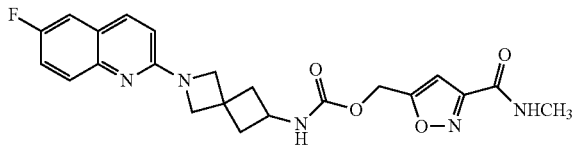 [SMILES: CNC(=O)c1cc(COC(=O)NC2CC3(C2)CN(c2ccc4cc(F)ccc4n2)C3)on1]

11.1. tert-Butyl 5,5-dichloro-6-oxo-2-azaspiro[3.3]heptane-2-carboxylate 28.42 mL (254.65 mmol) of trichloroacetyl chloride dissolved in 70 mL of dimethoxyethane are added dropwise, at 0° C., to a mixture containing 7.98 g (47.16 mol) of tert-butyl 3-methyleneazetidine-1-carboxylate (WO 2008/124 085) and 36.48 g (282.94 mmol) of zinc-copper amalgam suspended in 200 mL of ether. The reaction medium is stirred at room temperature for 12 hours. The mixture is then poured portionwise into a sodium carbonate solution at 0° C. The solution obtained is filtered through Celite and rinsed thoroughly with water and ether. The aqueous phase is then separated out and extracted several times with ether. The combined organic phases are dried over sodium sulfate and the filtrate is concentrated under reduced pressure. After evaporating off the solvent, the product obtained, in the form of a brown oil, is used without further purification in the following step.

11.2. tert-Butyl 6-oxo-2-azaspiro[3.3]heptane-2-carboxylate 15.13 g (0.283 mmol) of ammonium chloride are added to a solution containing 13.21 g (47.15 mmol) of tert-butyl 5,5-dichloro-6-oxo-2-azaspiro[3.3]heptane-2-carboxylate, obtained in the preceding step, in 250 mL of methanol. The reaction medium is cooled with the aid of an ice/water bath, and 30.83 g (0.471 mmol) of zinc are added. After stirring at room temperature for 12 hours, the Celite is filtered off and rinsed with methanol. The filtrate is evaporated to dryness. The residue obtained is taken up in water and extracted several times with ethyl acetate. The combined organic phases are dried over sodium sulfate and the filtrate is concentrated under reduced pressure. After evaporating off the solvent, the residue obtained is purified by chromatography on silica gel, eluting with a 90/10 mixture of cyclohexane and ethyl acetate. 1.78 g of pure product are thus obtained in the form of a white powder.
m.p. (° C.): 117-119° C.
LC-MS: M+H=212
$^1$H NMR (DMSO) δ (ppm): 4.05 (s, 4H); 3.30 (s, 4H); 1.40 (s, 9H).

11.3. tert-Butyl 6-hydroxy-2-azaspiro[3.3]heptane-2-carboxylate

The process is performed according to the procedure described in Example 6, step 6.1. Starting with 1.40 g (6.63 mmol) of tert-butyl 6-oxo-2-azaspiro[3.3]heptane-2-carboxylate, obtained in step 11.2., dissolved in 17 mL of methanol and 0.376 g (9.94 mmol) of sodium borohydride. After evaporating off the solvent and crystallizing from a 70/30 mixture of petroleum ether and diisopropyl ether, 1.18 g of the expected product are obtained in the form of a white powder.
m.p. (° C.): 131-133° C.
LC-MS: M+H=214
$^1$H NMR (DMSO) δ (ppm): 5.00 (s, 1H); 3.95 (m, 1H); 3.75 (d, 4H); 2.40 (m, 2H); 1.90 (m, 2H); 1.40 (s, 9H).

11.4. tert-Butyl 2-azaspiro[3.3]heptane-2-carboxylate 6-methanesulfonate

The process is performed according to the procedure described in Example 6, step 6.2. Starting with 0.97 g (4.55 mmol) of tert-butyl 6-hydroxy-2-azaspiro[3.3]heptane-2-carboxylate, obtained in step 11.3. dissolved in 40 mL of dichloromethane, 0.70 mL (5.00 mmol) of triethylamine and 0.39 mL (5.00 mmol) of mesyl chloride, and after purification on a column of silica gel, eluting with a 90/10 to 70/30 gradient of a mixture of cyclohexane and ethyl acetate, 0.790 g of product is obtained, which is used without further purification in the following step.

11.5. tert-Butyl 6-azido-2-azaspiro[3.3]heptane-2-carboxylate

The process is performed according to the procedure described in Example 2, step 2.1. Starting with 0.780 g (2.68 mmol) of tert-butyl 2-azaspiro[3.3]heptane-2-carboxylate 6-methanesulfonate obtained in step 11.4. and 0.350 g (5.35 mmol) of sodium azide in 8 mL of N,N-dimethylformamide, 0.63 g of product is obtained, which is used without further purification in the following step.

11.6. tert-Butyl 6-amino-2-azaspiro[3.3]heptane-2-carboxylate

The process is performed according to the procedure described in Example 6 (step 6.4.). Starting with 0.638 g (2.68 mmol) of tert-butyl 6-azido-2-azaspiro[3.3]heptane-2-carboxylate, obtained in step 11.5., in 11 mL of ethanol, 0.276 g (1.34 mmol) of Lindlar catalyst (PdCaCO$_3$) is added. After purification on a column of silica gel, eluting with a 98/2/0.2 mixture of dichloromethane, methanol and 28% aqueous ammonia, 0.330 g of pure product is obtained in the form of a white powder.
m.p. (° C.): 50-53° C.
LC-MS: M+H=213
$^1$H NMR (DMSO+D$_2$O) δ (ppm): 3.80 (s, 2H); 3.70 (s, 2H); 3.10 (m, 1H); 2.30 (t, 2H); 1.75 (t, 2H); 1.40 (s, 9H).

11.7. tert-Butyl 6-(3-ethoxycarbonylisoxazol-5-ylmethoxycarbonylamino)-2-azaspiro[3.3]heptane-2-carboxylate 0.341 g (2.64 mmol) of N,N-diisopropylethylamine and 0.265 g (1.32 mmol) of 4-nitrophenyl chloroformate are added to a solution of 0.226 g (1.32 mmol) of ethyl 5-hydroxymethylisoxazole-3-carboxylate in 10 mL of dichloroethane. Stirring is continued at room temperature for hours and 0.280 g (1.32 mmol) of tert-butyl 6-amino-2-azaspiro[3.3] heptane-2-carboxylate, obtained in step 11.6., dissolved in 4 mL of dichloroethane, is then added. Stirring is continued at room temperature for 4 hours. Water is added to the reaction medium, the aqueous phase is separated out and extracted several times with dichloromethane, and the combined organic phases are washed with aqueous sodium hydroxide solution (1N) and then with saturated aqueous ammonium chloride solution. The resulting phase is dried over sodium sulfate and the filtrate is concentrated under reduced pressure. After evaporating off the solvent, the residue obtained is purified by chromatography on silica gel, eluting with a 98/2 mixture of dichloromethane and methanol.

0.42 g of pure product is thus obtained in the form of an amorphous solid.

LC-MS: M+H=410

$^1$H NMR (DMSO) δ (ppm): 7.70 (d, 1H); 6.90 (s, 1H); 5.20 (s, 2H); 4.40 (m, 3H); 3.85 (m, 2H); 3.75 (s, 2H); 2.40 (t, 2H); 2.10 (t, 2H); 1.40-1.20 (m, 12H).

11.8. Ethyl 5-(2-azaspiro[3.3]hept-6-ylcarbamoyloxymethyl)isoxazole-3-carboxylate trifluoroacetate The process is performed according to the procedure described in Example 6, step 6.6. Starting with 0.42 g (1.03 mmol) of tert-butyl 6-(3-ethoxycarbonylisoxazol-5-ylmethoxycarbonylamino)-2-azaspiro[3.3]heptane-2-carboxylate, obtained in step 11.7., and 0.86 mL (10.26 mmol) of a trifluoroacetic acid solution, 0.43 g of product in trifluoroacetate form is obtained, which is used without further purification in step 11.9. below.

11.9. Ethyl 5-[2-(6-Fluoroquinolin-2-yl)-2-azaspiro [3.3]hept-6-ylcarbamoyloxymethyl]isoxazole-3-carboxylate The process is performed according to the procedure described in Example 2 (step 2.6.). Starting with 0.43 g (1.03 mmol) of ethyl 5-(2-azaspiro[3.3]hept-6-ylcarbamoyloxymethyl)isoxazole-3-carboxylate trifluoroacetate, obtained in step 11.8., 0.187 g (1.03 mmol) of 2-chloro-6-fluoroquinoline and 0.399 g (3.09 mmol) of N,N-diisopropylethylamine, and after chromatography on silica gel, eluting with a 98/2 mixture of dichloromethane and methanol, 0.15 g of pure product in the form of a beige-coloured solid is thus obtained.

LC-MS: M+H=455 m.p. (° C.): 107-109° C.

$^1$H NMR (DMSO) δ (ppm): 8.05 (d, 1H); 7.80 (d, 1H); 7.60 (m, 1H); 7.50 (m, 1H); 7.40 (m, 1H); 6.90 (s, 1H); 6.70 (d, 1H); 5.25 (s, 2H); 4.40 (q, 2H); 4.10 (s, 2H); 4.00 (s, 2H); 3.90 (m, 2H); 2.50 (t, 2H); 2.20 (t, 2H); 1.35 (t, 3H).

11.10. 3-(Methylcarbamoyl)isoxazol-5-ylmethyl 2-(6-fluoroquinolin-2-yl)-2-azaspiro[3.3]hept-6-ylcarbamate In a sealed tube, a solution of 0.130 g (0.28 mmol) of ethyl 5-[2-(6-fluoroquinolin-2-yl)-2-azaspiro[3.3]hept-6-ylcarbamoyloxymethyl]isoxazole-3-carboxylate, prepared in step 11.9., in 4.13 mL (28.01 mmol) of a solution (8M) of methylamine in ethanol, is stirred at room temperature for 5 hours. The mixture is evaporated to dryness. The residue obtained is crystallized from hot ether. The precipitate thus formed is filtered off and rinsed thoroughly with ether. After drying under vacuum at about 60° C., 0.05 g of pure product is obtained in the form of a white powder.

m.p. (° C.): 167-169° C.

$^1$H NMR (DMSO) δ (ppm): 8.70 (broad s, 1H); 8.05 (d, 1H); 7.80 (d, 1H); 7.60 (m, 1H); 7.50 (m, 1H); 7.40 (m, 1H); 6.80 (s, 1H); 6.75 (d, 1H); 5.25 (s, 2H); 4.15 (s, 2H); 4.05 (s, 2H); 3.95 (m, 1H); 2.80 (s, 3H); 2.50 (t, 2H); 2.20 (t, 2H).

EXAMPLE 12

Compound 17

3-(Methylcarbamoyl)isoxazol-5-ylmethyl{6-[5-(4-fluorophenyl)pyridin-2-yl]-6-azaspiro[3.4]oct-2-yl}carbamate (Isomer I)

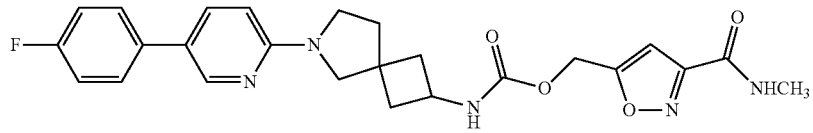 [SMILES: CNC(=O)c1cc(COC(=O)NC2CC3(CCN(c4ccc(-c5ccc(F)cc5)cn4)C3)C2)on1]

12.1 tert-Butyl 2-methanesulfonyloxy-6-azaspiro [3.4]octane-6-carboxylate (Isomers 1 and 1')

Isomers 1 and 1' of tert-butyl 2-methanesulfonyloxy-6-azaspiro[3.4]octane-6-carboxylate, prepared according to the method described in Example 6 (step 6.2.), are separated by column chromatography on silica gel, eluting with a 100/0 to 80/20 cyclohexane/ethyl acetate mixture. 1.69 g of isomer 1 in the form of a white solid, and 1.62 g of isomer 1' in the form of a white solid, are thus obtained.

Isomer 1 m.p. (° C.): 76-78° C.

LC-MS: M+H=306

Rf=0.35 (50/50 ethyl acetate/cyclohexane)

$^1$H NMR (DMSO) δ (ppm): 5.08 (m, 1H); 3.28 (m, 2H); 3.20 (m, 2H); 3.15 (s, 3H); 2.42 (m, 2H); 2.22 (m, 2H); 1.85 (m, 2H); 1.40 (s, 9H).

Isomer 1' m.p. (° C.): 79-82° C.

LC-MS: M+H=306

Rf=0.29 (50/50 ethyl acetate/cyclohexane)

$^1$H NMR (DMSO) δ (ppm): 5.00 (m, 1H); 3.22 (m, 4H), 3.12 (s, 3H), 2.36 (m, 2H); 2.22 (m, 2H); 1.80 (m, 2H); 1.35 (s, 9H).

12.2 tert-Butyl 2-azido-6-azaspiro[3.4]octane-6-carboxylate (Isomer 2')

The process is performed according to the procedure described in Example 6 (step 6.3.). Starting with 1.62 g (5.30 mmol) of tert-butyl 2-methanesulfonyloxy-6-azaspiro[3.4] octane-6-carboxylate (isomer 1'), described in Example 12 (step 12.1.), and 0.68 g (10.61 mmol) of sodium azide, the product is obtained in the form of a yellow oil, which is used without further purification in the following step.

12.3 tert-Butyl 2-amino-6-azaspiro[3.4]octane-6-carboxylate (Isomer 3')

The process is performed according to the procedure described in Example 6 (step 6.4). Starting with 1.33 g (5.30 mmol) of tert-butyl 2-azido-6-azaspiro[3.4]octane-6-carboxylate (isomer 2') and 0.54 g (2.65 mmol) of Lindlar catalyst (PdCaCO$_3$), 0.70 g of product is obtained in the form of an oil.

LC-MS: M+H=227

$^1$H NMR (DMSO+D$_2$O) δ (ppm): 3.24 (m, 1H); 3.15 (m, 4H); 2.12 (m, 2H); 1.74 (m, 2H); 1.60 (m, 2H); 1.36 (s, 9H).

12.4 tert-Butyl 2-(3-carbamoylisoxazol-5-yl-methoxycarbonylamino)-6-azaspiro[3.4]octane-6-carboxylate (Isomer 4')

The process is performed according to the procedure described in Example 4 (step 4.2). Starting with 0.70 g (3.09 mmol) of tert-butyl 2-amino-6-azaspiro[3.4]octane-6-carboxylate (isomer 3') and 1.04 g (3.09 mmol) of ethyl 5-(4-nitrophenoxycarbonyloxymethyl)isoxazole-3-carboxylate, 1.10 g of product are obtained in the form of a gum.

LC-MS: M+H=424

$^1$H NMR (DMSO) δ (ppm): 7.80 (bd, 1H); 6.92 (s, 1H); 5.21 (s, 2H); 4.35 (q, 2H); 3.98 (m, 1H); 3.21 (m, 2H); 3.15 (m, 2H); 2.21 (m, 2H); 1.90 (m, 2H); 1.75 (m, 2H); 1.40 (s, 9H); 1.30 (t, 3H).

12.5 Ethyl 5-(6-azaspiro[3.4]oct-2-ylcarbamoyloxymethyl)isoxazole-3-carboxylate trifluoroacetate (Isomer 5')

The process is performed according to the procedure described in Example 6 (step 6.6.). Starting with 1.10 g (2.60 mmol) of tert-butyl 2-(3-carbamoylisoxazol-5-ylmethoxycarbonylamino)-6-azaspiro[3,4]octane-6-carboxylate (isomer 4') and 2.19 ml (25.98 mmol) of trifluoroacetic acid, the product is obtained, which is used in the following step.

12.6 Ethyl 5-[6-(5-bromopyridin-2-yl)-6-azaspiro [3.4]oct-2-ylcarbamoyloxymethyl]-isoxazole-3-carboxylate (Isomer 6')

The process is performed according to the procedure described in Example 2 (step 2.6.). Starting with 0.43 g (1.03 mmol) of ethyl 5-(6-azaspiro[3.4]oct-2-ylcarbamoyloxymethyl)isoxazole-3-carboxylate trifluoroacetate (isomer 5'), obtained in step 12.5., and 0.45 g (2.60 mmol) of 2-fluoro-5-bromopyridine, and after chromatography on silica gel, eluting with a 97/3 mixture of dichloromethane and methanol, 0.68 g of pure product is obtained in the form of an oil.

12.7 Ethyl 5-{6-[5-(4-fluorophenyl)pyridin-2-yl]-6-azaspiro[3.4]oct-2-ylcarbamoyloxymethyl}-isoxazole-3-carboxylate (Isomer 7')

The process is performed according to the procedure described in Example 2 (step 2.7.). Starting with 0.68 g (1.42 mmol) of ethyl 5-[6-(5-bromopyridin-2-yl)-6-azaspiro[3.4] oct-2-ylcarbamoyloxymethyl]isoxazole-3-carboxylate (isomer 6') and 0.23 g (1.70 mmol) of 4-fluorophenylboronic acid, 1.38 g (4.26 mmol) of caesium carbonate and 0.11 g (0.14 mmol) of PdCl$_2$dppf.CH$_2$Cl$_2$, 0.32 g of a white solid is obtained.

m.p. (° C.)=164-166

LC-MS: M+H=495

$^1$H NMR (DMSO) δ (ppm): 8.40 (s, 1H); 7.80 (m, 2H); 7.62 (m, 2H); 7.22 (t, 2H); 6.89 (s, 1H); 6.50 (d, 1H); 5.21 (s, 2H); 4.35 (q, 2H); 4.05 (m, 1H); 3.50 (s, 2H); 3.40 (m, 2H); 2.30 (m, 2H); 2.00 (m, 4H); 1.30 (t, 3H).

12.8 3-(Methylcarbamoyl)isoxazol-5-ylmethyl{6-[5-(4-fluorophenyl)pyridin-2-yl]-6-azaspiro[3.4]oct-2-yl}carbamate (Isomer I)

The process is performed according to the procedure described in Example 6 (step 6.9.). Starting with 0.3 g (0.61 mmol) of ethyl 5-{6-[5-(4-fluorophenyl)pyridin-2-yl]-6-azaspiro[3.4]oct-2-ylcarbamoyloxymethyl}isoxazole-3-carboxylate (isomer 7') and 15 mL of a solution (1M) of methylamine in tetrahydrofuran at room temperature, 0.21 g of product is obtained in the form of a white solid.

LC-MS: M+H=480 m.p. (° C.): 203-205

$^1$H NMR (DMSO) δ (ppm): 8.70 (broad s, 1H), 8.40 (s, 1H); 7.81 (m, 2H); 7.62 (m, 2H); 7.25 (t, 2H); 6.78 (s, 1H); 6.50 (d, 1H); 5.20 (s, 2H); 4.08 (m, 1H); 3.50 (s, 2H), 3.40 (m, 2H); 2.78 (s, 3H), 2.30 (m, 2H); 1.99 (m, 4H).

EXAMPLE 13

Compound 18

3-(Methylcarbamoyl)isoxazol-5-ylmethyl{6-[5-(4-fluorophenyl)pyridin-2-yl]-6-azaspiro[3.4]oct-2-yl}carbamate (Isomer II)

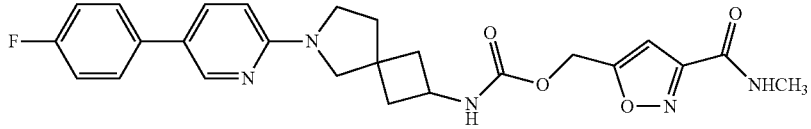 [SMILES: CNC(=O)c1cc(COC(=O)NC2CC3(CCN(c4ccc(-c5ccc(F)cc5)cn4)C3)C2)on1]

13.1 tert-Butyl 2-azido-6-azaspiro[3.4]octane-6-carboxylate (Isomer 2)

The process is performed according to the procedure described in Example 6 (step 6.3.). Starting with 2.49 g (8.15 mmol) of tert-butyl 2-methanesulfonyloxy-6-azaspiro[3.4] octane-6-carboxylate (isomer 1), described in Example 12 (step 12.1.) and 1.07 g (16.31 mmol) of sodium azide, the product is obtained, which is used in the following step.

13.2 tert-Butyl 2-amino-6-azaspiro[3.4]octane-6-carboxylate (Isomer 3)

The process is performed according to the procedure described in Example 6 (step 6.4.). Starting with 2.05 g (8.15 mmol) of tert-butyl 2-azido-6-azaspiro[3.4]octane-6-carboxylate (isomer 2) and 0.84 g (4.08 mmol) of Lindlar catalyst (PdCaCO$_3$), 1.11 g of product are obtained in the form of a yellow oil.

LC-MS: M+H=227

¹H NMR (DMSO+D₂O) δ (ppm): 3.25 (m, 1H); 3.20 (m, 2H); 3.10 (m, 2H); 2.10 (m, 2H); 1.75 (m, 2H); 1.65 (m, 2H); 1.40 (s, 9H).

13.3 tert-Butyl 2-(3-carbamoylisoxazol-5-yl-methoxycarbonylamino)-6-azaspiro[3.4]octane-6-carboxylate (Isomer 4)

The process is performed according to the procedure described in Example 4 (step 4.2). Starting with 1.11 g (4.90 mmol) of tort-butyl 2-amino-6-azaspiro[3.4]octane-6-carboxylate (isomer 3) and 1.64 g (4.90 mmol) of ethyl 5-(4-nitrophenoxycarbonyloxymethyl)isoxazole-3-carboxylate, 1.65 g of product are obtained in the form of a gum.

LC-MS: M+H=424

¹H NMR (DMSO) δ (ppm): 7.75 (broad t, 1H); 6.90 (s, 1H); 5.20 (s, 2H); 4.35 (q, 2H); 3.99 (m, 1H); 3.21 (m, 2H); 3.11 (m, 2H); 2.19 (m, 2H); 1.92 (m, 2H); 1.81 (m, 2H); 1.41 (s, 9H); 1.32 (t, 3H).

13.4 Ethyl 5-(6-azaspiro[3.4]oct-2-ylcarbamoyloxymethyl)isoxazole-3-carboxylate trifluoroacetate (Isomer 5)

The process is performed according to the procedure described in Example 6 (step 6.6.). Starting with 1.65 g (3.90 mmol) of tort-butyl 2-(3-carbamoylisoxazol-5-ylmethoxycarbonylamino)-6-azaspiro[3.4]octane-6-carboxylate (isomer 4) and 3.28 mL (38.96 mmol) of trifluoroacetic acid, the product is obtained, which is used in the following step.

13.5 Ethyl 5-[6-(5-bromopyridin-2-yl)-6-azaspiro[3.4]oct-2-ylcarbamoyloxymethyl]isoxazole-3-carboxylate (Isomer 6)

The process is performed according to the procedure described in Example 2 (step 2.6.). Starting with 1.7 g (3.90 mmol) of ethyl 5-(6-azaspiro[3.4]oct-2-ylcarbamoyloxymethyl)isoxazole-3-carboxylate trifluoroacetate (isomer 5) and 0.68 g (3.90 mmol) of 2-fluoro-5-bromopyridine, and after chromatography on silica gel, eluting with a 98/2 mixture of dichloromethane and methanol, 1.00 g of pure product is thus obtained in the form of a gum.

LC-MS: M+H=479

¹H NMR (DMSO) δ (ppm): 8.11 (s, 1H); 7.80 (broad d, 1H); 7.60 (d, 1H); 6.90 (s, 1H); 6.40 (d, 1H), 5.21 (s, 2H); 4.39 (q, 2H); 4.01 (m, 1H); 3.39 (m, 2H); 3.31 (m, 2H); 2.25 (m, 2H); 2.01 (m, 4H); 1.30 (t, 3H).

13.6 Ethyl 5-{6-[5-(4-Fluorophenyl)pyridin-2-yl]-6-azaspiro[3.4]oct-2-ylcarbamoyloxymethyl}isoxazole-3-carboxylate (Isomer 7)

The process is performed according to the procedure described in Example 2 (step 2.7.). Starting with 1.00 g (2.09 mmol) of ethyl 5-[6-(5-bromopyridin-2-yl)-6-azaspiro[3.4]oct-2-ylcarbamoyloxymethyl]isoxazole-3-carboxylate (isomer 6) and 0.29 g (2.09 mmol) of 4-fluorophenylboronic acid, 2.03 g (6.26 mmol) of caesium carbonate and 0.17 g (0.21 mmol) of PdCl₂dppf.CH₂Cl₂, 0.50 g of a gum is obtained after chromatography on silica gel, eluting with a 90/10 mixture of cyclohexane and ethyl acetate.

LC-MS: M+H=495

¹H NMR (DMSO) δ (ppm): 8.39 (s, 1H); 7.80 (m, 2H); 7.60 (m, 2H); 7.22 (t, 2H); 6.90 (s, 1H); 6.50 (d, 1H); 5.20 (s, 2H); 4.38 (q, 2H); 4.06 (m, 1H); 3.45 (m, 2H); 3.38 (m, 2H); 2.28 (m, 2H); 2.00 (m, 4H); 1.32 (t, 3H).

13.7 3-(Methylcarbamoyl)isoxazol-5-ylmethyl{6-[5-(4-fluorophenyl)pyridin-2-yl]-6-azaspiro[3.4]oct-2-yl}carbamate (Isomer II)

The process is performed according to the procedure described in Example 6 (step 6.9.). Starting with 0.50 g (1.01 mmol) of ethyl 5-{6-[5-(4-fluorophenyl)pyridin-2-yl]-6-azaspiro[3.4]oct-2-ylcarbamoyloxymethyl}isoxazole-3-carboxylate (isomer 7) and 25 mL of a solution (1M) of methylamine in tetrahydrofuran, at room temperature, 0.32 g of product is obtained in the form of a white solid.

m.p. (° C.): 194-196

LC-MS: M+H=480

¹H NMR (DMSO) δ (ppm): 8.70 (broad s, 1H), 8.38 (s, 1H); 7.80 (m, 2H); 7.60 (m, 2H); 7.23 (t, 2H); 6.78 (s, 1H); 6.48 (d, 1H); 5.18 (s, 2H); 4.08 (m, 1H); 3.45 (m, 2H), 3.40 (m, 2H); 2.78 (d, 3H), 2.25 (m, 2H); 2.00 (m, 4H).

EXAMPLE 14

Compound 19

3-(Methylcarbamoyl)isoxazol-5-ylmethyl[7-(6-chloroquinolin-2-yl)-7-azaspiro[3.5]non-2-yl]carbamate

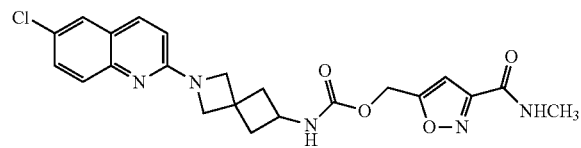 [SMILES: CNC(=O)c1cc(COC(=O)NC2CC3(C2)CN(c2ccc4cc(Cl)ccc4n2)C3)on1]

14.1 tert-Butyl 2-hydroxyimino-7-azaspiro[3.5]nonane-7-carboxylate 0.58 g (8.36 mmol) of hydroxylamine hydrochloride and 1.15 g (8.36 mmol) of potassium carbonate are added to a solution of 1.00 g (4.18 mmol) of tert-butyl 2-oxo-7-azaspiro[3.5]nonane-7-carboxylate (U.S. Pat. No. 6,498,159) in 60 mL of ethanol, and the mixture is then left stirring at room temperature for 12 hours. After evaporating off the solvent under reduced pressure, the residue is taken up in dichloromethane and water, the aqueous phase is separated out and extracted twice with dichloromethane, and the combined organic phases are dried over sodium sulfate. After evaporating off the solvent, the residue obtained is purified by chromatography on silica gel, eluting with a 99/1/0.1 mixture of dichloromethane, methanol and 28% aqueous ammonia. 0.831 g of pure product is thus obtained in the form of a white powder.

LC-MS: M+H=255 m.p. (° C.): 117-119

¹H NMR (CDCl₃) δ (ppm): 3.30 (m, 4H); 2.60 (d, 4H); 1.55 (m, 4H); 1.40 (s, 9H).

14.2 tert-Butyl 2-amino-7-azaspiro[3.5]nonane-7-carboxylate

To a solution of 0.50 g (1.97 mmol) of tert-butyl 2-hydroxyimino-7-azaspiro[3.5]nonane-7-carboxylate obtained in the preceding step, in 32 mL of a 7N solution of aqueous ammonia in methanol. 0.11 g (1.97 mmol) of Raney nickel is then added. The reaction medium is placed in a Parr flask under a hydrogen atmosphere (20 psi) at room temperature for 2 hours 30 minutes. The resulting mixture is filtered through a Büchner funnel and the filtrate is then concentrated under reduced pressure. The residue is taken up in dichloromethane and water, the aqueous phase is separated out and extracted twice with dichloromethane, and the combined organic phases are washed with saturated aqueous ammonium chloride solution and are then dried over sodium sulfate. After evaporating off the solvent, the residue obtained is purified by chromatography on silica gel, eluting with a 90/10/1 mixture of dichloromethane, methanol and 28% aqueous ammonia. 0.39 g of pure product is thus obtained in the form of a colourless oil.

LC-MS: M+H=241

$^1$H NMR (DMSO) δ (ppm): 3.40 (m, 1H); 3.30-3.10 (m, 4H); 2.25-2.15 (m, 2H); 1.70 (broad s, 2H); 1.50-1.35 (m, 6H); 1.30 (m, 9H).

14.3 tert-Butyl 2-ethoxycarbonylamino-7-azaspiro[3.5]nonane-7-carboxylate 4.96 g (45.77 mmol) of ethyl chloroformate are added to a solution containing 10.00 g (41.61 mmol) of tert-butyl 2-amino-7-azaspiro[3.5]nonane-7-carboxylate obtained in the preceding step, 13.44 g (104.02 mmol) of N,N-diisopropylethylamine and 0.51 g (4.16 mmol) of N,N-dimethylaminopyridine in 300 mL of 1,2-dichloroethane, cooled to about 0° C. Stirring is continued at 0° C. for 1 hour and then at room temperature for 12 hours. Water is added to the reaction medium, the aqueous phase is separated out and extracted several times with dichloromethane, the combined organic phases are washed with saturated aqueous ammonium chloride solution and dried over sodium sulfate, and the filtrate is concentrated under reduced pressure. After evaporating off the solvent, the residue obtained is purified by chromatography on silica gel, eluting with a 99/1/0.1 mixture of dichloromethane, methanol and 28% aqueous ammonia. 8.728 g of pure product are thus obtained in the form of a brown oil.

LC-MS: M+H=313

$^1$H NMR (CDCl$_3$) δ (ppm): 4.80 (broad s, 1H); 4.10 (m, 3H); 3.30 (m, 4H); 2.30 (m, 2H); 1.60 (m, 6H); 1.50 (s, 9H); 1.25 (t, 3H).

14.4 Ethyl(7-azaspiro[3.5]non-2-yl)carbamate hydrochloride

The process is performed according to the procedure described in Example 2 (step 2.5.). Starting with 8.63 g (27.62 mmol) of tert-butyl 2-ethoxycarbonylamino-7-azaspiro[3.5]nonane-7-carboxylate obtained in the preceding step and 27.62 mL (110.50 mmol) of a 4N solution of hydrochloric acid in dioxane, and after filtration through a sinter funnel and washing with ether, 5.18 g of product are obtained in hydrochloride form.

LC-MS: M+H=249 m.p. (° C.): 238-240

$^1$H NMR (DMSO) δ (ppm): 8.80 (broad s, 1H); 7.40 (d, 1H); 3.90 (m, 3H); 2.80 (m, 4H); 2.10 (m, 2H); 1.60 (m, 6H); 1.25 (t, 3H).

14.5 Ethyl[7-(6-chloroquinolin-2-yl)-7-azaspiro[3.5]non-2-yl]carbamate 0.166 g (0.78 mmol) of ethyl(7-azaspiro[3.5]non-2-yl)carbamate, obtained in the preceding step and used in base form, 0.155 g (0.78 mmol) of 2-chloro-6-chloroquinoline and 0.113 g (0.82 mmol) of potassium carbonate in 2 mL of DMSO are placed in a sealed tube. The mixture is then heated at 130° C. for 12 hours. The reaction mixture is allowed to cool to room temperature and is then taken up in dichloromethane and water. The aqueous phase is separated out and extracted twice with dichloromethane, the combined organic phases are washed with saturated aqueous ammonium chloride solution and dried over sodium sulfate, and the filtrate is concentrated under reduced pressure. After evaporating off the solvent, the residue obtained is purified by chromatography on silica gel, eluting with a 98/2/0.2 mixture of dichloromethane, methanol and 28% aqueous ammonia. 0.151 g of pure product is thus obtained in the form of a powder.

LC-MS: M+H=374 m.p. (° C.): 137-139

$^1$H NMR (CDCl$_3$) δ (ppm): 7.80 (d, 1H); 7.70 (m, 1H); 7.60 (m, 1H); 7.50 (m, 1H); 7.10 (d, 1H); 4.80 (broad s, 1H); 4.20 (m, 3H); 3.70 (m, 4H); 2.50 (m, 2H); 1.90-1.60 (m, 6H); 1.30 (t, 3H).

14.6 7-(6-Chloroquinolin-2-yl)-7-azaspiro[3.5]non-2-ylamine 0.726 g (12.95 mmol) of potassium hydroxide is added, at room temperature, to a solution of 0.242 g (0.65 mmol) of ethyl[7-(6-chloroquinolin-2-yl)-7-azaspiro[3.5]non-2-yl]carbamate, obtained in step 12.5., in 3.25 mL of ethanol/water (1/1). The mixture is then heated at 110° C. for 12 hours. 0.363 g (6.47 mmol) of potassium hydroxide is added and the mixture is left stirring for 3 hours. The resulting mixture is allowed to cool to room temperature and is then concentrated under reduced pressure. The residue is taken up in dichloromethane and 1N hydrochloric acid solution. The acidic aqueous phase is washed with dichloromethane and then basified with aqueous 1N sodium hydroxide solution, which is extracted several times with dichloromethane. The combined organic phases are then dried over sodium sulfate and the filtrate is concentrated under reduced pressure. 0.188 g of expected product is thus obtained in the form of an oil.

LC-MS: M+H=302

$^1$H NMR (DMSO) δ (ppm): 8.00 (d, 1H); 7.80 (d, 1H); 7.50 (m, 2H); 7.30 (d, 1H); 3.60 (m, 4H); 3.30 (m, 2H); 2.10 (m, 2H); 1.50-1.30 (m, 6H).

14.7 3-(Methylcarbamoyl)isoxazol-5-ylmethyl[7-(6-chloroquinolin-2-yl)-7-azaspiro[3.5]non-2-yl]carbamate The process is performed according to the procedure described in Example 1, step 1.1. Starting with 0.181 g (0.60 mmol) of 7-(6-chloroquinolin-2-yl)-7-azaspiro[3.5]non-2-ylamine, described in the preceding step (step 12.6.), 0.231 g (0.72 mmol) of 3-methylcarbamoylisoxazol-5-ylmethyl 4-nitrophenyl carbonate, obtained in step 4.1., 0.194 g (1.50 mmol) of N,N-diisopropylethylamine and 0.037 g (0.30 mmol) of N,N-dimethylaminopyridine in 6 mL of 1-2 dichloroethane, and after crystallization from ether, the product is filtered off on a sinter funnel, rinsed with ether and dried under vacuum at about 70° C. 0.220 g of pure product is thus obtained in the form of a white powder.

LC-MS: M+H=484 m.p. (° C.): 194-196

$^1$H NMR (DMSO) δ (ppm): 8.70 (broad s, 1H); 8.00 (d, 1H); 7.80 (m, 2H); 7.50 (m, 2H); 7.30 (d, 1H); 6.80 (s, 1H);

5.20 (s, 2H); 4.10 (m, 1H); 3.75-3.55 (m, 4H); 2.80 (s, 3H); 2.20 (m, 2H); 1.70 (m, 2H); 1.70-1.50 (m, 4H).

EXAMPLE 15

Compound 31

3-Carbamoylisoxazol-5-ylmethyl[7-(5-isobutylpyridin-2-yl)-7-azaspiro[3,5]non-2-yl]carbamate

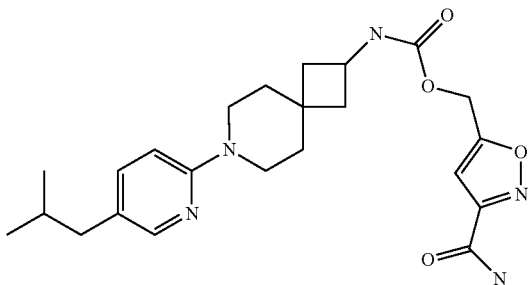 [SMILES: CC(C)Cc1ccc(N2CCC3(CC2)CC(NC(=O)OCc2cc(C(N)=O)no2)C3)nc1]

15.1. Ethyl[7-(5-bromopyridin-2-yl)-7-azaspiro[3.5]non-2-yl]carbamate 0.60 g (2.41 mmol) of ethyl(7-azaspiro[3.5]non-2-yl)carbamate hydrochloride, obtained in step 14.4. (Example 14), 0.57 g (2.41 mmol) 2,5-dibromopyridine and 0.70 g (5.07 mmol) of potassium carbonate in 2 mL of dimethyl sulfoxide are placed in a sealed tube. The mixture is then heated at 130° C. for 15 hours. The reaction medium is allowed to cool to room temperature and then taken up in saturated sodium chloride solution and extracted with dichloromethane, and the combined organic phases are dried over sodium sulfate. After evaporating off the solvent, the residue obtained is purified by chromatography on preparative plates, eluting with a 100/0/0 to 99/1/0.1 mixture of dichloromethane, methanol and 28% aqueous ammonia.

0.75 g of pure product is thus obtained in the form of a powder.

m.p. (° C.): 113-115° C.

15.2 Ethyl{7-[5-(2-methyl-propenyl)pyridin-2-yl]-7-azaspiro[3.5]non-2-yl}carbamate The process is performed according to the method described in Example 2 (step 2.7.). Starting with 0.50 g (1.36 mmol) of ethyl[7-(5-bromopyridin-2-yl)-7-azaspiro[3.5]non-2-yl]carbamate, prepared in the preceding step, 0.33 mL (1.63 mmol) of pinacol 2-methyl-1-propenylboronate (commercial) and 1.33 g (4.07 mmol) of caesium carbonate, suspended in 9 mL of a 9/1 mixture of tetrahydrofuran and water, and 0.11 g (0.14 mmol) of $PdCl_2dppf.CH_2Cl_2$, and after purifying on a column of silica gel, eluting with a 100/0/0 to 99/1/0.1 mixture of dichloromethane, methanol and 28% aqueous ammonia, 0.39 g of expected product is obtained in the form of a wax.

15.3 Ethyl[7-(5-isobutylpyridin-2-yl)-7-azaspiro[3.5]non-2-yl]carbamate 0.05 g (0.45 mmol) of palladium-on-charcoal is added to a solution of 0.37 g (1.08 mmol) of ethyl{7-[5-(2-methylpropenyl)pyridin-2-yl]-7-azaspiro[3.5]non-2-yl}carbamate obtained in the preceding step, in 15 mL of methanol. The reaction medium is placed in a Parr flask under a hydrogen atmosphere (10 psi) at room temperature for 2 hours. The resulting mixture is filtered through a Büchner funnel and the filtrate is then concentrated under reduced pressure. 0.37 g of expected product is thus obtained in the form of a yellow wax.

15.4 7-(5-Isobutylpyridin-2-yl)-7-azaspiro[3.5]non-2-ylamine 1.21 g (21.65 mmol) of potassium hydroxide are added, at room temperature, to a solution of 0.37 g (1.08 mmol) of ethyl[7-(5-isobutylpyridin-2-yl)-7-azaspiro[3.5]non-2-yl]carbamate in 5 mL of ethanol/water (1/1). The mixture is then heated at 110° C. for 15 hours. The resulting mixture is allowed to cool to room temperature and is then concentrated under reduced pressure. The reaction medium is taken up in saturated sodium chloride solution and dichloromethane, the aqueous phase is separated out and extracted with dichloromethane, and the combined organic phases are dried over sodium sulfate. After evaporating under reduced pressure and purifying on a column of silica gel, eluting with a 100/0/0 to 96/4/0.4 mixture of dichloromethane, methanol and 28% aqueous ammonia, 0.27 g of expected product is obtained in the form of a wax.

LC-MS: M+H=274

$^1$H NMR (CDCl$_3$) δ (ppm): 8.00 (s, 1H); 7.30 (d, 1H); 6.60 (d, 1H); 3.50 (m, 3H); 3.40 (m, 2H); 2.30 (m, 4H); 1.80 (m, 1H); 1.70 (m, 4H); 1.50 (m, 4H); 0.90 (d, 6H).

15.5 3-Carbamoylisoxazol-5-ylmethyl 4-nitrophenyl carbonate 2.84 g (14.07 mmol) of 4-nitrophenyl chloroformate are added portionwise to a solution of 2.00 g (14.07 mmol) of 3-carbamoylisoxazol-5-ylmethanol, 1.71 mL (21.11 mmol) of pyridine and 0.17 g (1.41 mmol) of N,N-dimethylaminopyridine in 15 mL of dichloromethane, cooled to about 0° C. The medium is stirred at 0° C. for 1 hour and then at room temperature for 1 hour. The precipitate formed is filtered off and then rinsed thoroughly with diisopropyl ether. After drying under vacuum at about 60° C., 3.12 g of expected product are obtained in the form of a white solid, which is used without further purification in the following step.

m.p. (° C.): 143-145

$^1$H NMR (DMSO, 400 MHz) δ (ppm): 8.40 (d, 2H); 8.25 (broad s, 1H); 7.90 (broad s, 1H); 7.65 (d, 2H); 7.0 (s, 1H); 5.50 (s, 2H).

15.6 3-Carbamoylisoxazol-5-ylmethyl[7-(5-isobutylpyridin-2-yl)-7-azaspiro[3.5]non-2-yl]carbamate The process is performed according to the procedure described in Example 1, step 1.1. Starting with 0.26 g (0.95 mmol) of 7-(5-isobutylpyridin-2-yl)-7-azaspiro[3.5]non-2-ylamine, obtained in step 15.4, 0.35 g (1.15 mmol) of 3-carbamoylisoxazol-5-ylmethyl 4-nitrophenyl carbonate, obtained in step 15.5, 0.42 mL (2.39 mmol) of N,N-diisopropylethylamine and 0.06 g (0.48 mmol) of N,N-dimethylaminopyridine, in 9 mL of 1,2-dichloroethane, 0.35 g of pure product is obtained in the form of a white powder.

m.p. (° C.): 178-180° C.

LC-MS: M+H=442

$^1$H NMR (DMSO) δ (ppm): 8.15 (m, 1H); 7.90 (m, 1H); 7.85 (m, 1H); 7.75 (m, 1H); 7.30 (m, 1H); 6.75 (m, 2H); 5.20

(s, 2H); 4.00 (m, 1H); 3.40 (m, 2H); 3.35 (m, 2H); 2.30 (m, 2H); 2.20 (m, 2H); 1.75 (m, 3H); 1.55 (m, 4H); 0.85 (d, 6H).

EXAMPLE 16

Compound 40

3-Carbamoylisoxazol-5-ylmethyl[6-(4-trifluoromethylpyrimidin-2-yl)-6-azaspiro[2.5]oct-1-yl]carbamate 16.1 tert-Butyl 1-benzyloxycarbonylamino-6-azaspiro[2.5]octane-6-carboxylate 5.00 q (19.58 mmol) of 6-tert-butyl 6-azaspiro[2.5]octane-1,6-dicarboxylate (commercial) are dissolved in 11 mL of toluene, and 2.99 mL (21.54 mmol) of triethylamine and 4.66 mL (21.54 mmol) of diphenylphosphonic azide are then added, at 0° C. under argon. The mixture is allowed to warm to room temperature, and is stirred for 1 hour 30 minutes at 110° C. Benzyl alcohol (2.23 mL; 21.54 mmol) is then added and the mixture is stirred at 110° C. for 15 hours.

After cooling to room temperature, saturated sodium hydrogen carbonate solution is added, the mixture is extracted with diethyl ether and the combined organic phases are then washed successively with saturated sodium hydrogen carbonate solution and then with saturated sodium chloride solution. The organic phase is dried over sodium sulfate. After evaporating under reduced pressure and purifying on a column of silica gel, eluting with a 100/0/0 to 98/2/0.2 mixture of dichloromethane, methanol and 28% aqueous ammonia, 5.50 g of expected product are obtained in the form of an oil.

LC-MS: M+H=361
$^1$H NMR (DMSO) δ (ppm): 7.40 (m, 5H); 5.10 (s, 2H); 3.45-3.20 (m, 4H); 2.40 (m, 1H); 1.40 (s, 9H); 1.30 (m, 3H), 1.20 (m, 1H); 1.75 (m, 1H); 1.45 (m, 1H).

16.2 Benzyl(6-azaspiro[2.5]oct-1-yl)carbamate

The process is performed according to the procedure described in Example 2 (step 2.5.). Starting with 5.50 g (15.28 mmol) of tert-butyl 1-benzyloxycarbonylamino-6-azaspiro[2.5]octane-6-carboxylate obtained in the preceding step and 15.28 mL (61.10 mmol) of a 4N solution of hydrochloric acid in dioxane, and after basic extraction, 3.56 g of product are obtained in the form of a pale yellow powder.

LC-MS: M+H=261
m.p. (° C.): 223-225
$^1$H NMR (DMSO) δ (ppm): 7.40 (m, 6H); 5.10 (s, 2H); 3.00 (m, 3H); 2.40 (m, 2H); 1.60 (m, 1H); 1.40 (m, 3H); 1.70-1.40 (m, 2H).

16.3 Benzyl[6-(4-trifluoromethylpyrimidin-2-yl)-6-azaspiro[2.5]oct-1-yl]carbamate 0.60 g (2.30 mmol) of benzyl(6-azaspiro[2.5]oct-1-yl)carbamate obtained in the preceding step, 0.36 mL (3.00 mmol) of 2-chloro-4-trifluoromethylpyrimidine and 0.80 mL (4.61 mmol) of diisopropylethylmaine in 17 mL of acetonitrile and 3 mL of dimethylformamide are placed in a round-bottomed flask. The mixture is then heated at 95° C. for 15 hours. The reaction mixture is allowed to cool to room temperature and then taken up in dichloromethane and water. The aqueous phase is separated out and extracted twice with dichloromethane, the combined organic phases are washed with saturated aqueous ammonium chloride solution and dried over sodium sulfate, and the filtrate is concentrated under reduced pressure. After evaporating off the solvent, the residue obtained is purified by chromatography on silica gel, eluting with a 100/0/0 to 99/1/0.1 mixture of dichloromethane, methanol and 28% aqueous ammonia. 0.88 g of product is thus obtained in the form of an oil.

LC-MS: M+H=407
$^1$H NMR (CDCl$_3$) δ (ppm): 8.70 (d, 1H); 7.50 (m, 1H); 7.40 (m, 4H); 7.20 (m, 1H); 7.00 (d, 1H); 5.10 (s, 2H); 3.95 (m, 2H); 3.70 (m, 2H); 2.50 (m, 1H); 1.50 (m, 2H); 1.30 (m, 2H); 1.75 (m, 1H); 1.50 (m, 1H)

16.4 6-(4-Trifluoromethylpyrimidin-2-yl)-6-azaspiro[2.5]oct-1-ylamine

The process is performed according to the procedure described in Example 2 (step 2.5.). Starting with 0.86 g (2.13 mmol) of benzyl[6-(4-trifluoromethylpyrimidin-2-yl)-6-azaspiro[2.5]oct-1-yl]carbamate obtained in the preceding step and 3.74 mL (21.33 mmol) of a solution of 35% hydrobromic acid in acetic acid, and after basic extraction and uptake in diethyl ether, 0.32 g of product is obtained in the form of a white powder.

m.p. (° C.): 243-245° C.
LC-MS: M+H=273
$^1$H NMR (DMSO) δ (ppm): 8.70 (d, 1H); 8.15 (broad s, 2H); 7.00 (d, 1H); 4.10 (m, 1H); 4.00 (m, 1H); 3.70 (m, 2H); 2.50 (m, 1H); 1.70 (m, 2H); 1.50 (m, 1H); 1.35 (m, 1H); 1.90 (m, 1H); 1.80 (m, 1H).

16.5 3-Carbamoylisoxazol-5-ylmethyl[6-(4-trifluoromethylpyrimidin-2-yl)-6-azaspiro[2.5]oct-1-yl]carbamate The process is performed according to the procedure described in Example 1, step 1.1. Starting with 0.15 g (0.55 mmol) of 6-(4-trifluoromethylpyrimidin-2-yl)-6-azaspiro[2.5]oct-1-ylamine, obtained in step 16.4, 0.20 g (0.66 mmol) of 3-carbamoylisoxazol-5-ylmethyl 4-nitrophenyl carbonate, obtained in step 15.5, 0.24 mL (1.38 mmol) of N,N-diisopropylethylamine and 0.03 g (0.28 mmol) of N,N-dimethylaminopyridine, in 5 mL of 1,2-dichloroethane, 0.15 g of pure product is obtained in the form of a white powder after purification by chromatography on silica gel, eluting with a 100/0/0 to 98/2/0.2 mixture of dichloromethane, methanol and 28% aqueous ammonia.

m.p. (° C.): 183-185° C.
LC-MS: M+H=441
$^1$H NMR (DMSO) δ (ppm): 8.70 (d, 1H); 8.15 (broad s, 1H); 7.85 (broad s, 1H); 7.70 (broad s, 1H); 7.00 (d, 1H); 6.80 (s, 1H); 5.20 (s, 2H); 3.90 (m, 2H); 3.75 (m, 2H); 2.50 (m, 1H); 1.40 (m, 3H); 1.30 (m, 1H); 1.70 (m, 1H); 1.50 (m, 1H)

Table 1 that follows illustrates the chemical structures and physical properties of a few compounds according to the invention. In this table:

all the compounds are in free base form;
compounds 10 and 11 are mixtures of isomers. Compound 12 is in the form of isomer I, whereas compound 13 is in the form of isomer II. Compound 17 is in the form of isomer I, whereas compound 18 is in the form of isomer II. Compounds 16, 21 and 22 are in the form of an isomer. These isomers correspond to positional isomers of the chain -A-NH— relative to the chain —(CH$_2$)$_n$—N—.
the "m.p. (° C.)" column gives the melting points of the products in degrees Celsius (° C.).
Compound 26 is in salt form.

TABLE 1

(I)

| No. | R₁ | m | n | o | p | A | R₂ | R₃ | R₄ | m.p. (° C.) |
|---|---|---|---|---|---|---|---|---|---|---|
| 1. | 6-fluoroquinolin-2-yl | 2 | 2 | 1 | 1 | bond | H | H | thiazol-4-yl | 107-109° C. |
| 2. | 6-fluoroquinolin-2-yl | 2 | 2 | 1 | 1 | bond | H | H | isoxazole-3-carboxamide | 226-228° C. |
| 3. | 5-(trifluoromethyl)pyridin-2-yl | 2 | 2 | 1 | 1 | bond | H | H | isoxazole-3-carboxamide | 167-169° C. |
| 4. | 5-bromopyridin-2-yl | 2 | 2 | 1 | 1 | bond | H | H | isoxazole-3-carboxamide | 165-167° C. |
| 5. | 5-(4-fluorophenyl)pyridin-2-yl | 2 | 2 | 1 | 1 | bond | H | H | isoxazole-3-carboxamide | 216-218° C. |
| 6. | 6-fluoroquinolin-2-yl | 2 | 2 | 1 | 1 | CH₂ | H | H | isoxazole-3-carboxamide | 190-192° C. |
| 7. | 6-fluoroquinolin-2-yl | 2 | 2 | 1 | 1 | CH₂ | H | H | isoxazole-3-carboxamide N-methyl | 134-136° C. |
| 8. | 5-(4-fluorophenyl)pyridin-2-yl | 2 | 2 | 1 | 1 | bond | H | H | isoxazole-3-carboxamide N-methyl | 219-221° C. |
| 9. | 6-fluoroquinolin-2-yl | 2 | 2 | 1 | 1 | bond | H | H | isoxazole-3-carboxamide N-methyl | 193-195° C. |

TABLE 1-continued (I)

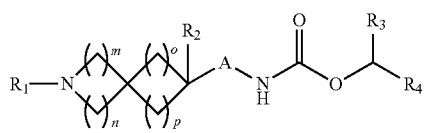

| No. | R₁ | m | n | o | p | A | R₂ | R₃ | R₄ | m.p. (°C.) |
|---|---|---|---|---|---|---|---|---|---|---|
| 10. | 4-fluorophenyl-pyridinyl | 2 | 1 | 1 | 1 | bond | H | H | isoxazole-C(O)NHCH₃ | 216-218° C. |
| 11. | 4-fluorophenyl-pyridinyl | 2 | 1 | 1 | 1 | bond | H | H | isoxazole-C(O)NHCH₃ | 184-186° C. |
| 12. | 4-fluorophenyl-pyridinyl | 2 | 1 | 1 | 1 | CH₂ | H | H | isoxazole-C(O)NHCH₃ isomer I | 171-173° C. |
| 13. | 4-fluorophenyl-pyridinyl | 2 | 1 | 1 | 1 | CH₂ | H | H | isoxazole-C(O)NHCH₃ isomer II | 180-182° C. |
| 14. | 6-fluoroquinolinyl | 2 | 2 | 1 | 1 | bond | H | H | oxazole-C(O)NH₂ | 188-190° C. |
| 15. | 6-fluoroquinolinyl | 1 | 1 | 1 | 1 | bond | H | H | isoxazole-C(O)NHCH₃ | 167-169° C. |
| 16. | 6-fluoroquinolinyl | 2 | 1 | 1 | 1 | CH₂ | H | H | 5-methyl-isoxazole-C(O)NHCH₃ | 102-104° C. |
| 17. | 4-fluorophenyl-pyridinyl | 2 | 1 | 1 | 1 | bond | H | H | isoxazole-C(O)NHCH₃ isomer I | 203-205° C. |

TABLE 1-continued (I)

$$R_1-N\overset{(\phantom{)}_m}{\underset{(\phantom{)}_n}{)}}\overset{R_2}{\underset{(\phantom{)}_p}{)}}-A-NH-C(=O)-O-CHR_3R_4$$

| No. | R₁ | m | n | o | p | A | R₂ | R₃ | R₄ | m.p. (° C.) |
|---|---|---|---|---|---|---|---|---|---|---|
| 18. | 4-fluorophenyl-pyridin-2-yl | 2 | 1 | 1 | 1 | bond | H | H | 5-(N-methylcarbamoyl)isoxazol-3-yl (isomer II) | 194-196° C. |
| 19. | 6-chloroquinolin-2-yl | 2 | 2 | 1 | 1 | bond | H | H | 5-(N-methylcarbamoyl)isoxazol-3-yl | 194-196° C. |
| 20. | 4-fluorophenyl-pyridin-2-yl | 1 | 1 | 1 | 1 | bond | H | H | 5-carbamoylisoxazol-3-yl | 239-241° C. |
| 21. | 5-bromopyridin-2-yl | 2 | 1 | 1 | 1 | bond | H | H | 5-(N-methylcarbamoyl)isoxazol-3-yl | 175-177° C. |
| 22. | 4-(trifluoromethyl)pyridin-2-yl | 2 | 1 | 1 | 1 | bond | H | H | 5-(N-methylcarbamoyl)isoxazol-3-yl | 167-170° C. |
| 23. | 4-fluorophenyl-pyridin-2-yl | 1 | 1 | 1 | 1 | bond | H | H | 5-(N-methylcarbamoyl)isoxazol-3-yl | 218-220° C. |
| 24. | 4-(trifluoromethyl)pyrimidin-2-yl | 2 | 2 | 1 | 1 | bond | H | H | 5-(N-methylcarbamoyl)isoxazol-3-yl | 153-155° C. |
| 25. | 5-(4-fluorophenyl)pyrazin-2-yl | 2 | 2 | 1 | 1 | bond | H | H | 5-carbamoylisoxazol-3-yl | 145-147° C. |

TABLE 1-continued (I)

| No. | R₁ | m | n | o | p | A | R₂ | R₃ | R₄ | m.p. (°C.) |
|---|---|---|---|---|---|---|---|---|---|---|
| 26. | 4-(trifluoromethyl)pyrimidin-2-yl | 2 | 2 | 1 | 1 | bond | H | H | isoxazole-3-C(O)NH-CH₂CH₂-N(CH₃)₂ | 147-150° C. |
| 27. | 4-(4-fluorophenyl)pyridin-2-yl | 2 | 2 | 1 | 1 | bond | H | H | isoxazole-3-C(O)NH₂ | 162-164° C. |
| 28. | 4-chloropyridin-2-yl | 2 | 2 | 1 | 1 | bond | H | H | isoxazole-3-C(O)NH₂ | 164-166° C. |
| 29. | 4-(trifluoromethyl)pyridin-2-yl | 2 | 2 | 1 | 1 | bond | H | H | isoxazole-3-C(O)NH₂ | 162-164° C. |
| 30. | 5-(3-fluorophenyl)pyridin-2-yl | 2 | 2 | 1 | 1 | bond | H | H | isoxazole-3-C(O)NH₂ | 214-216° C. |
| 31. | 5-isobutylpyridin-2-yl | 2 | 2 | 1 | 1 | bond | H | H | isoxazole-3-C(O)NH₂ | 178-180° C. |
| 32. | 6-chloroquinolin-2-yl | 2 | 2 | 1 | 1 | bond | H | H | isoxazole-3-C(O)NH₂ | 216-218° C. |
| 33. | 6-chloroquinolin-2-yl | 2 | 2 | 1 | 1 | CH₂ | H | H | isoxazole-3-C(O)NHCH₃ | 179-181° C. |

TABLE 1-continued (I)

| No. | R₁ | m | n | o | p | A | R₂ | R₃ | R₄ | m.p. (° C.) |
|---|---|---|---|---|---|---|---|---|---|---|
| 34. | 4-(trifluoromethyl)pyridin-2-yl | 2 | 2 | 1 | 1 | bond | H | H | 5-(N-methylcarbamoyl)isoxazol-3-yl | 116-118° C. |
| 35. | 4-(trifluoromethyl)pyridin-2-yl | 2 | 2 | 1 | 1 | bond | H | H | 3-(4-fluorophenyl)-1,2,4-oxadiazol-5-yl | 103.5-105.5° C. |
| 36. | 4-(trifluoromethyl)pyridin-2-yl | 2 | 2 | 1 | 1 | bond | H | H | 4-carbamoyloxazol-2-yl | 153.5-155.5° C. |
| 37. | 4-(trifluoromethyl)pyridin-2-yl | 2 | 2 | 1 | 1 | bond | H | H | 5-methyl-3-phenylisoxazol-4-yl | 115.6-117.6° C. |
| 38. | 4-(trifluoromethyl)pyridin-2-yl | 2 | 2 | 1 | 1 | bond | H | H | 3-ethyl-1,2,4-oxadiazol-5-yl | 87.6-89.6° C. |
| 39. | 4-(trifluoromethyl)pyridin-2-yl | 2 | 2 | 1 | 1 | bond | H | H | 5-methyl-1,2,4-oxadiazol-3-yl | 66-68° C. |
| 40. | 4-(trifluoromethyl)pyrimidin-2-yl | 2 | 2 | 1 | 0 | bond | H | H | 5-carbamoylisoxazol-3-yl | 183-185 |

TABLE 1-continued (I)

| No. | R₁ | m | n | o | p | A | R₂ | R₃ | R₄ | m.p. (°C.) |
|---|---|---|---|---|---|---|---|---|---|---|
| 41. | 4-(trifluoromethyl)pyrimidin-2-yl | 2 | 2 | 1 | 0 | bond | H | H | 5-(N-methylcarbamoyl)isoxazol-3-yl | 165-167 |

Table 2 that follows gives the results of the ¹H NMR analyses for the compounds of Table 1.

TABLE 2

| No. | ¹H NMR (DMSO or CDCl₃ 400 MHZ) δ (ppm) |
|---|---|
| 1 | 8.80 (s, 1H); 7.80 (d, 1H); 7.60 (m, 1H); 7.35 (s, 1H); 7.30-7.15 (m, 2H); 7.00 (d, 1H); 5.30 (s, 2H); 4.90 (broad s, 1H); 4.20 (m, 1H); 3.70-3.50 (m, 4H); 2.35 (t, 2H); 1.80-1.60 (m, 6H). |
| 2 | 8.15 (broad s, 1H); 8.00 (d, 1H); 7.85 (broad s, 1H); 7,70 (d, 1H); 7.60 (m, 1H); 7.50 (m, 1H); 7.40 (m, 1H); 7.30 (d, 1H); 6.70 (s, 1H); 5.20 (s, 2H); 4.10 (m, 1H); 3.70-3.50 (m, 4H); 2.35 (t, 2H); 1.80 (t, 2H); 1.70-1.40 (m, 4H). |
| 3 | 8.40 (s, 1H); 8.20 (broad s, 1H); 7.90 (broad s, 1H); 7.80 (m, 2H); 7.00 (d, 1H); 6.80 (s, 1H); 5.25 (s, 2H); 4.10 (m, 1H); 3.70-3.50 (m, 4H); 2.35 (t, 2H); 1.80 (t, 2H); 1.70-1.40 (m, 4H). |
| 4 | 8.10 (s, 2H); 7.80 (s, 1H); 7.70 (d, 1H); 7.60 (d, 1H); 6.85 (d, 1H); 6.75 (s, 1H); 5.20 (s, 2H); 4.00 (m, 1H); 3.55 (t, 2H); 3.45 (t, 2H); 2.20 (m, 2H); 1.75 (m; 2H); 1.65-1.45 (m, 4H). |
| 5 | 8.40 (s, 1H); 8.20 (broad s, 1H); 7.90-7.70 (m, 3H); 7.60 (m, 2H); 7.25 (m, 2H); 6.90 (d, 1H); 6.75(s, 1H); 5.20 (s, 2H); 4.00 (m, 1H); 3.55 (t, 2H); 3.45 (t, 2H); 2.20 (m, 2H); 1.75 (m; 2H); 1.65-1.45 (m, 4H). |
| 6 | 8.15 (broad s, 1H); 8.0 (d, 1H); 7.85 (broad s, 1H); 7.60-7.35 (m, 4H); 7.25 (m, 1H); 6.75 (s, 1H); 5.20 (s, 2H); 3.70 (t, 2H); 3.60 (t, 2H); 3.10 (t, 2H); 2.40 (m, 1H); 1.90 (t, 2H); 1.70 (m, 2H); 1.60 (m, 4H). |
| 7 | 8.70 (broad s, 1H); 8.00 (d, 1H); 7.60 (m, 1H); 7.50 (m, 2H); 7.40 (m, 1H); 7.30 (d, 1H); 6.75 (s, 1H); 5.20 (s, 2H); 3.70 (t, 2H); 3.60 (t, 2H); 3.10 (t, 2H); 2.80 (s, 3H); 2.40 (m, 1H); 1.90 (t, 2H); 1.60 (m, 2H); 1.50 (m, 4H). |
| 8 | 8.70 (broad s, 1H); 8.40 (s, 1H); 7.90-7.70 (m, 2H); 7.65 (m, 2H); 7.25 (m, 2H); 6.90 (d, 1H); 6.80(s, 1H); 5.20 (s, 2H); 4.00 (m, 1H); 3.55 (t, 2H); 3.45 (t, 2H); 2.80 (s, 3H); 2.20 (m, 2H); 1.75 (m; 2H); 1.65-1.45 (m, 4H). |
| 9 | 8.70 (broad s, 1H); 8.00 (d, 1H); 7.85 (d, 1H); 7.70 (m, 1H); 7.60 (m, 1H); 7.50 (m, 1H); 7.40 (m, 1H); 6.80 (s, 1H); 5.20 (s, 2H); 4.10 (m, 1H); 3.70-3.50 (m, 4H); 2.80(s, 3H); 2.20 (t, 2H); 1.70 (t, 2H); 1.70-1.50 (m, 4H). |
| 10 | 8.40 (s, 1H); 8.20 (broad s, 1H); 7.80 (broad s, 3H); 7.60 (s, 2H); 7.30 (m, 2H); 6.80 (s, 1H); 6.50 (t, 1H); 5.20 (s, 2H); 4.10 (m, 1H); 3.50-3.30 (m, 4H); 2.30 (m, 2H); 2.00 (m, 4H). |
| 11 | 8.70 (s, 1H); 8.40 (s, 1H); 7.80 (m, 2H); 7.60 (m, 2H); 7.30 (m, 2H); 6.80 (s, 1H); 6.50 (t, 1H); 5.20 (s, 2H); 4.10 (m, 1H); 3.50-3.30 (m, 4H); 2.80 (s, 3H); 2.30 (m, 2H); 2.00 (m, 4H). |
| 12 | 8.70 (broad s, 1H); 8.40 (s, 1H); 7.80 (m, 1H); 7.60 (m, 2H); 7.50 (m, 1H); 7.30 (m, 2H); 6.80 (s, 1H); 6.50 (d, 1H); 5.20 (s, 2H); 3.50 (m, 2H); 3.35 (m, 2H); 3.10 (t, 2H) 2.80 (s, 3H); 2.40 (m, 1H); 2.00 (m, 4H); 1.80 (m, 2H). |
| 13 | 8.70 (broad s, 1H); 8.40 (s, 1H); 7.80 (m, 1H); 7.60 (m, 2H); 7.50 (m, 1H); 7.30 (m, 2H); 6.80 (s, 1H); 6.50 (d, 1H); 5.20 (s, 2H); 3.50 (s, 2H); 3.40 (m, 2H); 3.10 (t, 2H); 2.80 (s, 3H); 2.40 (m, 1H); 2.10 (t, 2H); 1.90 (t, 2H) 1.80 (t, 2H). |
| 14 | 8.60 (s, 1H); 8.00 (d, 1H); 7.80 (d, 1H); 7.70 (broad s, 1H); 7.60 (m, 1H); 7.50 (m, 2H); 7.40 (m, 1H); 7.30 (d, 1H); 5.10 (s, 2H); 4.10 (m, 1H); 3.70-3.50 (m, 4H); 2.35 (m, 2H); 1.80 (t, 2H); 1.70-1.40 (m, 4H). |
| 15 | 8.70 (broad s, 1H); 8.05 (d, 1H); 7.80 (d, 1H); 7.60 (m, 1H); 7.50 (m, 1H); 7.40 (m, 1H); 6.80 (s, 1H); 6.75 (s, 1H); 5.25 (s, 2H); 4.15 (s, 2H); 4.05 (s, 2H); 3.95 (m, 1H); 2.80(s, 3H); 2.50 (t, 2H); 2.20 (t, 2H). |
| 16 | 8.70 (broad s, 1H); 8.00 (d, 1H); 7.55 (m, 3H); 7.40 (m, 1H); 6.90 (d, 1H); 6.80 (s, 1H); 5.20 (s, 2H); 3.55 (t, 2H); 3.45 (s, 2H); 3.10 (t, 2H); 2.75 (s, 3H); 2.45 (m, 1H); 2.02 (m, 4H); 1.80 (m, 2H). |
| 17 | 8.70 (broad s, 1H), 8.40 (s, 1H); 7.81 (m, 2H); 7.62 (m, 2H); 7.25 (t, 2H); 6.78 (s, 1H); 6.50 (d, 1H); 5.20 (s, 2H); 4.08 (m, 1H); 3.50 (s, 2H), 3.40 (m, 2H); 2.78 (s, 3H), 2.30 (m, 2H); 1.99 (m, 4H). |
| 18 | 8.70 (broad s, 1H); 8.38 (s, 1H); 7.80 (m, 2H); 7.60 (m, 2H); 7.23 (t, 2H); 6.78 (s, 1H); 6.48 (d, 1H); 5.18 (s, 2H); 4.08 (m, 1H); 3.45 (m, 2H), 3.40 (m, 2H); 2.78 (d, 3H), 2.25 (m, 2H); 2.00 (m, 4H). |
| 19 | 8.70 (broad s, 1H); 8.00 (d, 1H); 7.80 (m, 2H); 7.50 (m, 2H); 7.30 (d, 1H); 6.80 (s, 1H); 5.20 (s, 2H); 4.10 (m, 1H); 3.75-3.55 (m, 4H); 2.80 (s, 3H); 2.20 (m, 2H); 1.70 (m, 2H); 1.70-1.50 (m, 4H). |
| 20 | 8.40 (s, 1H); 8.15 (broad s, 1H); 7.80 (m, 3H); 7.65 (m, 2H); 7.25 (m, 2H); 6.80 (s, 1H); 6.40 (d, 1H); 5.20 (s, 2H); 4.00 (m, 2H); 3.90 (m, 3H); 2.50 (m, 2H); 2.15 (m, 2H) |
| 21 | 8.70 (broad s, 1H); 8.10 (s, 1H); 7.80 (dl, 1H); 7.60 (d, 1H); 6.80 (s, 1H); 6.40 (d, 1H); 5.20 (s, 2H); 4.05 (m, 1H); 3.40 (m, 2H); 3.30 (m, 2H); 2.80 (s, 3H); 2.30 (m, 2H); 2.00 (m, 4H). |
| 22 | 8.70 (broad s, 1H); 8.30 (m, 1H); 7.80 (dl, 1H); 6.80 (m, 2H); 6.70 (s, 1H); 5.20 (s, 2H); 4.10 (m, 1H); 3.50 (m, 2H); 3.40 (m, 2H); 2.80 (s, 3H); 2.30 (m, 2H); 2.00 (m, 4H). |
| 23 | 8.70 (m, 1H); 8.40 (m, 2H); 7.80 (m, 2H); 7.60 (m, 2H); 7.25 (m, 2H); 6.80 (s, 1H); 6.40 (d, 1H); 5.20 (s, 2H); 4.00 (s, 2H); 3.95 (m, 1H); 3.90 (m, 2H); 2.80 (s, 3H); 2.50 (m, 2H); 2.20 (m, 2H). |
| 24 | 8.70 (d, 1H); 8.15 (broad s, 1H); 7.85 (broad s, 1H); 7.75 (broad s, 1H); 6.95 (d, 1H); 6.75 (s, 1H); 5.20 (s, 2H); 4.05 (m, 1H); 3.80 (m, 2H); 3.70 (m, 2H); 2.20 (m, 2H); 1.80 (m, 2H); 1.60 (m, 2H); 1.50 (m, 2H). |
| 25 | 8.40 (s, 1H); 8.30 (s, 1H); 8.10 (m, 3H); 7.85 (broad s, 1H); 7.75 (dl, 1H); 7.30 (m, 2H); 6.80 (s, 1H); 5.20 (s, 2H); 4.05 (m, 1H); 3.65 (m, 2H); 3.55 (m, 2H); 2.10 (m, 2H); 1.80 (m, 2H); 1.65 (m, 2H); 1.60 (m, 2H). |

TABLE 2-continued

| No. | $^1$H NMR (DMSO or CDCl$_3$ 400 MHZ) δ (ppm) |
|---|---|
| 26 | 10.10 (broad s, 1H); 9.00 (m, 1H); 8.60 (m, 1H); 7.70 (broad s, 1H); 6.90 (m, 1H); 6.80 (m, 1H); 5.20 (s, 2H); 4.00 (m, 1H); 3.70 (m, 2H); 3.60 (m, 4H); 3.35 (m, 2H); 2.80 (s, 6H); 2.20 (m, 2H); 1.70 (m, 2H); 1.60 (m, 2H); 1.50 (m, 2H). |
| 27 | 8.15 (m, 2H); 7.85 (m, 3H); 7.75 (dl, 1H); 7.30 (m, 2H); 7.00 (s, 1H); 6.90 (d, 1H); 6.75 (s, 1H); 5.20 (s, 2H); 4.05 (m, 1H); 3.60 (m, 2H); 3.50 (m, 2H); 2.10 (m, 2H); 1.75 (m, 2H); 1.60 (m, 2H); 1.50 (m, 2H). |
| 28 | 8.15 (broad s, 1H); 8.05 (d, 1H); 7.80 (broad s, 1H); 7.75 (dl, 1H); 6.90 (s, 1H); 6.80 (s, 1H); 6.65 (d, 1H); 5.20 (s, 2H); 4.00 (m, 1H); 3.50 (m, 2H); 3.40 (m, 2H); 2.20 (m, 2H); 1.70 (m, 2H); 1.55 (m, 2H); 1.50 (m, 2H). |
| 29 | 8.30 (d, 1H); 8.15 (broad s, 1H); 7.85 (broad s, 1H); 7.75 (dl, 1H); 7.10 (s, 1H); 6.85 (d, 1H); 6.80 (s, 1H); 5.20 (s, 2H); 4.05 (m, 1H); 3.60 (m, 2H); 3.50 (m, 2H); 2.20 (m, 2H); 1.80 (m, 2H); 1.60 (m, 2H); 1.50 (m, 2H). |
| 30 | 8.50 (s, 1H); 8.15 (broad s, 1H); 7.90 (m, 2H); 7.65 (dl, 1H); 7.50 (m, 3H); 7.10 (m, 1H); 6.90 (d, 1H); 6.80 (s, 1H); 5.20 (s, 2H); 4.05 (m, 1H); 3.60 (m, 2H); 3.50 (m, 2H); 2.20 (m, 2H); 1.70 (m, 2H); 1.60 (m, 2H); 1.50 (m, 2H). |
| 31 | 8.15 (m, 1H); 7.90 (m, 1H); 7.85 (m, 1H); 7.75 (m, 1H); 7.30 (m, 1H); 6.75 (m, 2H); 5.20 (s, 2H); 4.00 (m, 1H); 3.40 (m, 2H); 3.35 (m, 2H); 2.30 (m, 2H); 2.20 (m, 2H); 1.75 (m, 3H); 1.55 (m, 4H); 0.85 (d, 6H). |
| 32 | 8.15 (s, 1H); 8.00 (d, 1H); 7.85 (m, 1H); 7.80 (m, 2H); 7.50 (m, 2H); 7.30 (d, 1H); 6.80 (s, 1H); 5.20 (s, 2H); 4.05 (m, 1H); 3.70 (m, 2H); 3.60 (m, 2H); 2.20 (m, 2H); 1.75 (m, 2H); 1.65 (m, 2H); 1.55 (m, 2H). |
| 33 | 8.70 (m, 1H); 8.00 (d, 1H); 7.80 (s, 1H); 7.55 (m, 3H); 7.30 (d, 1H); 6.80 (s, 1H); 5.20 (s, 2H); 3.70 (m, 2H); 3.60 (m, 2H); 3.10 (m, 2H); 2.80 (d, 3H); 2.40 (m, 1H); 1.90 (m, 2H); 1.60 (m, 2H); 1.50 (m, 4H). |
| 34 | 8.70 (broad s, 1H); 8.30 (d, 1H); 7.75 (dl, 1H); 7.05 (s, 1H); 6.80 (d, 1H); 6.75 (s, 1H); 5.20 (s, 2H); 4.05 (m, 1H); 3.60 (m, 2H); 3.50 (m, 2H); 2.80 (s, 3H); 2.20 (m, 2H); 1.80 (m, 2H); 1.60 (m, 2H); 1.50 (m, 2H). |
| 35 | 8.30 (d, 1H); 8.10 (m, 1H); 8.95 (dl, 1H); 7.45 (m, 2H); 7.05 (s, 1H); 6.80 (d, 1H); 5.40 (s, 2H); 4.05 (m, 1H); 3.55 (m, 4H); 2.20 (m, 2H); 1.80 (m, 2H); 1.60 (m, 4H). |
| 36 | 8.60 (s, 1H); 8.30 (d, 1H); 7.80 (dl, 1H); 7.60 (broad s, 1H); 7.50 (broad s, 1H); 7.05 (s, 1H); 6.80 (d, 1H); 5.10 (s, 2H); 4.00 (m, 1H); 3.50 (m, 4H); 2.20 (m, 2H); 1.70 (m, 2H); 1.50 (m, 4H). |
| 37 | 8.30 (d, 1H); 7.75 (m, 2H); 7.55 (m, 4H); 7.10 (s, 1H), 6.80 (d, 1H); 4.95 (s, 2H); 4.05 (m, 1H); 3.50 (m, 4H); 2.50 (s, 3H); 2.20 (m, 2H); 1.70 (m, 2H); 1.55 (m, 4H). |
| 38 | 8.30 (d, 1H); 7.90 (m, 1H); 7.10 (s, 1H); 6.80 (d, 1H); 5.30 (s, 2H); 4.00 (m, 1H); 3.55 (m, 4H); 2.75 (q, 2H); 2.10 (m, 2H); 1.80 (m, 2H); 1.55 (m, 4H); 1.25 (t, 3H). |
| 39 | 8.30 (d, 1H); 7.75 (m, 2H); 7.10 (s, 1H); 6.80 (d, 1H); 5.10 (s, 2H); 4.05 (m, 1H); 3.55 (m, 1H); 3.55 (m, 4H); 2.60 (s, 3H); 2.20 (m, 2H); 1.75 (m, 2H); 1.55 (m, 4H). |
| 40 | 8.70 (d, 1H); 8.15 (broad s, 1H); 7.85 (broad s, 1H); 7.70 (broad s, 1H); 7.00 (d, 1H); 6.80 (s, 1H); 5.20 (s, 2H); 3.90 (m, 2H); 3.75 (m, 2H); 2.50 (m, 1H); 1.40 (m, 3H); 1.30 (m, 1H); 1.70 (m, 1H); 1.50 (m, 1H) |
| 41 | 8.70 (m, 2H); 7.70 (broad s, 1H); 7.00 (d, 1H); 6.80 (s, 1H); 5.20 (s, 2H); 3.90 (m, 2H); 3.70 (m, 2H); 2.80 (d, 3H); 2.50 (m, 1H); 1.40 (m, 3H); 1.30 (m, 1H); 1.70 (m, 1H); 1.50 (m, 1H) |

Table 3 that follows gives the results of the LC-MS analyses for the compounds of Table 1.

LC-MS method (M+H):

UPLC/TOF—Gradient 3 min—H$_2$O/ACN/TFA T0: 98% A—T 1, 6 to T 2.1 min: 100% B—T 2.5 to T 3 min: 98% A Route A: H$_2$O+0.05% TFA; Route B: ACN+0.035% TFA flow rate: 1.0 mL/min—T°=40° C.—Injection 2 μL—Acquity BEH C18 (50*2.1 mm; 1.7 μm) column"; 220 nm

TABLE 3

| No. | LCUVMS MASS | RETENTION TIME (min) | ion observed |
|---|---|---|---|
| 1 | 427 | 0.78 | MH+ |
| 2 | 454 | 0.74 | MH+ |
| 3 | 454 | 0.95 | MH+ |
| 4 | 464 | 0.82 | MH+ |
| 5 | 480 | 0.84 | MH+ |
| 6 | 468 | 0.78 | MH+ |
| 7 | 482 | 0.80 | MH+ |
| 8 | 494 | 0.87 | MH+ |
| 9 | 468 | 0.76 | MH+ |
| 10 | 466 | 0.80 | MH+ |
| 11 | 480 | 0.83 | MH+ |
| 12 | 494 | 0.88 | MH+ |
| 13 | 494 | 0.88 | MH+ |
| 14 | 454 | 0.71 | MH+ |
| 15 | 440 | 0.73 | MH+ |
| 16 | 468 | 0.77 | MH+ |
| 17 | 480 | 0.83 | MH+ |
| 18 | 480 | 0.83 | MH+ |
| 19 | 484 | 0.83 | MH+ |
| 20 | 452 | 0.86 | MH+ |
| 21 | 464 | 0.77 | MH+ |
| 22 | 454 | 0.83 | MH+ |
| 23 | 466 | 0.89 | MH+ |
| 24 | 455 | 1.24 | MH+ |
| 25 | 481 | 1.15 | MH+ |
| 26 | 526 | 1.11 | MH+ |
| 27 | 480 | 0.92 | MH+ |
| 28 | 420 | 0.76 | MH+ |
| 29 | 454 | 0.95 | MH+ |
| 30 | 480 | 0.92 | MH+ |
| 31 | 442 | 0.91 | MH+ |
| 32 | 470 | 0.87 | MH+ |
| 33 | 498 | 0.97 | MH+ |
| 34 | 468 | 1.16 | MH+ |
| 35 | 506 | 1.24 | MH+ |
| 36 | 454 | 0.85 | MH+ |
| 37 | 501 | 1.25 | MH+ |
| 38 | 440 | 1.06 | MH+ |
| 39 | 426 | 0.97 | MH+ |
| 40 | 441 | 1.11 | MH+ |
| 41 | 455 | 1.18 | MH+ |

The compounds of the invention underwent pharmacological tests to determine their inhibitory effect on the enzyme FAAH (Fatty Acid Amide Hydrolase).

The inhibitory activity was demonstrated in a radioenzymatic test based on measuring the product of hydrolysis of anandamide [ethanolamine 1-$^3$H] with FAAH (*Life Sciences* (1995), 56, 1999-2005 and *Journal of Biochemical and Biophysical Methods* (2004), 60 (2), 171-177). Thus, mouse brains (minus the cerebellum) are removed and stored at −80° C. The membrane homogenates are prepared extemporaneously by homogenizing the tissues using a Precellys® machine in reaction buffer (10 mM Tris-HCl, pH=8, 150 mM NaCl and 1 mM ethylenediaminetetraacetic acid (EDTA)). The enzymatic reaction is performed in 96-well Multiscreen filtration plates in a final volume of 70 μL. Reaction buffer supplemented with fatty acid-free bovine serum albumin (BSA, 1 mg/ml) is used for the enzymatic reaction and the dilution of the compounds and of the anandamide [ethanolamine 1-$^3$H]. The reaction buffer containing BSA (43 μL/well), the diluted test compounds at different concentrations (7 μL/well containing 1% DMSO) and the membrane preparation (10 μL/well, i.e. 200 μg of tissue per test) are successively added to the wells. After preincubation for 20 minutes of the compounds with the enzyme at 25° C., the reaction is started by adding anandamide [ethanolamine 1-$^3$H]. (Specific activity of 15-20 Ci/mmol) diluted with cold anandamide (10 μL/well, final concentration of 10 μM, 0.01 μCi per test). After incubation for 20 minutes at 25° C., the enzymatic reaction is stopped by adding a 5M solution of active charcoal prepared in 1.5M NaCl buffer and 0.5 M HCl (50 µL/well). The mixture is stirred for 10 minutes and the aqueous phase containing the ethanolamine [1-$^3$H] is then recovered by filtration under vacuum and counted by liquid scintillation.

Under these conditions, the most active compounds of the invention have $IC_{50}$ values (concentration that inhibits 50% of the control enzymatic activity of FAAH) of between 0.001 and 1 µM; for example, compounds 4, 6, 8, 10, 12, 19, 25, 31 and 40 have respective $IC_{50}$ values of 0.0082, 0.00025, 0.00072, 0.0023, 0.00085, 0.0018, 0.0017, 0.0043 and 0.0005 µM.

It thus appears that the compounds according to the invention have inhibitory activity on the enzyme FAAH.

The in vivo activity of the compounds of the invention was evaluated in a test of analgesia.

Thus, the intraperitoneal (i.p.) administration of PBQ (phenylbenzoquinone, 2 mg/kg in 0.9% sodium chloride solution containing 5% ethanol) to male OF1 mice weighing 25 to 30 g causes abdominal stretching, on average 30 torsions or contractions within a period of 5 to 15 minutes after injection. The test compounds are administered orally (p.o.) or intraperitoneally (i.p.) suspended in Tween 80 at 0.5%, 60 minutes or 120 minutes before the administration of PBQ. Under these conditions, the compounds of the invention that are the most powerful reduce by 35% to 80% the number of stretches induced with PBQ, over a dose range of between 1 and 30 mg/kg.

For example, compound 5 of Table 1 reduces by 50% the number of stretches induced with PBQ, at a dose of 30 mg/kg p.o. at 120 minutes.

The enzyme FAAH (*Chemistry and Physics of Lipids*, (2000), 108, 107-121) catalyses the hydrolysis of the endogenous derivatives of amides and esters of various fatty acids such as N-arachidonoylethanolamine (anandamide), N-palmitoylethanolamine, N-oleoylethanolamine, oleamide or 2-arachidonoylglycerol. These derivatives exert different pharmacological activities by interacting, inter alia, with the cannabinoid and vanilloid receptors.

The compounds of the invention block this degradation pathway and increase the tissue content of these endogenous substances. In this respect, they may be used in the prevention and treatment of pathologies in which the endogenous cannabinoids and/or any other substrate metabolized by the enzyme FAAH are involved. Mention may be made, for example, of the following diseases and complaints:

pain, especially acute or chronic pain of neurogenic type: migraine, neuropathic pain including the forms associated with the herpes virus and diabetes and chemotherapy, acute or chronic pain associated with inflammatory diseases: arthritis, rheumatoid arthritis, osteoarthritis, spondylitis, gout, vascularitis, Crohn's disease, irritable bowel syndrome, acute or chronic peripheral pain, vertigo, vomiting, nausea, in particular post-chemotherapy nausea, eating disorders, in particular anorexia and cachexia of diverse nature, neurological and psychiatric pathologies: tremor, dyskinaesia, dystonia, spasticity, compulsive and obsessive behaviour, Tourette's syndrome, all forms of depression and anxiety of any nature or origin, mood disorders, psychoses, acute and chronic neurodegenerative diseases: Parkinson's disease, Alzheimer's disease, senile dementia, Huntington's chorea, lesions associated with cerebral ischaemia and cranial and medullary trauma, epilepsy, sleeping disorders, including sleep apnoea, cardiovascular diseases, in particular hypertension, cardiac arrhythmia, arteriosclerosis, heart attack, cardiac ischaemia, renal ischaemia, cancers: benign skin tumours, papillomas and cerebral tumours, prostate tumours, cerebral tumours (gliobastomas, medullo-epitheliomas, medullo-blastomas, neuroblastomas, tumours of embryonic origin, astrocytomas, astroblastomas, ependyomas, oligodendrogliomas, plexus tumour, neuroepitheliomas, pineal gland tumours, ependymoblastomas, malignant meningiomas, sarcomatoses, malignant melanomas, schwennomas), immune system disorders, especially autoimmune diseases: psoriasis, lupus erythematosus, connective tissue diseases, Sjögrer's syndrome, ankylosing spondylitis, undifferentiated spondylitis, Behcet's disease, haemolytic autoimmune anaemias, multiple sclerosis, amyotrophic lateral sclerosis, amylosis, graft rejection, diseases affecting the plasmocytic line, allergic diseases: immediate or delayed hypersensitivity, allergic rhinitis or allergic conjunctivitis, contact dermatitis, parasitic, viral or bacterial infectious diseases: AIDS, meningitis, inflammatory diseases, especially articular diseases: arthritis, rheumatoid arthritis, osteoarthritis, spondylitis, gout, vascularitis, Crohn's disease, irritable bowel syndrome, osteoporosis, ocular complaints: ocular hypertension, glaucoma, pulmonary complaints: respiratory pathway diseases, bronchospasms, coughing, asthma, chronic bronchitis, chronic obstruction of the respiratory pathways, emphysema, gastrointestinal diseases: irritable bowel syndrome, intestinal inflammatory disorders, ulcers, diarrhoea, urinary incontinence and inflammation of the bladder.

The use of the compounds according to the invention, in the form of the base, or a pharmaceutically acceptable acid-addition salt, hydrate or solvate, for the preparation of a medicinal product for treating the pathologies mentioned above forms an integral part of the invention.

A subject of the invention is also medicinal products comprising a compound of formula (I), or an acid-addition salt, or alternatively a pharmaceutically acceptable hydrate or solvate of the compound of formula (I). These medicinal products find their therapeutic use especially in the treatment of the pathologies mentioned above.

According to another of its aspects, the present invention relates to pharmaceutical compositions containing, as active principal, at least one compound according to the invention. These pharmaceutical compounds contain an effective dose of a compound according to the invention, or a pharmaceutically acceptable acid-addition salt, hydrate or solvate of the said compound, and optionally one or more pharmaceutically acceptable excipients.

The said excipients are chosen, according to the pharmaceutical form and the desired administration form, from the usual excipients known to those skilled in the art.

In the pharmaceutical compositions of the present invention for oral, sublingual, subcutaneous, intramuscular, intravenous, topical, local, intrathecal, intranasal, transdermal, pulmonary, ocular or rectal administration, the active principal of formula (I) above, or the possible acid-addition salt, solvate or hydrate thereof, may be administered in a unit administration form, as a mixture with standard pharmaceutical excipients, to man and animals for the prophylaxis or treatment of the above disorders or diseases.

The appropriate unit administration forms comprise oral forms such as tablets, soft or hard gel capsules, powders, granules, chewing gums and oral solutions or suspensions, sublingual, buccal, intratracheal, intraocular and intranasal administration forms, forms for administration by inhalation, subcutaneous, intramuscular or intravenous administration forms and rectal or vaginal administration forms. For topical administration, the compounds according to the invention may be used in creams, ointments or lotions.

By way of example, a unit administration form of a compound according to the invention in the form of a tablet may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

The said unit forms are dosed to allow a daily administration of from 0.01 to 20 mg of active principal per kg of body weight, depending on the presentation form.

There may be particular cases in which higher or lower doses are suitable, and such doses also form part of the invention. According to the usual practice, the dose that is suitable for each patient is determined by the doctor according to the mode of administration and the weight and response of the said patient.

According to another of its aspects, the invention also relates to a method for treating the pathologies mentioned above, which comprises the administration of an effective dose of a compound according to the invention, a pharmaceutically acceptable acid-addition salt thereof or a solvate or hydrate of the said compound.

The invention claimed is:

1. Compound corresponding to formula (I)

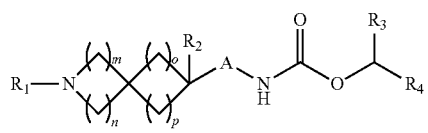

(I)

in which $R_2$ represents a hydrogen or fluorine atom or a hydroxyl, cyano, trifluoromethyl, $C_{1-6}$-alkyl, $C_{1-6}$-alkoxy or $NR_8R_9$ group;

m, n, o and p represent, independently of each other, an integer equal to 0, 1, 2 or 3;

A represents a covalent bond or a group $C_{1-8}$-alkylene;

$R_1$ represents a group $R_5$ optionally substituted with one or more groups $R_6$ and/or $R_7$;

$R_5$ represents a group chosen from phenyl, pyridyl, pyridazinyl, pyrimidinyl, pyrazinyl, triazinyl, naphthyl, quinolinyl, isoquinolinyl, phthalazinyl, quinazolinyl, quinoxalinyl, cinnolinyl and naphthyridinyl;

$R_6$ represents a halogen atom or a $C_{1-6}$-alkyl, or $C_{1-6}$-haloalkyl group;

$R_7$ represents phenyl ring optionally substituted with one or more groups $R_6$ that may be identical to or different from each other;

$R_3$ represents a hydrogen or fluorine atom, a group $C_{1-6}$-alkyl or a trifluoromethyl group;

$R_4$ represents a group chosen from furyl, pyrrolyl, thienyl, isothiazolyl, oxazolyl, isoxazolyl, pyrazolyl, oxadiazolyl, thiadiazolyl, imidazolyl, triazolyl and tetrazolyl;

this group being optionally substituted with one or more substituents chosen from a halogen atom, a group $C_{1-6}$-alkyl, $C_{1-6}$-haloalkyl, $C_{3-7}$-cycloalkyl, $C_{3-7}$-cycloalkyl-$C_{1-3}$-alkylene, $C_{1-6}$-haloalkoxy, cyano, $NR_8R_9$, $NR_8COR_9$, $NR_8CO_2R_9$, $NR_8SO_2R_9$, $NR_8SO_2NR_8R_9$, $COR_8$, $CO_2R_8$, $CONR_8R_9$, $CON(R_8)(C_{1-3}$-alkylene-$NR_{10}R_{11})$, $SO_2R_8$, $SO_2NR_8R_9$, —O—($C_{1-3}$-alkylene)-O—, and phenyl; the phenyl groups possibly being substituted with one or more substituents chosen from a halogen atom and a cyano, nitro, $C_{1-6}$-alkyl, $C_{1-6}$-alkoxy, $C_{1-6}$-thioalkyl, $C_{1-6}$-haloalkoxy, $C_{1-6}$-halothioalkyl, $C_{3-7}$-cycloalkyl or $C_{3-7}$-cycloalkyl-$C_{1-3}$-alkylene group; $R_8$ and $R_9$ represent, independently of each other, a hydrogen atom or a group $C_{1-6}$-alkyl, $R_{10}$ and $R_{11}$ represent, independently of each other, a hydrogen atom or a group $C_{1-6}$-alkyl;

in the form of base or of acid-addition salt.

2. The compound according to claim 1, wherein $R_2$ represents a hydrogen atom;

in the form of base or of acid-addition salt.

3. The compound according to claim 1, wherein the group

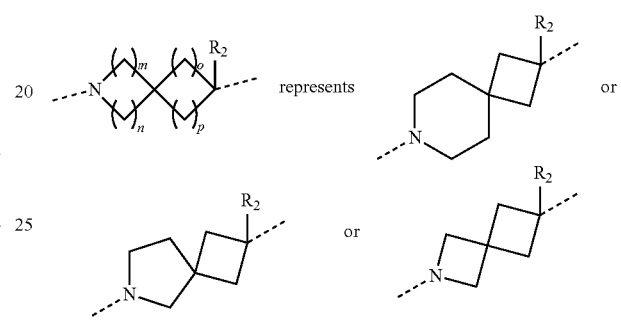

$R_2$ as defined in the general formula (I) according to claim 1;

in the form of base or of acid-addition salt.

4. The compound according to claim 1, wherein $R_1$ represents a group $R_5$ optionally substituted with one or more groups $R_6$ and/or $R_7$;

$R_5$ represents a pyrimidinyl, pyrazinyl, pyridinyl or quinolinyl group;

in the form of base or of acid-addition salt.

5. The compound according to claim 1, wherein $R_3$ represents a hydrogen atom; in the form of base or of acid-addition salt.

6. The compound according to claim 1, wherein $R_4$ represents a group chosen from a thiazolyl, an oxazolyl, an oxadiazolyl and an isoxazolyl;

this group being optionally substituted with one or more substituents chosen from a group $C_{1-6}$-alkyl, $CONR_8R_9$, $CON(R_8)(C_{1-3}$-alkylene-$NR_{10}R_{11})$ or a phenyl; the phenyl group being optionally substituted with one or more substituents chosen from a halogen atom;

$R_8$, $R_9$, $R_{10}$ and $R_{11}$ represent, independently of each other, a hydrogen atom or a group $C_{1-6}$-alkyl;

in the form of base or of acid-addition salt.

7. The compound according to claim 1, wherein it is chosen from:

thiazol-4-ylmethyl[7-(6-fluoroquinolin-2-yl)-7-azaspiro[3.5]non-2-yl]carbamate 3-carbamoylisoxazol-5-ylmethyl[7-(6-fluoroquinolin-2-yl)-7-azaspiro[3.5]non-2-yl]carbamate 3-carbamoylisoxazol-5-ylmethyl[7-(5-trifluoromethylpyridin-2-yl)-7-azaspiro[3.5]non-2-yl]carbamate 3-carbamoylisoxazol-5-ylmethyl[7-(5-bromopyridin-2-yl)-7-azaspiro[3.5]non-2-yl]carbamate 3-carbamoylisoxazol-5-ylmethyl{7-[5-(4-fluorophenyl)pyridin-2-yl]-7-azaspiro[3.5]non-2-yl}carbamate 3-carbamoylisoxazol-5-ylmethyl[7-(6-fluoroquinolin-2-yl)-7-azaspiro[3.5]non-2-yl]methylcarbamate 3-(methylcarbamoyl)isoxazol-5-ylmethyl[7-(6-fluoro-quinolin-2-yl)-7-azaspiro[3.5]non-2-yl]methylcarbamate
3-(methylcarbamoyl)isoxazol-5-ylmethyl{7-[5-(4-fluorophenyl)pyridin-2-yl]-7-azaspiro[3.5]non-2-yl}carbamate
3-(methylcarbamoyl)isoxazol-5-ylmethyl[7-(6-fluoro-quinolin-2-yl)-7-azaspiro[3.5]non-2-yl]carbamate
3-carbamoylisoxazol-5-ylmethyl{6-[5-(4-fluorophenyl)pyridin-2-yl]-6-azaspiro[3.4]oct-2-yl}carbamate
3-(methylcarbamoyl)isoxazol-5-ylmethyl{6-[5-(4-fluorophenyl)pyridin-2-yl]-6-azaspiro[3.4]oct-2-yl}carbamate
3-(methylcarbamoyl)isoxazol-5-ylmethyl{6-[5-(4-fluorophenyl)pyridin-2-yl]-6-azaspiro[3.4]oct-2-ylmethyl}carbamate
3-(methylcarbamoyl)isoxazol-5-ylmethyl{6-[5-(4-fluorophenyl)pyridin-2-yl]-6-azaspiro[3.4]oct-2-ylmethyl}carbamate
4-carbamoyloxazol-2-ylmethyl[7-(6-fluoroquinolin-2-yl)-7-azaspiro[3.5]non-2-yl]carbamate
3-(methylcarbamoyl)isoxazol-5-ylmethyl[2-(6-fluoro-quinolin-2-yl)-2-azaspiro[3.3]hept-6-yl]carbamate
3-(methylcarbamoyl)isoxazol-5-ylmethyl[6-(6-fluoro-quinolin-2-yl)-6-azaspiro[3.4]oct-2-ylmethyl]carbamate
3-(methylcarbamoyl)isoxazol-5-ylmethyl{6-[5-(4-fluorophenyl)pyridin-2-yl]-6-azaspiro[3.4]oct-2-yl}carbamate
3-(methylcarbamoyl)isoxazol-5-ylmethyl{6-[5-(4-fluorophenyl)pyridin-2-yl]-6-azaspiro[3.4]oct-2-yl}carbamate
3-(methylcarbamoyl)isoxazol-5-ylmethyl[7-(6-chloro-quinolin-2-yl)-7-azaspiro[3.5]non-2-yl]carbamate
3-carbamoylisoxazol-5-ylmethyl{2-[5-(4-fluorophenyl)pyridin-2-yl]-2-azaspiro[3.3]hept-6-yl}carbamate
3-methylcarbamoylisoxazol-5-ylmethyl[6-(5-bromopyridin-2-yl)-6-azaspiro[3.4]oct-2-yl]carbamate
3-methylcarbamoylisoxazol-5-ylmethyl[6-(4-trifluoromethylpyridin-2-yl)-6-azaspiro[3.4]oct-2-yl]carbamate
3-methylcarbamoylisoxazol-5-ylmethyl{2-[5-(4-fluorophenyl)pyridin-2-yl]-2-azaspiro[3.3]hept-6-yl}carbamate
3-carbamoylisoxazol-5-ylmethyl[7-(4-trifluoromethylpyrimidin-2-yl)-7-azaspiro[3.5]non-2-yl]carbamate
3-carbamoylisoxazol-5-ylmethyl{7-[6-(4-fluorophenyl)pyrazin-2-yl]-7-azaspiro[3.5]non-2-yl}carbamate
3-(2-dimethylaminoethylcarbamoyl)isoxazol-5-ylmethyl[7-(4-trifluoromethylpyrimidin-2-yl)-7-azaspiro[3.5]non-2-yl]carbamate and the hydrochloride thereof;
3-carbamoylisoxazol-5-ylmethyl{7-[4-(4-fluorophenyl)pyridin-2-yl]-7-azaspiro[3.5]non-2-yl}carbamate
3-carbamoylisoxazol-5-ylmethyl[7-(4-chloropyridin-2-yl)-7-azaspiro[3.5]non-2-yl]carbamate
3-carbamoylisoxazol-5-ylmethyl[7-(4-trifluoromethylpyridin-2-yl)-7-azaspiro[3.5]non-2-yl]carbamate
3-carbamoylisoxazol-5-ylmethyl{7-[5-(3-fluorophenyl)pyridin-2-yl]-7-azaspiro[3.5]non-2-yl}carbamate
3-carbamoylisoxazol-5-ylmethyl[7-(5-isobutylpyridin-2-yl)-7-azaspiro[3.5]non-2-yl]carbamate
3-carbamoylisoxazol-5-ylmethyl[7-(6-chloroquinolin-2-yl)-7-azaspiro[3.5]non-2-yl]carbamate
3-methylcarbamoylisoxazol-5-ylmethyl[7-(6-chloro-quinolin-2-yl)-7-azaspiro[3.5]non-2-ylmethyl]carbamate
3-methylcarbamoylisoxazol-5-ylmethyl[7-(4-trifluoromethylpyridin-2-yl)-7-azaspiro[3.5]non-2-yl]carbamate
3-(4-fluorophenyl)-[1,2,4]oxadiazol-5-ylmethyl[7-(4-trifluoromethylpyridin-2-yl)-7-azaspiro[3.5]non-2-yl]carbamate
4-carbamoyloxazol-2-ylmethyl[7-(4-trifluoromethylpyridin-2-yl)-7-azaspiro[3.5]non-2-yl]carbamate
5-methyl-3-phenylisoxazol-4-ylmethyl[7-(4-trifluoromethylpyridin-2-yl)-7-azaspiro[3.5]non-2-yl]carbamate
3-ethyl[1,2,4]oxadiazol-5-ylmethyl[7-(4-trifluoromethylpyridin-2-yl)-7-azaspiro[3.5]non-2-yl]carbamate
5-methyl[1,2,4]oxadiazol-3-ylmethyl[7-(4-trifluoromethylpyridin-2-yl)-7-azaspiro[3.5]non-2-yl]carbamate
3-carbamoylisoxazol-5-ylmethyl[6-(4-trifluoromethylpyrimidin-2-yl)-6-azaspiro[2.5]oct-1-yl]carbamate
3-methylcarbamoylisoxazol-5-ylmethyl[6-(4-trifluoromethylpyrimidin-2-yl)-6-azaspiro[2.5]oct-1-yl]carbamate.

8. A process for preparing the compound of formula (I) according to claim 1, comprising the step that consists in reacting an amine of general formula (II),

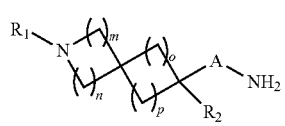

(II)

in which A, $R_1$, $R_2$, m, n, o and p are as defined in the general formula (I) according to claim 1, either with a carbonate of general formula (III)

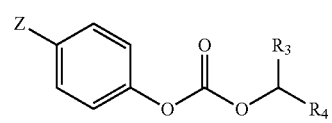

(III)

in which Z represents a hydrogen atom or a nitro group, and $R_3$ and $R_4$ are as defined in the general formula (I) according to claim 1,
in the presence of a base, in a solvent at a temperature of between room temperature and the reflux temperature of the solvent;
or with phenyl or 4-nitrophenyl chloroformate,
in the presence of a base, in a solvent at a temperature of between 0° C. and room temperature, to give the carbamate derivative of general formula (IV),

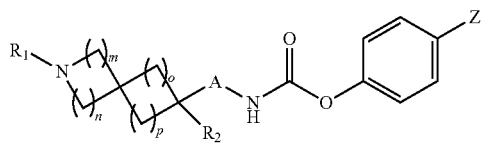

(IV)

in which A, $R_1$, $R_2$, m, n, o and p are as defined in the general formula (I) according to claim 1, and Z represents a hydrogen atom or a nitro group,
and then in converting the carbamate derivative of general formula (IV) thus obtained into a compound of general formula (I), via the action of an alcohol of general formula HOCHR$_3$R$_4$ (IIIa), in which $R_3$ and $R_4$ are as defined in the general formula (I) according to claim 1, in the presence of a base, in a solvent at a temperature of between room temperature and the reflux temperature of the solvent.

9. A process for preparing a compound of formula (I) according to claim 1, comprising the step that consists in reacting a compound of general formula (Ia)

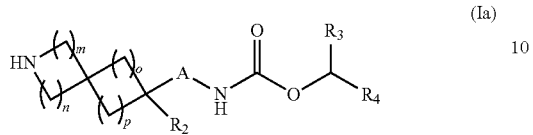

(Ia)

in which A, $R_2$, $R_3$, $R_4$, m, n, o and p are as defined in the general formula (I) according to claim 1, with a derivative of general formula $R_1$—U (V), in which $R_1$ is as defined in the general formula (I) according to claim 1 and $U_1$ represents a halogen atom or an O-triflate group, using aromatic or heteroaromatic nucleophilic substitution conditions or using Buchwald N-arylation or N-heteroarylation conditions.

10. A process for preparing a compound of formula (I) according to claim 1, in which $R_1$ represents a group $R_5$ substituted with a group $R_6$ of the type $C_{1-6}$-alkyl, or with a group $R_7$ as defined in the general formula (I) according to claim 1, comprising the step that consists in performing a coupling reaction, catalysed by means of a transition metal, on the compound of general formula (Ib),

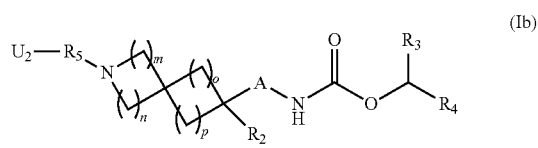

(Ib)

in which A, $R_2$, $R_3$, $R_4$, $R_5$, m, n, o and p are as defined in the general formula (I) according to claim 1 and $U_2$ represents a chlorine, bromine or iodine atom or a triflate group, $U_2$ being in the position in which it is desired to introduce a group $R_6$ or $R_7$:

either via a reaction of Suzuki type, for example using an alkyl, cycloalkyl, aryl or heteroaryl boronic acid, or according to a reaction of Stille type;

or via a reaction of Negishi type.

11. A pharmaceutical composition containing at least one compound of formula (I) according to claim 1, in the form of base or of a pharmaceutically acceptable acid-addition salt and optionally one or more pharmaceutically acceptable excipients.

12. A method of treating acute or chronic pain in a patient in need thereof comprising administering to said patient a therapeutically effective amount of the pharmaceutical composition of claim 11.

\* \* \* \* \*

UNITED STATES PATENT AND TRADEMARK OFFICE
CERTIFICATE OF CORRECTION

PATENT NO.         : 8,889,702 B2                                          Page 1 of 1
APPLICATION NO.    : 13/145926
DATED              : November 18, 2014
INVENTOR(S)        : Ahmed Abouabdellah et al.

It is certified that error appears in the above-identified patent and that said Letters Patent is hereby corrected as shown below:

In the Claims:

At column 57, claim number 1, line number 67, through column 58, line number 1, please replace "-O-($C_{1-3}$-alkylene)-O-," with -- -O-($C_{1-3}$-alkylene)-O- --;

At column 58, claim number 1, line number 4, please replace "$C_{1-6}$-thioalkyl," with -- $C_{1-6}$-thioalkyl, $C_{1-6}$-haloalkyl,--; and At column 61, claim 9, line numbers 20-21, please replace "N-arylation or N-heteroarylation" with --*N*-arylation or *N*-heteroarylation--.

Signed and Sealed this
Eighth Day of September, 2015

Michelle K. Lee
*Director of the United States Patent and Trademark Office*